(12) United States Patent
Lee

(10) Patent No.: US 8,895,032 B2
(45) Date of Patent: Nov. 25, 2014

(54) DENDRITIC NANO-ANTIOXIDANTS

(75) Inventor: Choon Young Lee, Mount Pleasant, MI (US)

(73) Assignee: Central Michigan University, Mount Pleasant, MI (US)

(*) Notice: Subject to any disclaimer, the term of this patent is extended or adjusted under 35 U.S.C. 154(b) by 892 days.

(21) Appl. No.: 12/749,022

(22) Filed: Mar. 29, 2010

(65) Prior Publication Data
US 2010/0247439 A1   Sep. 30, 2010

Related U.S. Application Data

(60) Provisional application No. 61/164,061, filed on Mar. 27, 2009, provisional application No. 61/177,544, filed on May 12, 2009.

(51) Int. Cl.

| | |
|---|---|
| A61K 9/00 | (2006.01) |
| C07C 219/28 | (2006.01) |
| A61Q 19/00 | (2006.01) |
| A23L 1/30 | (2006.01) |
| A61K 47/48 | (2006.01) |
| C07C 215/50 | (2006.01) |
| C07D 249/04 | (2006.01) |
| C07C 217/58 | (2006.01) |
| A61K 8/41 | (2006.01) |
| A61Q 19/08 | (2006.01) |

(52) U.S. Cl.
CPC ............ *C07C 217/58* (2013.01); *C07C 219/28* (2013.01); *A61Q 19/00* (2013.01); *A23L 1/30* (2013.01); *A61K 47/48192* (2013.01); *A61Q 19/08* (2013.01); *C07C 215/50* (2013.01); *C07D 249/04* (2013.01); *A61K 2800/522* (2013.01); *A61K 2800/57* (2013.01); *A61K 8/411* (2013.01)
USPC ......................................................... 424/400

(58) Field of Classification Search
None
See application file for complete search history.

(56) References Cited

U.S. PATENT DOCUMENTS

| | | | |
|---|---|---|---|
| 4,938,885 A | 7/1990 | Migdal | |
| 5,296,330 A * | 3/1994 | Schulz et al. | 430/191 |
| 6,177,414 B1 * | 1/2001 | Tomalia et al. | 514/159 |
| 6,344,206 B1 | 2/2002 | Nguyen et al. | |
| 6,395,867 B1 | 5/2002 | Maignan | |
| 6,410,680 B1 | 6/2002 | Kubota | |
| 2003/0190335 A1 | 10/2003 | Boussouira et al. | |
| 2004/0223986 A9 | 11/2004 | Boussouira et al. | |
| 2007/0264367 A1 | 11/2007 | Kim | |
| 2007/0281991 A1 | 12/2007 | Adrian et al. | |
| 2008/0081074 A1 * | 4/2008 | Gu et al. | 424/489 |
| 2008/0102052 A1 | 5/2008 | Chung et al. | |
| 2010/0258070 A1 * | 10/2010 | Reid | 123/1 A |
| 2011/0171187 A1 * | 7/2011 | Moore et al. | 424/93.51 |

FOREIGN PATENT DOCUMENTS

| | | |
|---|---|---|
| CN | 101704948 | 5/2010 |
| FR | 2761691 | 10/1998 |
| JP | 2005105249 | 4/2005 |
| WO | WO 98/44024 | 10/1998 |
| WO | WO 02/34202 | 5/2002 |

OTHER PUBLICATIONS

Frye, Pentacoordinate silicon derivatives, J. Am. Chem. Soc., 1966, 88(12), 2727-2730.*
Abdel-Magid, A.F. et al., "Reductive amination of aldehydes and ketones with sodium triacetoxyborohydride. Studies on direct and indirect reductive amination procedures," J. Org. Chem. (1996) 61:3849-3862.
Balkwill, F. et al., "Inflammation and cancer: back to Virchow?" Lancet (2001) 357:539-545.
Brand-Williams, W. et al., "Use of a free radical method to evaluate antioxidant activity," Lebensm.-Wiss. U.-Technol. (1995) 28:25-30.
Brown, J.M. et al., "The unique physiology of solid tumors: opportunities and problems for cancer therapy," Cancer Res. (1998) 58:1408-1416.
Ciampolini Inorganic Chemistry, A Practical Guide to Supramolecular Chemistry, "Linear components for supra molecular networks," Chapter 1, Cregg, P.J. editor, John Wiley & Sons (2005) 9-34.
Coussens, L.M. et al., "Inflammation and cancer," Nature (2002) 420:860-867.
Cui, W. et al., "Preparation of dendritic porphyrins and their potential application as antioxidants," Chinese J. Med. Chem. (2007) 17(1):23-28.
Echavarren, A.M. et al., "Palladium-catalyzed coupling of aryl triflates with organostannanes," J. Am. Chem. Soc. (1987) 109:5478-5486.
Esumi, K. et al., "Antioxidant action by gold-PAMAM dendrimer nanocomposites," Langmuir (2004) 20:2536-2538.
Halkes, S.B.A. et al., "Synthesis and biological activity of polygalloyl-dendrimers as stable tannic acid mimics," Bioorg. Med. Chem. Lett. (2002) 12(12):1567-1570.
Lee, C.Y. et al., "Synthesis and antioxidant properties of dendritic polyphenols," Bioorg. Med. Chem. Lett. (2009) 19:6326-6330.
Lee, C.Y. et al., "Potent antioxidant dendrimers lacking pro-oxidant activity," Free Radical Biol. Med. (2011) 50:918-925.

(Continued)

*Primary Examiner* — Paul Dickinson
(74) *Attorney, Agent, or Firm* — Michael Best & Friedrich LLP

(57) ABSTRACT

Provided are dendritic nano-antioxidant compounds according to Formula I, which may further comprise active agents covalently or non-covalently attached. Further provided are compositions comprising the disclosed compounds. Also disclosed are cosmetic compositions and dietary supplements comprising the compounds according to Formula I. The invention additionally provides methods of reducing free radicals or oxidative stress in a cell, a method of treating a subject, and a method of treating a condition comprising administering the compounds according to Formula I.

30 Claims, 34 Drawing Sheets

(56) References Cited

OTHER PUBLICATIONS

Maeda, H. et al., "Nitric oxide and oxygen radicals in infection, inflammation, and cancer," Biochem. (1998) 63:854-865.

Matsumura, T. et al., "New concept for macromolecular therapeutics in cancer chemotherapy," Cancer Res. (1986) 46:6387-6392.

Ohshima, H. et al., "chemical basis of inflammation-induced carcinogenesis," Arch. Biochem. Biophys. (2003) 417:3-11.

Okada, Y. et al., "Antioxidant activity of the new thiosulfinate derivative, S-benzyl phenylmethanethiosulfinate, from *Petiveria alliacea* L.," Org. Biomol. Chem. (2008) 6:1097-1102.

Ozgen, M. et al., "Modified 2,2-azino-bis-3-ethylbenzothiazoline-6-sulfonic acid (ABTS) method to measure antioxidant capacity of selected small fruits and comparison to ferric reducing antioxidant power (FRAP) and 2,2'-diphenyl-l-picrylhydrazyl (DPPH) methods," J. Agric. Food Chem. (2006) 54:1151-1157.

Rajakumar, P. et al., "Synthesis and antioxidant properties of enone core based dendrimers with carbazole as surface group," European J. Med. Chem. (2010) 45(3):1220-1224.

Rice-Evans, C.A. et al., "Structure-antioxidant activity relationships of flavonoids and phenolic acids," Free Radic. Biol. Med. (1996) 20:933-956.

Saa, J.M. et al., "Palladium-catalyzed cross-coupling reactions of highly hindered, electron-rich phenol triflates and organostannanes," J. Org. Chem. (1992) 57:678-685.

Seifried, H.E. et al., "The antioxidant conundrum in cancer," Cancer Res. (2003) 63:4295-4298.

Tang, S. et al., "Synthesis and characterization of water-soluble and photostable L-Dopa dendrimers," Organic Lett. (2006) 8(20):4421-4424.

Uyama, H. et al., "Antioxidant activity of dendrimers conjugated with green tea catechin," PMSE Preprints (2003) 88:120-121.

Wang, B. et al., "Anti-inflammatory and anti-oxidant activity of anionic dendrimer-N-acetyl cysteine conjugates in activated microglial cells," Int. J. Pharm. (2009) 377(1-2):159-168.

* cited by examiner

A. Synthesized Building Blocks

B. Synthesized Branching Units

DENDRITIC NANO-ANTIOXIDANTS

CROSS-REFERENCE TO RELATED APPLICATIONS

This application claims priority to U.S. Provisional Patent Application No. 61/164,061, filed Mar. 27, 2009, and U.S. Provisional Patent Application No. 61/177,544, filed May 12, 2009, each of which is incorporated herein by reference in its entirety.

STATEMENT REGARDING FEDERALLY SPONSORED RESEARCH

The invention was made with government support under 1R15GM087697-01 and 3R15GM087697-01S1 awarded by The National Institute of Health. The government has certain rights in the invention.

BACKGROUND

Oxygen- and nitrogen-based free radicals are produced as a result of metabolism (oxidative phosphorylation), environmental stress, and the immune response. Exposure to excessive concentrations of radicals damages biomolecules, including DNA, proteins, and lipids. Persistent overproduction may cause oxidative stress to cells, ultimately resulting in or contributing to conditions such as inflammation, cancer, asthma, cardiovascular and neurological diseases, as well as age-related disorders. There is a need in the art for synthetic antioxidants for use in scavenging free radicals or reducing oxidative stress.

SUMMARY

In one embodiment, the invention provides a compound according to General Formula I, described below.

In another embodiment, the invention provides a composition comprising at least one active agent covalently attached to a compound according to General Formula I.

In another embodiment, the invention provides a cosmetic composition comprising a compound according to General Formula I.

In another embodiment, the invention provides a dietary supplement comprising a compound according to General Formula I.

In another embodiment the invention provides a method of reducing free radicals or oxidative stress in a cell comprising contacting the cell with an effective amount of a compound according to General Formula I.

In another embodiment the invention provides a method of treatment comprising administering to a subject an effective amount of a compound according to General Formula I.

In another embodiment the invention provides a method of evaluating a subject comprising administering to the subject a composition comprising at least one imaging agent covalently attached or chelated to a compound according to General Formula I, and detecting the imaging agent.

In another embodiment the invention provides a method of delivering an active agent comprising administering a composition comprising at least one active agent covalently attached or chelated to a compound according to General Formula I.

In another embodiment the invention provides a method of treating a condition in a subject comprising administering to the subject a compound according to General Formula I.

Other aspects of the invention will become apparent by consideration of the detailed description and accompanying drawings.

BRIEF DESCRIPTION OF THE DRAWINGS

FIG. 11A is a scheme for the synthesis of a G2 antioxidant dendrimer 76 using a G1 antioxidant dendrimer 16 and building block 23. FIG. 11B is a scheme for the synthesis of a core 78, branching unit 81, a G1 antioxidant dendrimer 82, a G1 antioxidant dendrimer attached to branching units 83, and a G2 antioxidant dendrimer 84. FIG. 11C is a scheme for the synthesis of a core 85 and a G1 antioxidant dendrimer 86.

DETAILED DESCRIPTION

Figure 1:
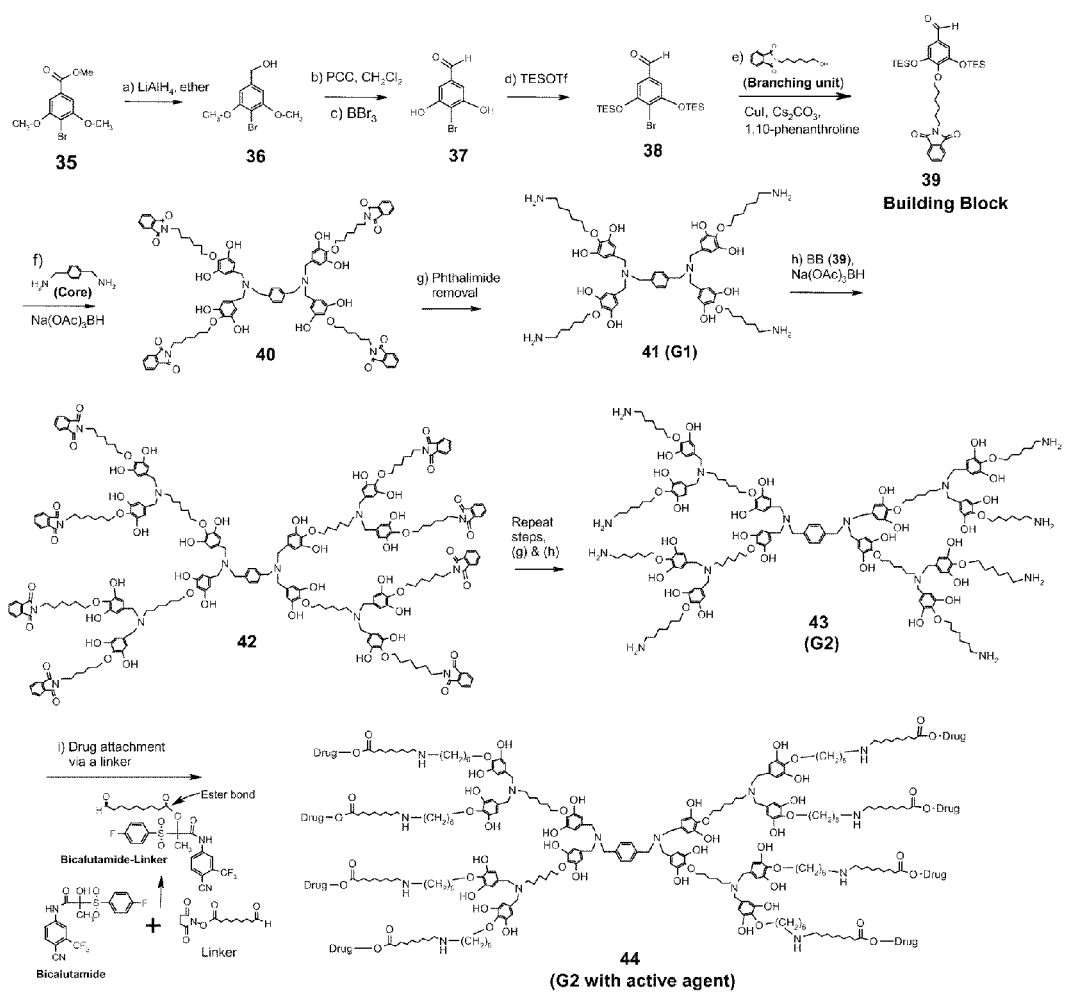
FIG. 1 is a scheme for the synthesis of a G1 antioxidant dendrimer 41, a G2 antioxidant dendrimer 43, and a G2 antioxidant dendrimer with active agent 44.

Described is a new class of compounds referred to herein as dendritic nano-antioxidants. These compounds function in scavenging free radicals. The compounds may have electron donating groups to enhance potential to donate hydrogen (or electrons) to reactive free radicals, and/or double-bonds to extend π conjugation and increase stability through resonance delocalization. Without being limited by theory, it is believed that the phenolic hydroxyl groups of the compounds of the invention may donate hydrogen atoms to free radicals or transfer electrons to free radicals to neutralize the radical, and as such, the compounds may act as antioxidants, radical scavengers, radical absorbers, or agents that reduce oxidative damage. In certain embodiments, the compounds are covalently or non-covalently attached to one or more active agents. The compounds may have a dual function, i.e., the compounds may function as antioxidants as well as function to deliver active agents.

The dendritic structure of the compounds of the invention may facilitate synthesis of precise molecules with increasing size via repetitive synthetic steps. Resulting well-defined molecular structures may be important for clinical applications. In addition, the compounds of the invention may also exhibit enhanced solubility and stability as well as provide other beneficial properties. Compounds of the invention may have strong antioxidant potential and diminished prooxidant activity.

As used herein, "alkyl" refers to a saturated aliphatic hydrocarbon including straight chain and branched chain groups. "Alkyl" may be exemplified by groups such as methyl, ethyl, n-propyl, isopropyl, n-butyl and the like. Alkyl groups may be substituted or unsubstituted. Substituents may also be themselves substituted. When substituted, the substituent group is preferably but not limited to $C_1$-$C_4$ alkyl, aryl, amino, azide, cyano, halogen, alkoxy or hydroxyl. "$C_1$-$C_4$ alkyl" refers to alkyl groups containing one to four carbon atoms. "Alkylene" means a divalent alkyl.

"Alkenyl" refers to an unsaturated aliphatic hydrocarbon moiety including straight chain and branched chain groups. Alkenyl moieties must contain at least one alkene. "Alkenyl" may be exemplified by groups such as ethenyl, n-propenyl, isopropenyl, n-butenyl and the like. Alkenyl groups may be substituted or unsubstituted. Substituents may also be themselves substituted. When substituted, the substituent group is preferably alkyl, halogen, or alkoxy. Substituents may also be themselves substituted. Substituents be placed on the alkene itself and also on the adjacent member atoms or the alkynyl moiety "$C_2$-$C_4$ alkenyl" refers to alkenyl groups containing two to four carbon atoms. "Alkenylene" means a divalent alkenyl group.

"Alkynyl" refers to an unsaturated aliphatic hydrocarbon moiety including straight chain and branched chain groups. Alkynyl moieties must contain at least one alkyne. "Alkynyl" may be exemplified by groups such as ethynyl, propynyl, n-butynyl and the like. Alkynyl groups may be substituted or unsubstituted. When substituted, the substituent group is preferably alkyl, amino, cyano, halogen, alkoxyl or hydroxyl. Substituents may also be themselves substituted. Substituents are not on the alkyne itself but on the adjacent member atoms of the alkynyl moiety. "$C_2$-$C_4$ alkynyl" refers to alkynyl groups containing two to four carbon atoms. "Alkynylene" means a divalent alkynyl group.

"Acyl" or "carbonyl" refers to the group —C(O)R wherein R is alkyl; alkenyl; alkyl alkynyl, aryl, heteroaryl, carbocyclic, heterocarbocyclic; $C_1$-$C_4$ alkyl aryl or $C_1$-$C_4$ alkyl heteroaryl. $C_1$-$C_4$ alkylcarbonyl refers to a group wherein the carbonyl moiety is preceded by an alkyl chain of 1-4 carbon atoms.

"Alkoxy" refers to the group —O—R wherein R is acyl, alkyl alkenyl, alkyl alkynyl, aryl, carbocyclic; heterocarbocyclic; heteroaryl, $C_1$-$C_4$ alkyl aryl or $C_1$-$C_4$ alkyl heteroaryl "Amino" refers to the group —NR'R' wherein each R' is, independently, hydrogen, alkyl, aryl, heteroaryl, $C_1$-$C_4$ alkyl aryl or $C_1$-$C_4$ alkyl heteroaryl. The two R' groups may themselves be linked to form a ring.

"Aryl" refers to an aromatic carbocyclic group. "Aryl" may be exemplified by phenyl. The aryl group may be substituted or unsubstituted. Substituents may also be themselves substituted. When substituted, the substituent group is preferably but not limited to heteroaryl; acyl, carboxyl, carbonylamino, nitro, amino, cyano, halogen, or hydroxyl. "Arylene" means a divalent aryl group.

"Azidylene" refers to a divalent moiety with an azide functional group.

"Carboxyl" refers to the group —C(=O)O—$C_1$-$C_4$ alkyl.

"Carbonylamino" refers to the group —C(O)NR'R' wherein each R' is, independently, hydrogen, alkyl, aryl, cycloalkyl; heterocycloalkyl; heteroaryl, $C_1$-$C_4$ alkyl aryl or $C_1$-$C_4$ alkyl heteroaryl. The two R' groups may themselves be linked to form a ring.

"$C_1$-$C_4$ alkyl aryl" refers to $C_1$-$C_4$ alkyl groups having an aryl substituent such that the aryl substituent is bonded through an alkyl group. "$C_1$-$C_4$ alkyl aryl" may be exemplified by benzyl.

"$C_1$-$C_4$ alkyl heteroaryl" refers to $C_1$-$C_4$ alkyl groups having a heteroaryl substituent such that the heteroaryl substituent is bonded through an alkyl group.

"Carbocyclic group" or "cycloalkyl" means a monovalent saturated or unsaturated hydrocarbon ring. Carbocyclic groups are monocyclic, or are fused, spiro, or bridged bicyclic ring systems. Monocyclic carbocyclic groups contain 3 to 10 carbon atoms, preferably 4 to 7 carbon atoms, and more preferably 5 to 6 carbon atoms in the ring. Bicyclic carbocyclic groups contain 8 to 12 carbon atoms, preferably 9 to 10 carbon atoms in the ring. Carbocyclic groups may be substituted or unsubstituted. Substituents may also be themselves substituted. Preferred carbocyclic groups include cyclopropyl, cyclobutyl, cyclopentyl, cyclohexyl, cyclohexenyl, and cycloheptyl. More preferred carbocyclic groups include cyclopropyl and cyclobutyl. The most preferred carbocyclic group is cyclopropyl. Carbocyclic groups are not aromatic. "Cycloalkylene" means a divalent cycloalkyl group.

"Halogen" refers to fluoro, chloro, bromo or iodo moieties.

"Heteroalkyl" or "heteroalkenyl" or "heteroalkynyl" mean an alkyl, alkenyl, or alkynyl, respectively, having one or more heteroatoms. Heteroalkyl may be substituted or unsubstituted. When substituted, the substituents may themselves be substituted. Preferred but non limiting substituents are aryl; $C_1$-$C_4$ alkylaryl; amino; halogen, hydroxy, cyano, nitro; carboxyl; carbonylamino or $C_1$-$C_4$ alkyl. "Heteroalkylene" or "heteroalkenylene" or "heteroalkynylene" mean a divalent heteroalkyl or heteroalkenyl or heteroalkynyl group, respectively.

"Heteroaryl" or "heteroaromatic" refers to a monocyclic or bicyclic aromatic carbocyclic radical having one or more heteroatoms in the carbocyclic ring. Heteroaryl may be substituted or unsubstituted. When substituted, the substituents may themselves be substituted. Preferred but non limiting substituents are aryl; $C_1$-$C_4$ alkylaryl; amino; halogen, hydroxy, cyano, nitro; carboxyl; carbonylamino or $C_1$-$C_4$ alkyl. Preferred heteroaromatic groups include tetrazoyl, triazolyl; thienyl, thiazolyl, purinyl, pyrimidyl, pyridyl, and furanyl. More preferred heteroaromatic groups include benzothiofuranyl; thienyl, furanyl, tetrazoyl, triazolyl; and pyridyl. "Heteroarylene" means a divalent heteroaryl group.

"Heteroatom" means an atom other than carbon in the ring of a heterocyclic group or a heteroaromatic group or the chain of a heterogeneous group. Preferably, heteroatoms are selected from the group consisting of nitrogen, sulfur, and oxygen atoms. Groups containing more than one heteroatom may contain different heteroatoms.

"Heterocarbocyclic group" or "heterocycloalkyl" or "heterocyclic" means a monovalent saturated or unsaturated hydrocarbon ring containing at least one heteroatom. Heterocarbocyclic groups are monocyclic, or are fused, spiro, or bridged bicyclic ring systems. Monocyclic heterocarbocyclic groups contain 3 to 10 carbon atoms, preferably 4 to 7 carbon atoms, and more preferably 5 to 6 carbon atoms in the ring. Bicyclic heterocarbocyclic groups contain 8 to 12 carbon atoms, preferably 9 to 10 carbon atoms in the ring. Heterocarbocyclic groups may be substituted or unsubstituted. Substituents may also be themselves substituted. Preferred heterocarbocyclic groups include epoxy, tetrahydrofuranyl, azacyclopentyl, azacyclohexyl, piperidyl, and homopiperidyl. More preferred heterocarbocyclic groups include piperidyl, and homopiperidyl. The most preferred heterocarbocyclic group is piperidyl. Heterocarbocyclic groups are not aromatic. "Heterocycloalkylene" means a divalent heterocycloalkyl group.

"Heterogeneous group" means a divalent group that contains up to 10 member atoms. A "heterogeneous group" may be saturated or unsaturated and may contain rings. One suitable heterogenous group is

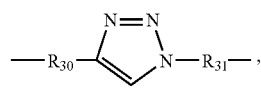

wherein $R_{30}$ and $R_{31}$ are independently selected from alkylene, heteroalkylene, alkenylene, heteroalkenylene, alkynylene or heteroalkynylene.

"Hydroxy" or "hydroxyl" means a chemical entity that consists of —OH. Alcohols contain hydroxy groups. Hydroxy groups may be free or protected. An alternative name for hydroxyl is hydroxy.

"Member atom" means a carbon, nitrogen, oxygen or sulfur atom. Member atoms may be substituted up to their normal valence. If substitution is not specified the substituents required for valency are hydrogen.

"Multi-valent Center" means a monovalent, divalent, trivalent, or tetravalent moiety. Suitable divalent moieties include alkylene, heteroalkylene, alkenylenE, heteroalkenylene, alkynylene, heteroalkynylene, arylene, heteroarylene, arylalkylene, arylheteroalkylene, heteroarylalkylene, heteroarylheteroalkylene, arylalkenylene, arylheteroalkenylene, heteroarylalkenylene, heteroarylheteroalkenylene, arylalkynylene, arylheteroalkynylene, heteroarylalkynylene, heteroarylheteroalkynylene, cycloalkylene, and heterocycloalkylene. Suitable monovalent, trivalent and tetravalent moieties are based on the above.

"Ring" means a collection of member atoms that are cyclic. Rings may be carbocyclic, aromatic, or heterocyclic or heteroaromatic, and may be substituted or unsubstituted, and may be saturated or unsaturated. Ring junctions with the main chain may be fused or spirocyclic. Rings may be monocyclic or bicyclic. Rings contain at least 3 member atoms and at most 10 member atoms. Monocyclic rings may contain 3 to 7 member atoms and bicyclic rings may contain from 8 to 12 member atoms. Bicyclic rings themselves may be fused or spirocyclic.

"Thioalkyl" refers to the group —S-alkyl.

"Sulfonyl" refers to the —S(O)$_2$R' group wherein R' is alkoxy, alkyl, aryl, carbocyclic, heterocarbocyclic; heteroaryl, $C_1$-$C_4$ alkyl aryl or $C_1$-$C_4$ alkyl heteroaryl.

"Sulfonylamino" refers to the —S(O)$_2$NR'R' group wherein each R' is independently alkyl, aryl, heteroaryl, $C_1$-$C_4$ alkyl aryl or $C_1$-$C_4$ alkyl heteroaryl.

"Tosylene" refers to a divalent moiety with a tosylate functional group.

Compounds

In some embodiments, the compounds of the invention have the General Formula I:

wherein X is multi-valent center;
Y is selected from the group consisting of N and C;

n is 2, if Y is N; and n is 3, if Y is C;
m is 1 to 4;
R is selected from the group consisting of hydrogen and a moiety according to General Formula II:

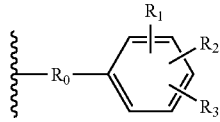

(II)

wherein $R_0$ is selected from the group consisting of a direct bond, alkylene, alkenylene, alkynylene, heteroalkylene, heteroalkenylene, heteroalkynylene, azidylene, —$NR_{32}$—, and heterogenous groups; $R_{32}$ is independently selected from the group consisting of hydrogen, alkyl, alkenyl, alkynyl, heteroalkyl, heteroalkenyl, heteroalkynyl, aryl, heteroaryl, cycloalkyl and heterocycloalkyl; and $R_1$, $R_2$, and $R_3$ are independently selected from the group consisting of hydrogen, halo, —$R_4$, and —O—$R_4$, wherein $R_4$ is selected from the group consisting of hydrogen, alkyl, alkylamino, heteroalkyl, hydroxyalkyl, alkylazide, alkenyl, and —$R_6$—N($R_7$)($R_8$). In General Formula II, at least one of $R_1$, $R_2$, and $R_3$ is —OH. $R_6$ is selected from the group consisting of alkylene, alkenylene, alkynylene, heteroalkylene, heteroalkenylene, heteroalkynylene, azidylene, and heterogenous groups; and $R_7$ and $R_8$ are independently selected from the group consisting of hydrogen and —A. A is according to General Formula III:

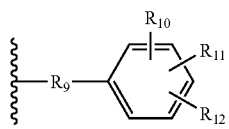

(III)

wherein $R_9$ is selected from the group consisting of a direct bond, alkylene, alkenylene, alkynylene, heteroalkylene, heteroalkenylene, heteroalkynylene, azidylene, —$NR_{32}$—, and heterogenous groups; $R_{32}$ is independently selected from the group consisting of hydrogen, alkyl, alkenyl, alkynyl, heteroalkyl, heteroalkenyl, heteroalkynyl, aryl, heteroaryl, cycloalkyl and heterocycloalkyl; and $R_{10}$, $R_{11}$, and $R_{12}$ are independently selected from the group consisting of hydrogen, halo, —$R_{13}$, and —O—$R_{13}$, wherein $R_{13}$ is selected from the group consisting of hydrogen, alkyl, alkylamino, heteroalkyl, hydroxyalkyl, alkylazide, alkenyl, and —$R_{14}$—N($R_{15}$)($R_{16}$); and at least one of $R_{10}$, $R_{11}$, and $R_{12}$ is —OH; $R_{14}$ is selected from the group consisting of alkylene, alkenylene, alkynylene, heteroalkylene, heteroalkenylene, heteroalkynylene, azidylene, and heterogenous groups; and $R_{15}$ and $R_{16}$ are independently selected from the group consisting of hydrogen and —B. B is according to General Formula IV:

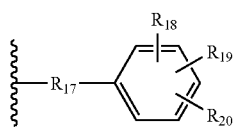

(IV)

wherein $R_{17}$ is selected from the group consisting of a direct bond, alkylene, alkenylene, alkynylene, heteroalkylene, heteroalkenylene, heteroalkynylene, azidylene, —$NR_{32}$—, and heterogenous groups; $R_{32}$ is independently selected from the group consisting of hydrogen, alkyl, alkenyl, alkynyl, heteroalkyl, heteroalkenyl, heteroalkynyl, aryl, heteroaryl, cycloalkyl and heterocycloalkyl; and $R_{18}$, $R_{19}$, and $R_{20}$ are independently selected from the group consisting of hydrogen, halo, —$R_{21}$, and —O—$R_{21}$, wherein $R_{21}$ is selected from the group consisting of hydrogen, alkyl, alkylamino, heteroalkyl, hydroxyalkyl, alkylazide, and alkenyl; and at least one of $R_{18}$, $R_{19}$, and $R_{20}$ is —OH.

$R_{32}$ is independently selected from the group consisting of hydrogen, alkyl, alkenyl, alkynyl, heteroalkyl, heteroalkenyl, heteroalkynyl, aryl, heteroaryl, cycloalkyl, and heterocycloalkyl.

Suitable substituents include, but are not limited to, halogen, hydroxyl, alkoxy, alkyl, alkenyl, alkynyl, cycloalkyl, heterocycloalkyl, amino, amide, nitro, keto, oxo, carboxylic acid, carboxyl, aryl, heteroaryl, thiol, thioalkyl, thioester, disulfide, phosphine, carbonyl, carbonylamino, formyl, sulfonyl, sulfonylamino, cyano, isocyano, $C_{1-4}$ alkyl aryl and $C_{1-4}$ alkyl heteroaryl.

In certain embodiments, X is selected from the group consisting of

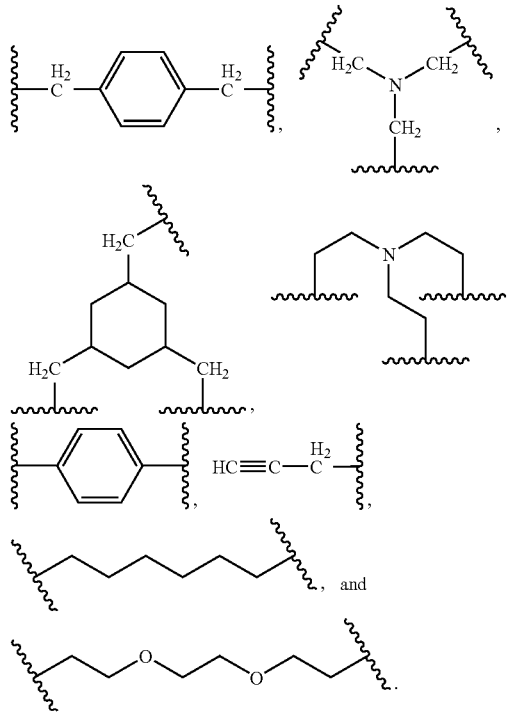

In certain embodiments, X is

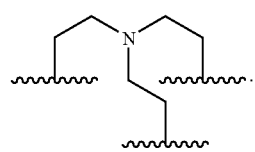 [SMILES: *CCN(CC*)CC*]

In certain embodiments, X is

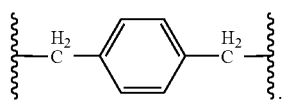

In certain embodiments, Y is N and R is according to Formula II. In certain embodiments, $R_0$ is methylene.

In certain embodiments wherein R is according to Formula II, at least one of $R_1$, $R_2$, and $R_3$ is —$R_6$—N($R_7$)($R_8$) or —O—R₆—N(R₇)(R₈). In certain embodiments, wherein R is according to Formula II at least one of $R_1$, $R_2$, or $R_3$ is —O—R₄ wherein R₄ is alkylamino, alkyl, or H. In certain embodiments wherein R is according to Formula II, at least one of $R_1$, $R_2$, or $R_3$ is —O—R₄ wherein R₄ is H or methyl.

In certain embodiments, at least one of $R_{10}$, $R_{11}$, and $R_{12}$ is —R₁₄—N(R₁₅)(R₁₆) or —O—R₁₄—N(R₁₅)(R₁₆). In certain embodiments, at least one of $R_{10}$, $R_{11}$, or $R_{12}$ is —O—R₁₃ wherein R₁₃ is alkylamino.

In certain embodiments, at least one of $R_{18}$, $R_{19}$, and $R_{20}$ is —O—R₂₁ wherein R₂₁ is alkylamino.

In certain embodiments, X is

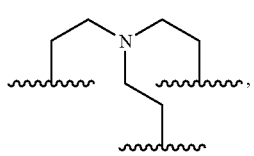

wherein the compound may have reduced pro-oxidant effects, as described further below. For example the compound may have reduced pro-oxidant effects relative to the antioxidants Trolox and quercetin. Pro-oxidant effects may be determined as described in the examples and any methods known in the art.

In certain embodiments, the compounds may be selected from the following:

Compound 1

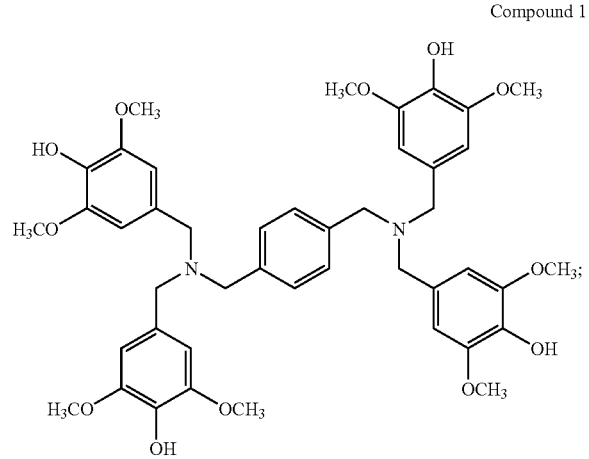

Compound 2

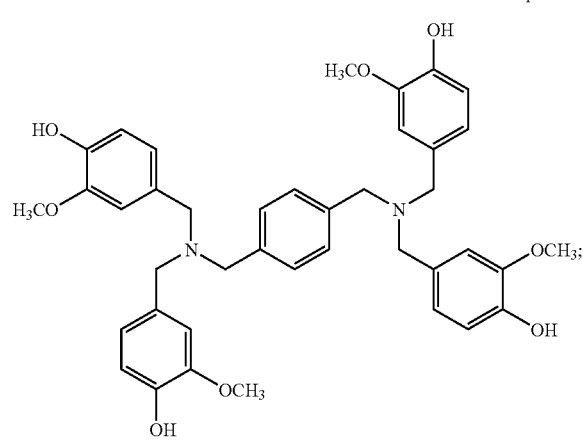

Compound 3

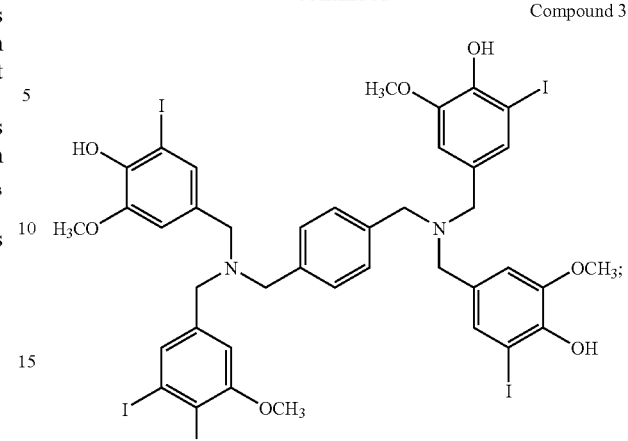

Compound 4

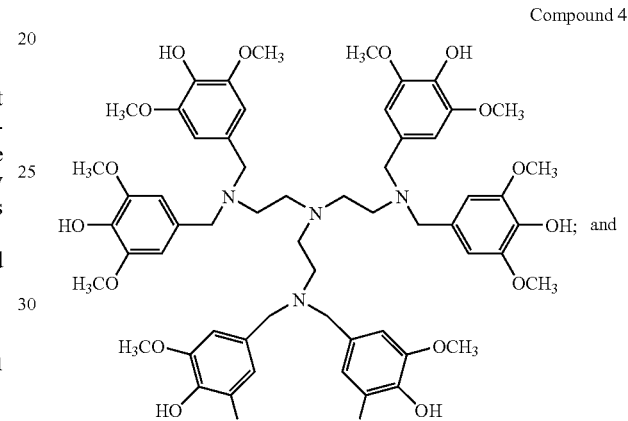

Compound 5

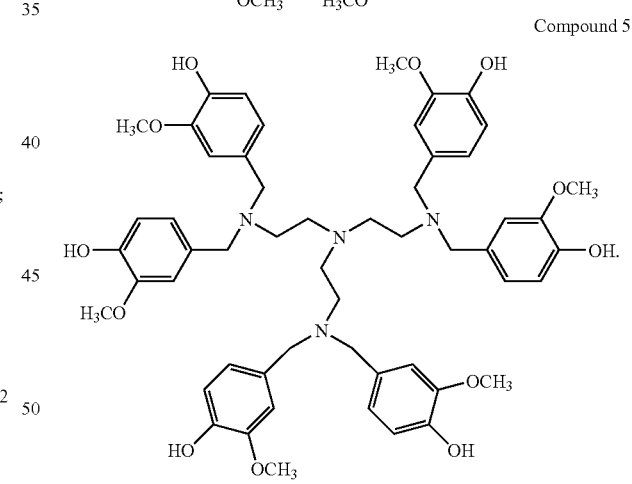

In other embodiments of the invention, one or more active agents may be attached to the dendritic compound. The active agents may be non-covalently or covalently attached to the dendrimer termini, branches, or a combination thereof. For example, active agents may be attached to the dendrimer via ester bonds, which may be hydrolyzed under physiological conditions to release the active agents. Further, release of the active agents from the dendrimer may be enhanced in cancer cells because cancer cells have slightly acidic pH. Release profiles of active agents from dendrimers may be examined using methods known by those of skill in the art, including equilibrium dialysis. Active agents may be covalently attached to the dendrimer compounds via a linker. The linker may be a hydrocarbon chain, branched or unbranched, saturated or unsaturated, substituted or unsubstituted, and may comprise heteroatoms. The linker may include, but are not limited to, alkylene, heteroalkylene, alkenylene, heteroalkenylene, alkynylene, heteroalkynylene, arylene, heteroarylene, —$NR_{32}$—, —$C(O)NR_{32}$—, —$C(O)O$—, azidylene, —$C(O)$—, and heterogenous groups. In some embodiments, an active agent may be covalently attached to the compound, for example, through an amide or amine linkage, at $R_4$ or $R_{13}$ or $R_{21}$ in the general formula above.

Active agents may include one or more pharmaceutically active agents. Pharmaceutically active agents may include antibiotics, analgesics (e.g. morphine, codeine, aspirin, acetominaphen, ibuprofen, etc.), anti-inflammatory agents (e.g. cyclooxygenase inhibitors, NOS inhibitors, NADPH oxidase inhibitors, etc.), cancer therapeutics or chemotherapeutics (e.g. raloxifen, docetaxel, bicalutamide, gleevac, cisplatin, taxol, vincristine, doxorubicin, cyclophosphamide, statins, melphalan, fludarabine, camptotechins, monoclonal and polyclonal antibodies against VEG, VEGFr, EGF, ERGFr, etc.), cardiovascular drugs or atherosclerosis agents (e.g. statins such as lovastatin, niacin, etc.), asthma therapeutics (e.g. steroids such as prednisolone, etc.), hormones, and combinations thereof. Cancer therapeutics may include therapeutics for treating any cancer, including, but not limited to, breast, prostate, kidney, and lung cancers as well as lymphomas.

Active agents may also include cell-targeting agents. As appreciated by those of skill in the art, cell targeting agents may include compounds that direct the compounds to a site in a cell, a particular cell, a particular organ, tissue, or other area. Cell-targeting agents may target a cell or process. Cell-targeting agents are known by those of skill in the art and may include antibodies, polypeptides, and polysaccharides.

Active agents may also include imaging agents. As appreciated by those of skill in the art, imaging agents may include compounds that may target a cell or process and permit detection. Imaging agents may include, for example, those known by one of skill in the art such as fluorescent molecules, heavy atoms, gadolinium, far infra-red dyes, radioisotopes, and nanoparticles.

The compounds disclosed herein may have antioxidant function at both the dendrimer branches and termini. For example, the branches may have phenolic hydroxyl groups and benzylic hydrogens to serve as electron donating functional groups as well as free radical scavenging sites. The compounds disclosed herein may have a defined molecular weight such as from about 500 Da to about 100 kDa. It is envisioned that the molecule weights of the compounds disclosed herein may result in longer in vivo half-life and decreased excretion rate compared to antioxidants of lower molecular weight. The compounds may be amphiphilic and thus have the ability to access to both aqueous (extracellular and intracellular space) and lipophilic (lipophilic cell membrane and lipoprotein) compartments. The compounds have branches that may yield intramolecular regions with various microenvironments. For example, the surface of the compound may be easier to access than that interior of the compound, which may lead to differential activity and stability of different regions of the compound.

The compounds may chelate metal ions as well as scavenge free radicals. Binding of metal ions may occur with tertiary amines locates at the core of the dendrimer compounds. Metal ions may include, but are not limited to, cobalt, nickel, copper, iron, lanthanides, and actinides.

The antioxidant activity of the compounds of the invention may be tested or examined by any suitable method, including a variety of methods known to one of skill in the art. For example, the antioxidant activity may be determined by electron spin resonance, or a 2,2'-azinobis-(3-ethylbenzothiazoline-6-sulfonic acid) (ABTS) radical cation decolorization assay. As another example, the capacity of the compounds of the invention to protect biomolecules (e.g. DNA, protein, lipid, red blood cells, etc.) from free radical damage may be assessed in vitro in a free radical generation system using 2,2'-azobis(2-amidinopropane)dihydrochloride (AAPH) or 2,2'-azobis(2,4-dimethylvaleronitrile) as hydrophilic initiators. As shown in the Examples, the antioxidant activity may be evaluated using methods including but not limited to a the 1,1-diphenyl-2-picrylhydrazyl (DPPH) radical assay, ABTS radical decolorization assay, FRAP assay, or enzyme inactivation assays.

Chemical Synthesis

Compounds according to the invention may be synthesized by any suitable methods. For example, the dendritic nano-antioxidants may be synthesized according to the general schemes described below and in the Examples. In general, a core molecule is reacted with a branching unit (BU). Molecules may be used as building blocks (BB) added to the core to form a G1 dendrimer. Building blocks may include but are not limited to natural antioxidants such as syringaldehyde, vanillin, and gallic acid. Additional branching units and building blocks may be attached to form G1 dendrimers and G2 dendrimers, with the reactive steps repeated to form a dendritic tree-like structure.

An antioxidant dendrimer may be generally synthesized according to FIG. 1. Compound 35 was converted to its alcohol derivative (36) by using $LiAlH_4$. The alcohol group of compound 36 was oxidized to its aldehyde derivative using pyridinium chlorochromate (PCC) by a previously reported method (Corey et al. *Tetrahedron Lett.* 1975, 16, 2647-2650, incorporated herein by reference in its entirety). The methoxy groups of compound 36 were cleaved using $BBr_3$ (37). The compounds may be prepared in high yields. Two hydroxyl groups of compound 37 may be protected with silyl protecting group (e.g. TESOTf, or TeocC1) to form 38 to avoid self-scrambling between Br and OH group in the following Buchwald reaction (Wolter et al. *Org. Lett.* 2002, 4, 973-976, incorporated herein by reference in its entirety). Compound 38 may be attached to a branching unit to form 39 using CuI, 1,10-phenanthroline, and cesium carbonate as catalysts (Wolter et al. *Org. Lett.* 2002, 4, 973-976, incorporated herein by reference in its entirety). The aldehyde group may not need to be protected because it is not affected under similar conditions (Sonogashira reaction using 4-bromobenzaldehyde as a substrate) (Egbe et al. *Macromolecules* 2003, 36, 5459-5469; Dudek et al. *J. Am. Chem. Soc.* 2001, 123, 8033-8038; Echavarren et al. *J. Am. Chem. Soc.* 1987, 109, 5478-5486; Sad et al. *J. Org. Chem.* 1992, 57, 678-685, incorporated herein by reference in their entireties). The synthesized building block 39 may be attached to the p-xylylendiamine (core) to form 40 using $Na(OAc)_3BH$. $Na(OAc)_3BH$ may be highly effective and stable in the presence of free phenolic OH groups (e.g. G1 and G2 synthesis in FIG. 8). Thus, the reductive amination in the dendrimer synthesis may be carried out without protecting the OH groups and the percent yield would not be affected even though TES group becomes cleaved by the water by-products from the reductive amination reaction. If $Na(OAc)_3BH$ becomes consumed by the phenolic hydroxyl groups or the compounds do not dissolve in organic solvent, one may use $NaCNBH_3$ which can be used in slightly acidic (~pH 4) aqueous environment. Phthalimide may be removed using hydrazine (Bernhard et al. *J. Org. Chem.* 1977, 42, 1093-1095, incorporated herein by reference in its entirety) or NaBH$_4$/2-propanol/AcOH (Osby et al. *Tetrahedron Lett.* 1984, 25, 2093-2096, incorporated herein by reference in its entirety) to expose four amino ends to form G1, 41. To the amine ends, 8 equivalents of building block 39 may be attached (42), followed by phthalimide removal to yield G2 (43). The steps, g and h, may be repeated as desired. Once the dendrimer is made, drug molecules (bicalutamide or docetaxel) may be attached to its amino ends, as depicted in FIG. 1. Drug molecules may be coupled to a linker containing an N-hydroxysuccinimide ester (NHS) on one end and an aldehyde at the other end. The OH group of bicalutamide may react with the NHS side of the linker to form an ester bond. In case of docetaxel, one of its three OH groups may be coupled to the same linker. Even though the linker may be attached to a different OH group, the biological activity of this nano-drug may not be affected. The aldehyde group of drug-linker conjugate may be reacted with amine termini via reductive amination. The number of drug molecules per dendrimer may be determined using spectroscopic methods and mass spectrometry.

Figure 3:
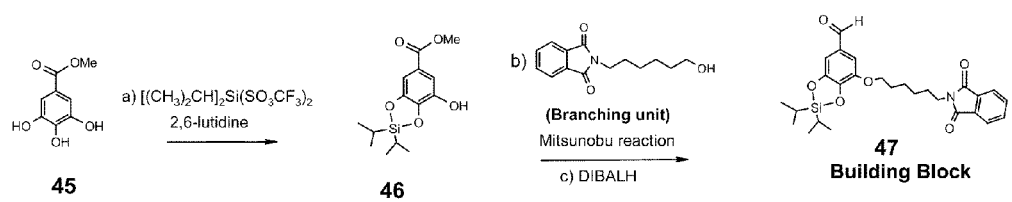
FIG. 3 is a scheme for the synthesis of the building block 47.
Figure 4:
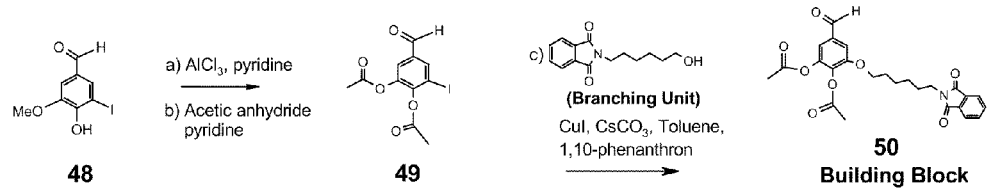
FIG. 4 is a scheme for the synthesis of the building block 50.
Figure 5:
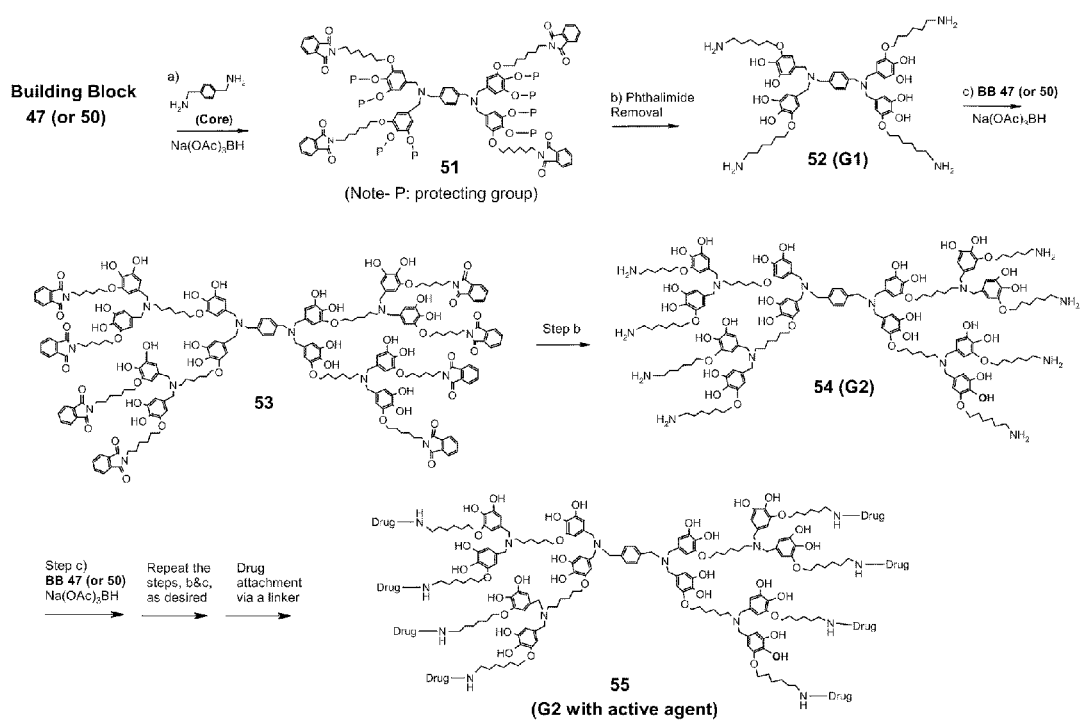
FIG. 5 is a scheme for the synthesis of a G1 antioxidant dendrimer 52, a G2 antioxidant dendrimer 54, and a G2 antioxidant dendrimer with active agent 55.

An antioxidant dendrimer may also be generally synthesized according to FIGS. 3-5, for example, using methyl gallate (45), a naturally available AO with 3,4,5-tri-hydroxyl groups. One of three OH groups may be used to attach branching unit and the leftover OH groups for radical scavenging. Hence, use of a protecting group that can bridge two of the OH groups may be beneficial. Towards this end, diisopropylsilyl bis(trifluoromethanesulfonate) in the presence of 2,6-lutidine may be used to form a cyclic silyl derivative, 20 (FIG. 3) (Corey et al. *Tetrahedron Lett.* 1990, 31, 601-604, incorporated herein by reference in its entirety). Once the OH groups are protected, the leftover OH group may be reacted with the branching unit, followed by reduction of the methylester to an aldehyde using DIBALH to yield building block, 47. An alternative route to make the same building block is shown in FIG. 4 in which compound 48 is demethylated by using AlCl$_3$ and pyridine (Zouhiri et al. *J. Med. Chem.* 2000, 43, 1533-1540, incorporated herein by reference in its entirety). The resulting intermediate may be protected with acetic anhydride to form 49 (the protecting group can be changed if necessary). The branching unit may be attached to 49 to generate building block 50, using CuI, 1,10-phenanthroline, and cesium carbonate catalysts. The dendrimer may be generated by the same procedures followed for the dendrimer described above for FIG. 1 except for using building block 47 or 50 (FIG. 5). Four equivalents of 47 (or 50) and Na(OAc)$_3$BH may be treated with the core unit (p-xylylenediamine) to produce 51, followed by phthalimide removal using hydrazine or NaBH$_4$/2-propanol/AcOH with concomitant cleavage of the protecting groups, acetyl (or cyclic silyl) groups. The attachment of the building block (step c) and removal of phthalimide (step b) can be repeated as desired. Then, drug molecules may be attached to the amine ends of the final dendrimer using the aforementioned method.

Figure 6:
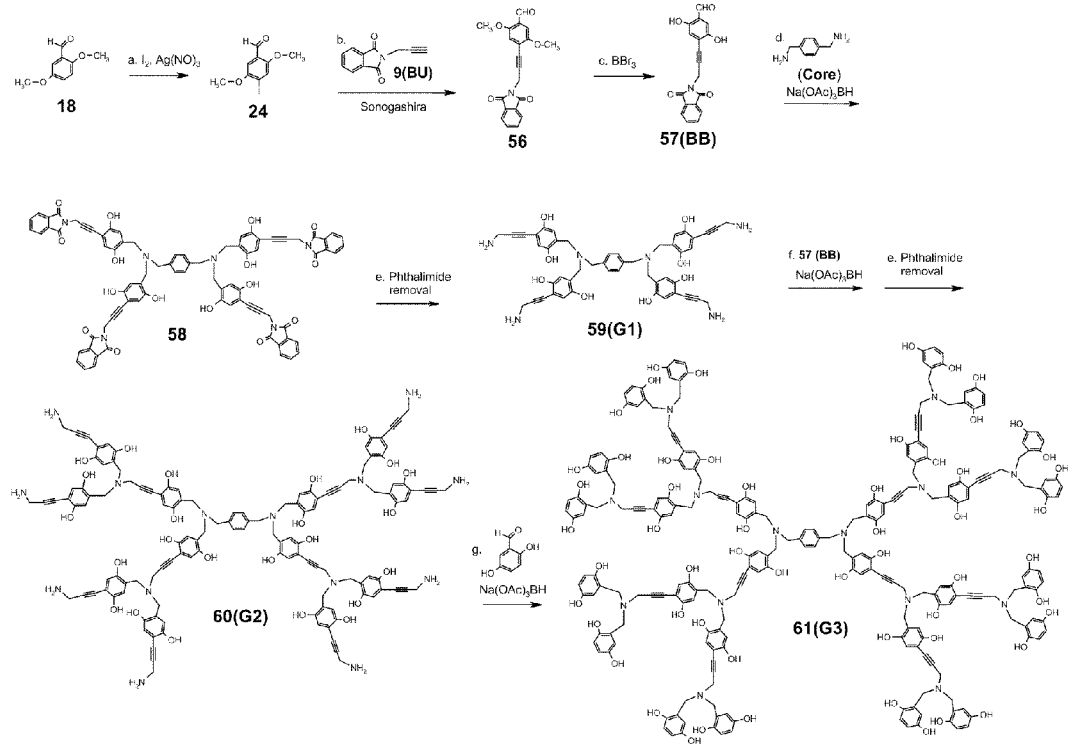
FIG. 6 is a scheme for the synthesis of a building block 57, a G1 antioxidant dendrimer 59, a G2 antioxidant dendrimer 60, and a G3 antioxidant dendrimer 61.

Compounds according to the invention may be synthesized as generally shown in FIG. 6. Commercially available 2,5-dimethoxybenzaldehyde (18) may be converted to its iodo derivative (24) by reaction with I$_2$ and Ag(NO)$_3$ (as described for FIG. 7). Compound 24 possesses two methoxy groups and one iodo group on the phenyl ring. The iodo group may be used to attach the branching unit and demethylate the two methoxy groups to expose two phenolic OH groups so that the OH groups may scavenge radicals by donating their hydrogen atoms to free radicals in apolar media and by transferring electrons in polar media. The branching unit may function to extend conjugation as well as serve as a branching point.

Compound 24 may be attached to a branching unit (9), N-phthalimide protected propargylamine, to form 56 using the Sonogashire reaction.

The compound 56 may be demethylated using BBr$_3$ to generate building block 57. The aldehyde group may not need to be protected because it is not affected under many similar Sonogashira reactions (using brominated or iodinated benzaldehyde as a substrate). The aldehyde group and triple bond may be stable under BBr$_3$ reaction conditions. Four equivalents of the synthesized building block 57 may be attached to one equivalent of the core unit (4-aminomethylbenzylamine) to form 58 using Na(OAc)$_3$BH. Na(OAc)$_3$BH is effective and stable in the presence of free phenolic OH groups (e.g. G1 synthesis in FIG. 8). Thus, the reductive amination in the proposed dendrimer synthesis may be carried out without protecting the OH groups. In the event that Na(OAc)$_3$BH becomes consumed by the hydroxyl groups or the dendrimer does not dissolve in organic solvent, NaCNBH$_3$ may be used as an alternative. NaCNBH$_3$ may be used in acidic (~pH 4) aqueous environments. Alternatively, the hydroxyl groups of building block 57 may be protected with silyl groups, such as triethylsilytriflate (TES-OTf) or tert-butyldimethylsilyl (TB-DMS) chloride, and the reaction run in the presence of molecular sieves. The silyl group may help dissolute the building block 57 and product (58) in the reaction solvent but it may be hydrolyzed by water by-products from reductive amination reaction. Phthalimide groups of 58 may be removed using hydrazine or NaBH$_4$/2-propanol/AcOH to expose four amino ends (59, G1) to which eight equivalents of building block 57 may be attached, followed by phthalimide removal to form G2 (60). The steps, e and f, may be repeated as desired. Once the dendrimer has reached a desirable size, dendrimer growth may be terminated by attaching a building block without a branching unit attached. An example is depicted (step g, FIG. 6) using G2 dendrimer (60) to make G3 (61) as a final generation.

The amino terminal can be used to attach active agents, including but not limited to, therapeutic molecules, antibodies, and imaging agents after further modification of the amino terminals with diethylene triamine pentaacetic acid (DTPA) or ethylene diamine tetraacetic acid (EDTA). In such applications, the proposed dendrimer may have an interior with a radical absorbing function and termini (surface) with reactive functional groups (amines) for attachment of various active agents, as described above.

Figure 9:
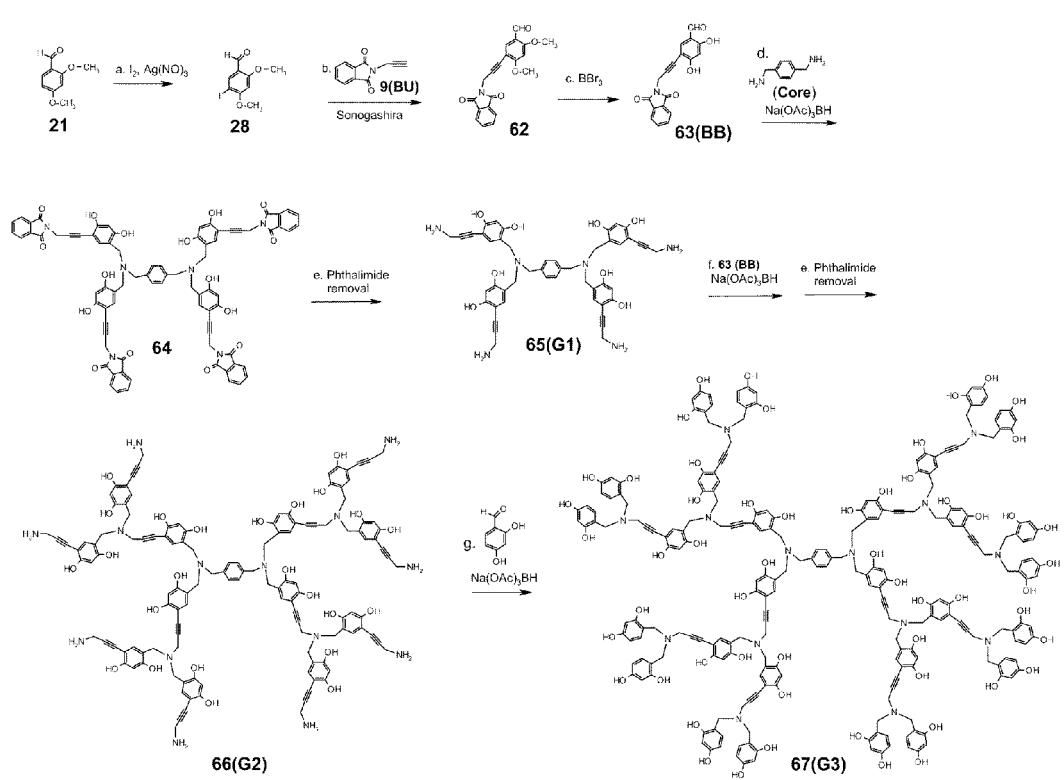
FIG. 9 is a scheme for the synthesis of a building block 63, a G1 antioxidant dendrimer 65, a G2 antioxidant dendrimer 66, and a G3 antioxidant dendrimer 67.

Compounds according to the invention may be synthesized as generally shown in FIG. 9, using a similar method as shown in FIG. 6 except for using 2,4-dimethoxybenzaldehyde (21) as a starting material in place of the 2,5-dimethoxybenzaldehyde. As shown in FIG. 9, G1 (65), G2 (66), and G2 (67) may be synthesized from starting material 21.

Figure 10:
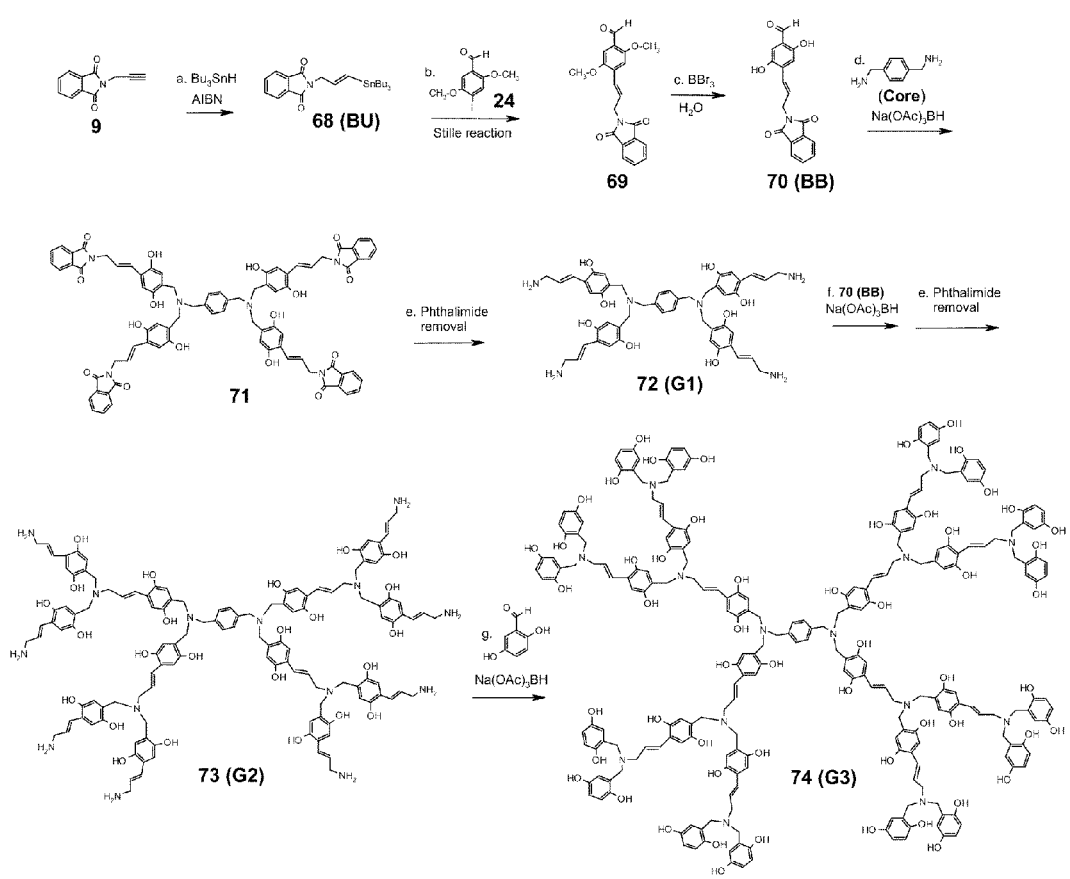
FIG. 10 is a scheme for the synthesis of a building block 70, a G1 antioxidant dendrimer 72, a G2 antioxidant dendrimer 73, and a G3 antioxidant dendrimer 74.

The general synthetic methods shown in FIGS. 6 and 9 may be modified to generate their congener dendrimers. The dendrimers shown in FIG. 10 are congeners of the dendrimers shown in FIG. 6, differing only by the type of conjugation (the branching unit may be attached to the building block via a double bond instead of triple bond). The compound 9 may be stannylated using Bu$_3$SnH and azobisisobutyronitrile (AIBN) as a radical initiator to generate compound 68. The reaction may generate E and Z mixture, with E as the major product in the reaction run at high (for example, approximately 90° C.) temperature. The E isomer may be isolated and used in the dendrimer synthesis. The E isomer (68) may be attached to 24 to yield compound 69 using the Stille reaction in which palladium catalysts (e.g. Pd(Cl$_2$(PPh$_3$)$_4$), Pd(OAc)$_2$, and Pd(PPh$_3$)$_4$) and CuI may be used as reagents. Aldehyde group of 24 may not be affected under these conditions.

Subsequently, compound 69 may be demethylated with BBr$_3$ to generate building block 70. Four equivalents of building block 70 may be treated with one equivalent of the core (4-aminomethylbenzylamine) to form 71 with 8 hydroxyl groups. Alternatively, the OH groups may be protected with TES-OTf or TBDMS-Cl, with the reductive amination reaction run in the presence of molecular sieves. Subsequently, phthalimide groups of 71 may be removed using hydrazine or NaBH$_4$/2-propanol/AcOH to form G1 (72). Steps e and f can be repeated as desired. Once the dendrimer is a desirable size, dendrimer growth may be terminated by attaching building blocks without branching unit attached. An example is depicted (step g, FIG. 10) using G2 dendrimer (73) to make G3 (74) as a final generation. The G2 dendrimer shown in FIG. 10 carries 56 hydroxyl groups. Dendrimers corresponding to the dendrimers shown in FIG. 9 may be synthesized by the same methods shown in FIG. 10, using 5-iodo-2,4-dimethoxybenzaldehyde as a starting material instead of 4-iodo-2,5-dimethoxybenzaldehyde. The synthesized dendrimers including intermediates may be purified using any suitable methods including methods known by those of skill in the art such as ultra-filtration membranes, flash chromatography, and prep-HPLC. The dendrimer structures may be determined using any suitable methods including methods known by those of skill in the art such as by $^1$H/$^{13}$C-NMR, FT-IR, and MALDI-TOF/ESI.

Figure 11A:
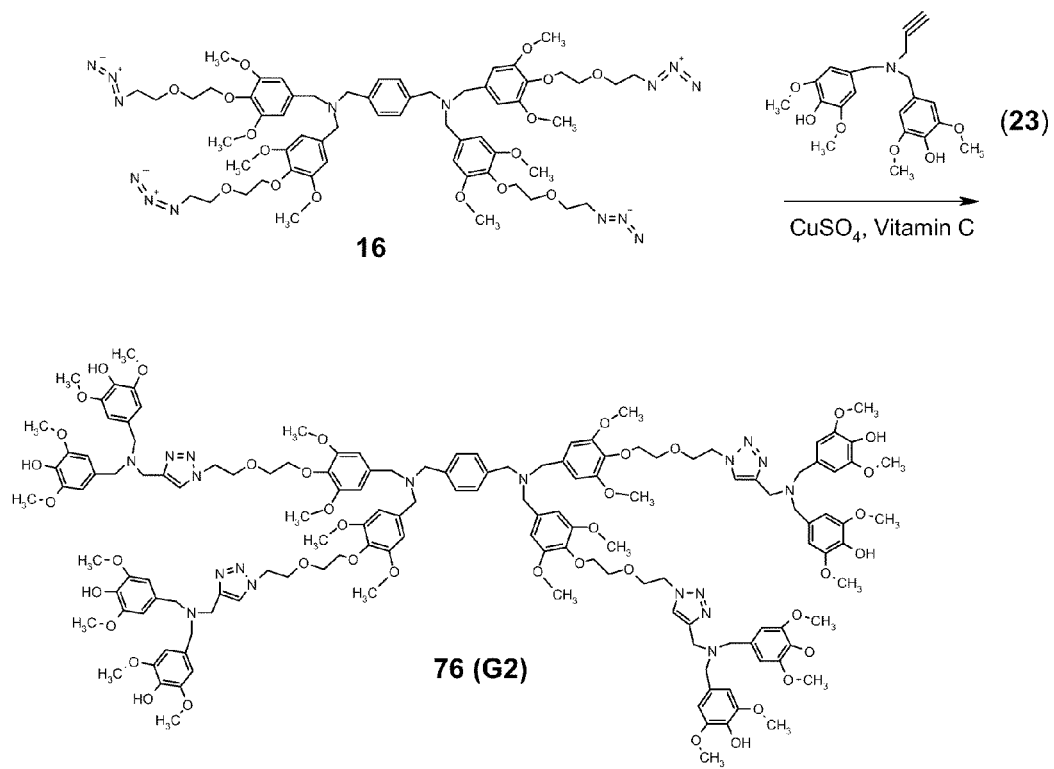
FIGS. 11A, 11B and 11C are schemes for using azide and ethynyl groups to synthesize dendrimers according to the invention.
Figure 11B:
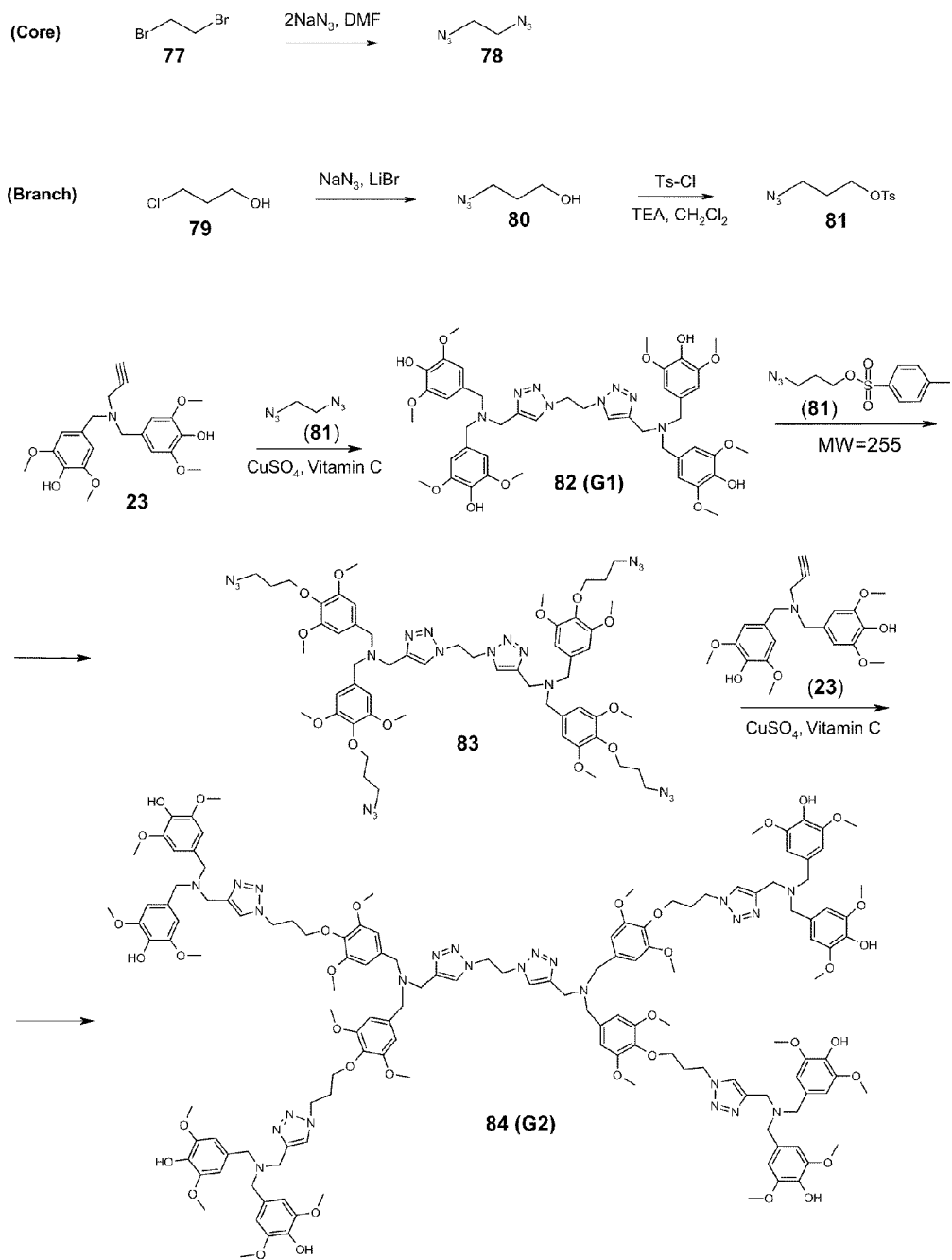
Figure 11C:
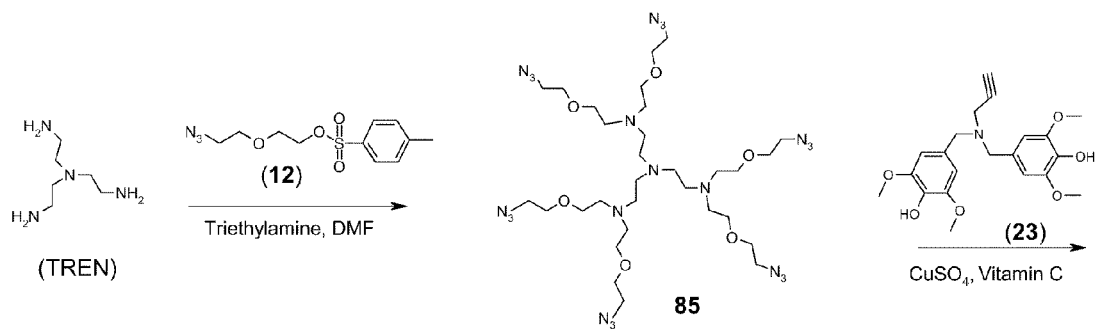
Figure 11C:
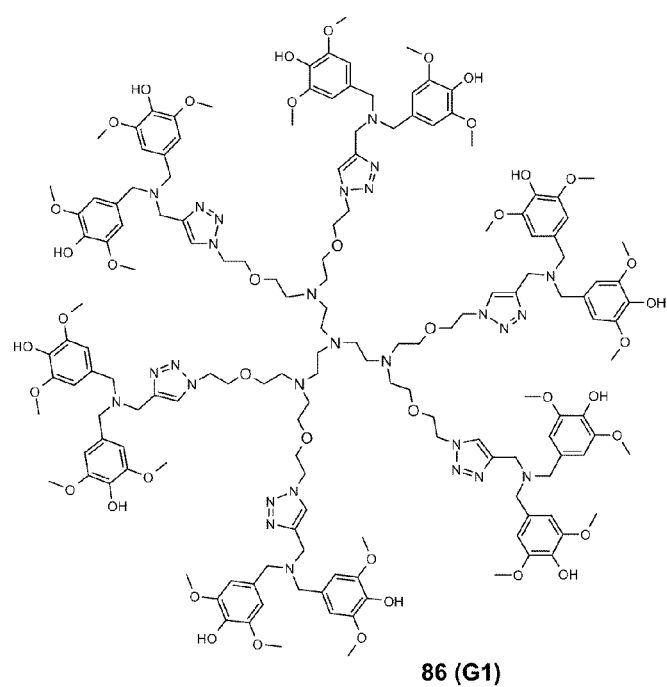

Click chemistry using azide and ethynyl groups (Sharpless et al. *Angew. Chem. Int. Ed.* 2001, 40, 2004-2021, incorporated herein by reference in its entirety) may be used to synthesize antioxidant dendrimers according to the invention. Example reaction schemes are shown in FIGS. 11A, 11B and 11C. As generally shown in FIG. 11A, azide groups of compound 16 were reacted with ethynyl group of compound 23 (four equivalents) in the presence of CuSO$_4$ and vitamin C to generate compound 76. Compounds 19 and 22 in place of compound 23 may also be used to generate congener dendrimers of compound 76. FIG. 11B describes another click chemistry method in dendrimer synthesis in which a different core was used. The core, 1,2-diazidoethane, was synthesized using 1,2-dibromoethane (compound 77) via nucleophilic displacement of the bromides by azide groups. The core was treated with compound 23 in the presence of CuSO$_4$ and vitamin C to form compound 82. The generation 1 dendrimer (compound 82) may be treated with various branching units, for example compound 81 (or 12) to form compound 83, which will serve as a scaffold for the larger dendrimer synthesis like compound 84. FIG. 11C shows a similar synthetic method to afore-mentioned click chemistry methods. TREN was used as a core to which compound 12 was attached to form compound 85. Azido groups of compound 85 may be treated with compound 23 (or the likes) to form compound 86.

Figure 12:
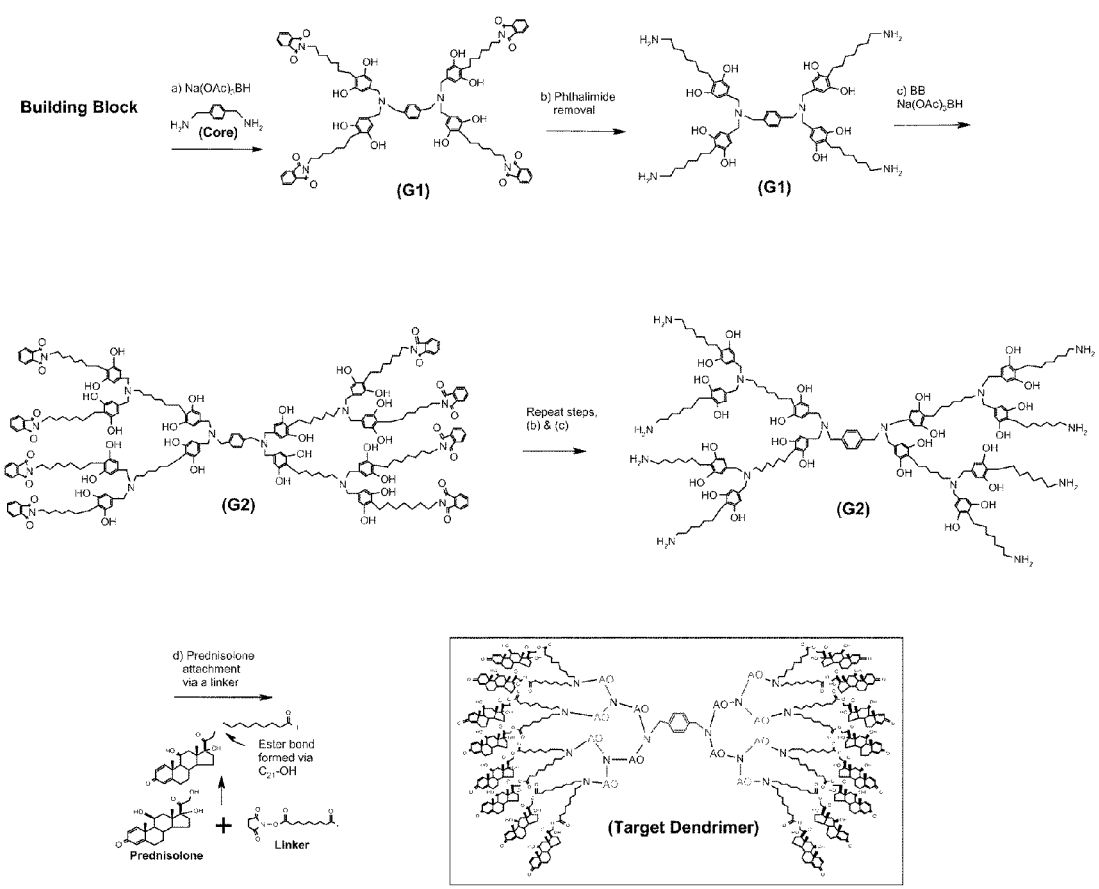
FIG. 12 is a scheme for the general synthesis of a G1 antioxidant dendrimer, and a G2 antioxidant dendrimer.

Compounds with an active agent such as prednisolone attached to the compound may be synthesized by any suitable method, including, for example, FIG. 12.

Compositions

The invention further relates to compositions comprising a compound according to General Formula I described above. The composition may be incorporated into a pharmaceutical composition, a cosmetic composition, a dietary supplement composition, or a beverage composition. The composition may further comprise a carrier. A "carrier" refers to one or more compatible substances that are suitable for administration to a cell or a subject. "Pharmaceutically acceptable carrier" means a carrier that is useful for the preparation of a pharmaceutical composition, i.e., generally compatible with the other ingredients of the composition, not deleterious to the recipient, and neither biologically nor otherwise undesirable. A pharmaceutically acceptable carrier may include a single carrier or more than one carrier. Embodiments include carriers for topical, parenteral, intravenous, intraperitoneal, intramuscular, sublingual, nasal, and oral administration. The composition may comprise an excipient. "Excipient" as used herein includes physiologically compatible additives useful in preparation of a composition. Examples of pharmaceutically acceptable carriers and excipients can for example be found in Remington Pharmaceutical Science, 16th Ed.

The invention further relates to administration of a compound or compositions as described above to a cell or a subject. "Administering" as used herein refers to administration of the compounds as needed to achieve the desired effect. As will be appreciated by those of skill in the art, an agent may be administered by various methods including sublingually, orally, enterally, parenterally, topically, systemically or injected intravascularly or intraarterially, cutaneously, or peritoneally. The compounds may be administered in a therapeutically effective amount. "Therapeutically effective amount" as used herein refers to a dosage of the compounds or compositions effective for influencing, reducing, inhibiting, or limiting oxidative damage or the activity of free radicals. This term as used herein may also refer to an amount effective at bringing about a desired in vivo effect in a subject such as an animal, preferably, a human, such as ameliorated or improved symptoms of a disorder or condition caused or characterized by oxidative damage. It is envisioned that suitable dosages include, but are not limited to, those effective to achieve concentrations in a subject of about 0.001 µM to about 50 mM. Dosages may be effective to achieve a concentration in the subject of at least about 0.001 µM, at least about 0.1 µM, at least about 1 µM, at least about 10 µM, at least about 100 µM, at least about 1 mM, at least about 10 mM, or at least about 40 mM of compound. Dosages may be effective to achieve a concentration of less than about 50 mM, less than about 10 mM, less than about 1 mM, less than about 100 µM, less than about 10 µM, less than about 1 µM, less than about 0.1 µM, or less than about 0.01 µM of compound. It is well within the ability of one of skilled in the art, given the disclosure provided herein, to determine effective dosages.

Oxidative stress to cells is associated with the pathogenesis of many diseases, including asthma, cancer, cardiovascular and neurological diseases, and other age-related degenerative diseases. Oxidative stress is also caused by inflammation. The compounds of the invention may be used to treat a disease or disorder or condition, including but not limited to inflammation, cancer, asthma, cardiovascular diseases such as atherosclerosis, neurological and neurodegenerative diseases, arthritis, hypertension, pulmonary ailments, reperfusion injury, and age-related disorders. Compounds disclosed herein may provide dual effects, i.e., radical absorption to reduce oxidative stress as well as delivery of an active agent to yield a therapeutic effect. Suitably, compounds and compositions according to the invention may prevent progression of a disease or disorder or condition as well as treat a disease or disorder or condition.

EXAMPLES

Example 1

Materials

Syringaldehyde, vanillin, quercetin, TREN (97%), Trolox (6-hydroxy-2,5,7,8-tetramethylchroman-2-carboxylic acid), 4-aminomethylbenzylamine, and sodium triacetoxyborohydride, n-Bu$_4$NF (75 wt % solution in water), TBDMS-Cl (50% in toluene), DPPH, Fat Red 7B, TPTZ (2,4,6-tris-2,4,6-tripyridyl-2-triazine), ABTS, PBS (phosphate-buffered saline), potassium persulfate, glacial acetic acid, sodium acetate, carbonic anhydrase (isozyme II from bovine erythrocytes), methanol, and ethanol were purchased from Sigma Aldrich and were used without further purification. Lysozyme (egg white) was purchased from Worthington Biochemical Corporation. AAPH was obtained from Cayman Chemical (Ann Arbor, Mich., USA). Human LDL was obtained from Kalen Biomedical (Montgomery Village, Md., USA). The lipoprotein solution (protein @5 mg/mL) contained 154 mM NaCl and 0.34 mM EDTA.

Melting points were determined in an open capillary on Mel-Temp II & Thomas Hoover Apparatus and were uncorrected. IR spectra were recorded on a Perkin Elmer Model 1600 FTIR spectrometer. $^1$H-NMR spectra were recorded with a Varian Mercury-300 spectrometer operating at 300 MHz with tetramethylsilane (Si(CH$_3$)$_4$) as an internal standard. $^{13}$C-NMR spectra were recorded using a Varian Mercury-300 spectrometer operating at 75 MHz with tetramethylsilane (Si(CH$_3$)$_4$) as an internal standard. The mass spectra were obtained on Bruker Autoflex MALDI-TOF using 2,5-dihydroxybenzoic acid as a matrix. All spectrophotometric data were obtained using Perkin Elmer UV/Vis spectrometer (Lambda 20) and Molecular Devices Corp. Spectra Max (M2$^e$). Antioxidant samples were prepared in either methanol or ethanol and stored at −20° C.

Example 2

Synthesis of Building Blocks and Branching Units

Figure 2:
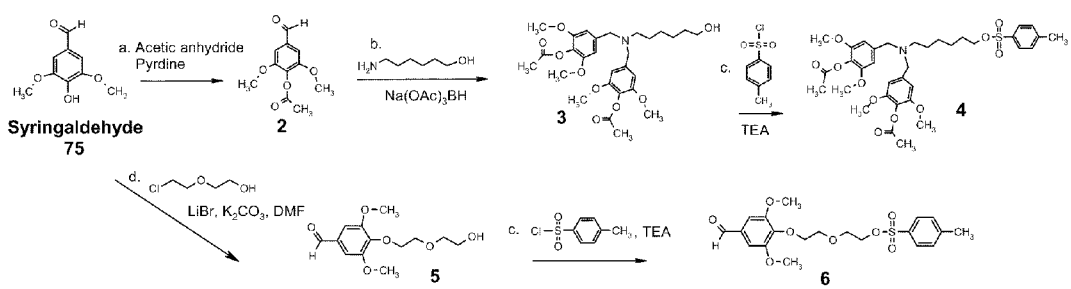
FIG. 2 is a scheme for the synthesis of building blocks and branching units.
Figure 2:
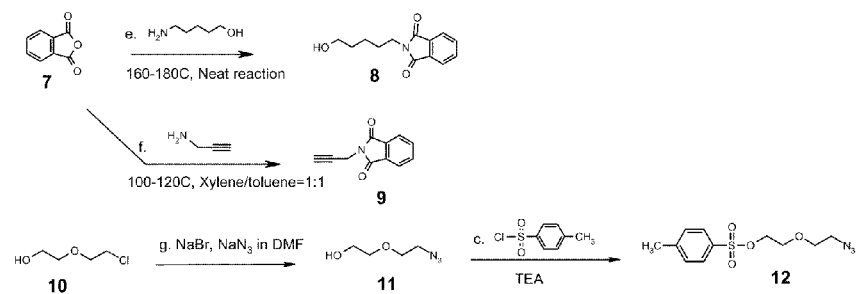

As generally shown in FIG. 2, we have synthesized a plurality of building blocks (3-6) and branching units (8, 9, 12) that may be used to prepare antioxidant dendrimers. For synthesis of building block 3, the hydroxyl group of syringealdehyde 75 was first protected with acetic anhydride and pyridine to form 2. Then the aldehyde of 2 was reacted with a primary amine end of 6-amino-1-hexanol in the presence of a reducing agent, sodium triacetoxyborhydride (Na(OAc)$_3$BH) to yield building block 3. We found sodium triacetoxyborhydride (Na(OAc)$_3$BH) to be an effective reducing agent for reductive amination as it worked at neutral pH as well as in the presence of acetic acid and afforded over 85% yield. An aliquot of 3 was tosylated to generate building block 4. Syringaldehyde 75 was also reacted with 2-(2-chloroethoxy)ethanol to form 5, which was tosylated to form building block 6.

Phthalic anhydride 7 was used to protect the amino group of 6-amino-1-hexanol to prepare branching unit 8. The reaction was run in neat condition using phthalic anhydride and 6-amino-1-hexanol at 160-180° C. The phthalic anhydride was also used to protect the amino group of propargyl amine to yield another branching unit 9. Since propargylamine has a low boiling point (84° C.), we found that the reaction had to be refluxed in solvent to prevent loss of propargylamine. The solvent was a mixture of toluene and xylene in a ratio of 1 to 1. Branching unit 12 was made by converting 10 to its azide derivative 11 by nucleophilic displacement of chloride with azide, followed by tosylation.

Example 3

Synthesis of G1 and G2 Dendrimers

Figure 8:
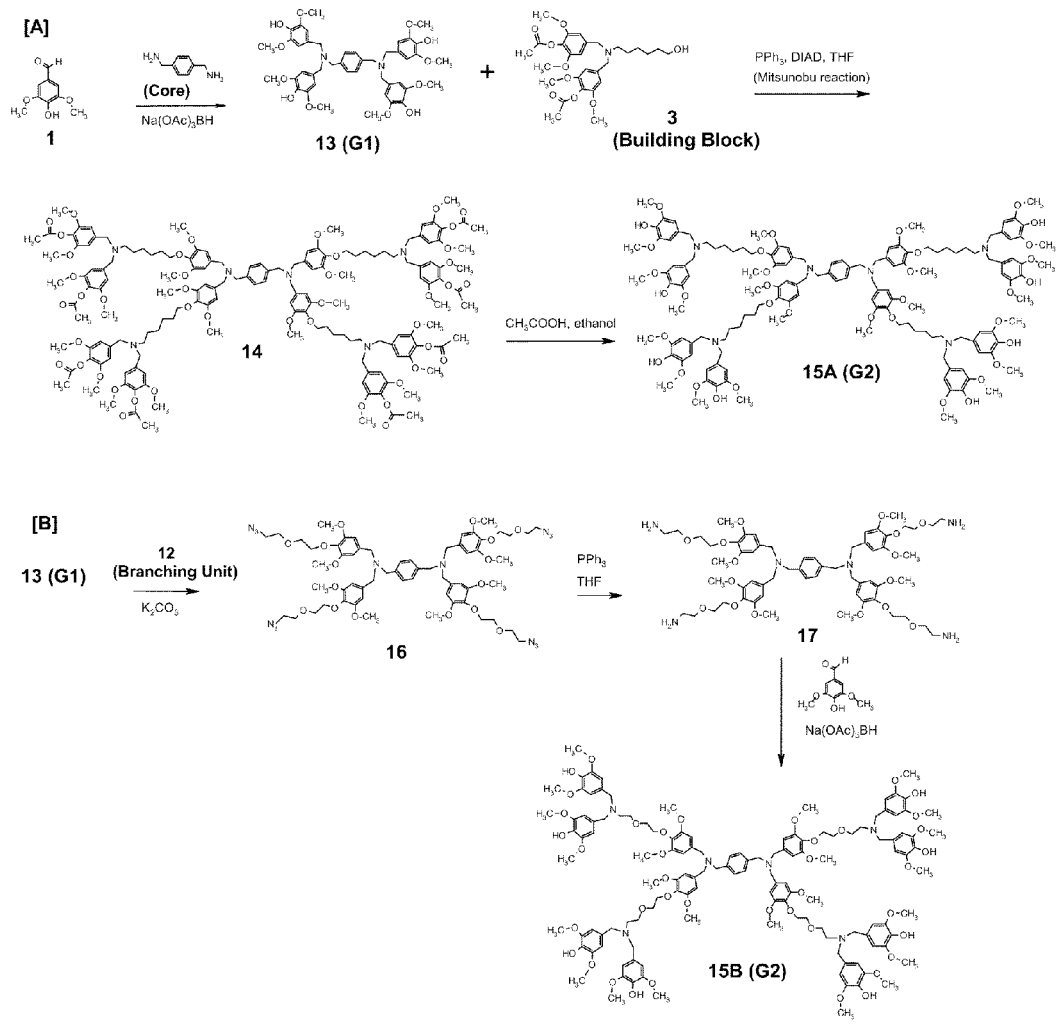
FIG. 8 is a scheme for the synthesis of G2 antioxidant dendrimers 15A and 15B.

We have synthesized generation 1 (G1) and generation 2 (G2) syringaldehyde-based dendrimers according to FIG. 8.

In the first step, four equivalents of syringaldehyde (75) were reacted with one equivalent of the core (4-aminomethlbenzylamine) in the presence of Na(OAc)$_3$BH) to yield G1 (13). The G1 was then attached to four equivalents of the building block 3 via the Mitsunobu reaction (PPh$_3$, diisopropyl azodicarboxylate, THF) to yield 14. The compound 14 could also be prepared using building block 4 (a tosylated form of building block 3 shown in FIG. 2). In this route, building block 4 may be (were) attached to 13 (G1) by nucleophilic substitution. Even though the two methods were equally effective, the Mitsunobu reaction was preferred because it involved one less step. The compound 14 was obtained in high yield (75%) and confirmed by MALDI and NMR. Deacetylation of 14 using glacial acetic acid in ethanol yielded a G2 dendrimer (15A).

Another generation 2 dendrimer (15B) was also synthesized using the methods shown in path [B] in FIG. 8. In that path, G1 (13) was treated with four equivalents of a prepared branching unit (12 shown in FIG. 2) to generate 16. Subsequently, azide groups of 16 were reduced to amino groups using PPh$_3$ to yield 17. We found the reduction method highly efficient (~95% yield). To the resulting amino ends of 17, eight equivalents of syringaldehyde were attached to generate G2 (15B). The existence of the G2 dendrimer in the reaction mixture was confirmed by MALDI-TOF.

We have tested AO activity of G1 (13) using ABTS as a radical source using a previously reported spectroscopic assay. The AO activity of the G1 (13) was compared to those of syringaldehyde, gallic acid, and vitamin C. If the phenolic OH group is the radical scavenging site, the expected AO activity of the G1 (13) should be 4 fold higher than that of syringaldehyde and 1.3 fold higher than that of gallic acid (which has three phenolic OH groups). However, the observed AO activity of the G1 (13) was significantly higher than that of syringaldehyde (7 fold), gallic acid (3 fold), and vitamin C (7.6 fold). This result demonstrated that even a small dendritic form of the AO (syringaldehyde) displays a dendritic effect.

Example 4

Dendrimer Syntheses Using Syringaldehyde Analogs

Figure 13:
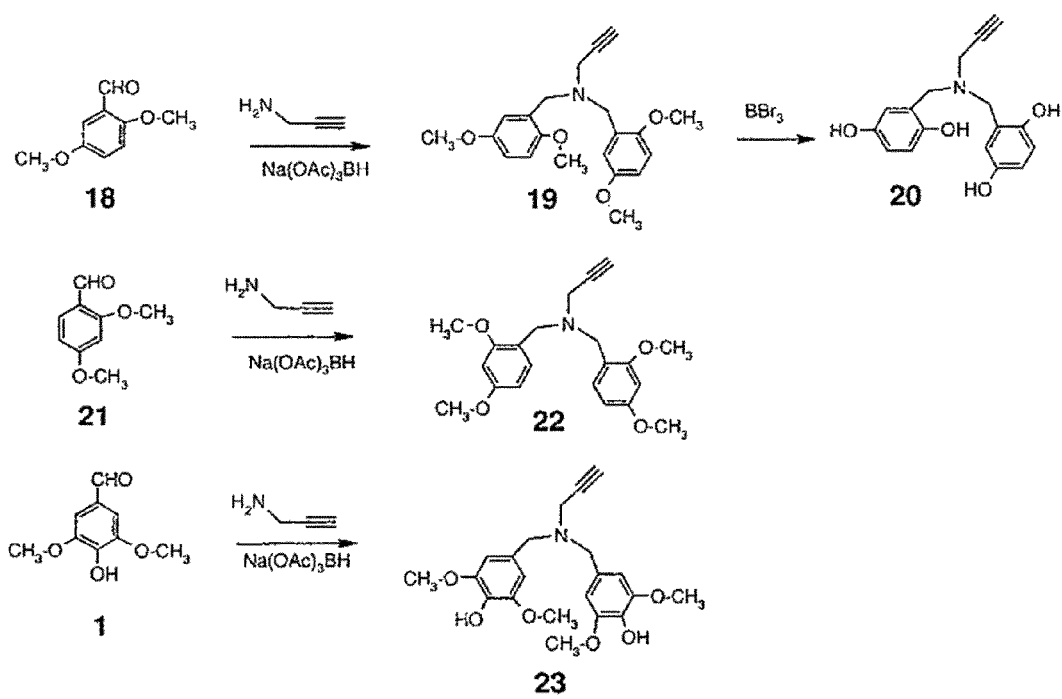
FIG. 13 are structures of synthesized building blocks using syringaldehyde and syringaldehyde analogs.

G1 (13) with only 4 phenolic hydroxyl groups showed promising antioxidant activities. We synthesized dendrimers with more hydroxyl groups on each phenyl ring by using modified syringaldehyde on which two hydroxyl groups are one carbon away from each other. The synthesized building blocks using syringaldehyde and syringaldehyde analogs are shown in FIG. 13. Two equivalents of 2,5-dimethoxybenzaldehyde (18) were attached to propargylamine in the presence of Na(OAc)$_3$BH to generate 19, which was subsequently demethylated with BBr$_3$ to yield 20. The triple bond of 19 was not affected by BBr$_3$. Building blocks 22 and 23 were prepared by the same methods used for Building block 19 synthesis from 2,4-dimethoxybenzaldehyde (21) and syringaldehyde (75), respectively.

Figure 7:
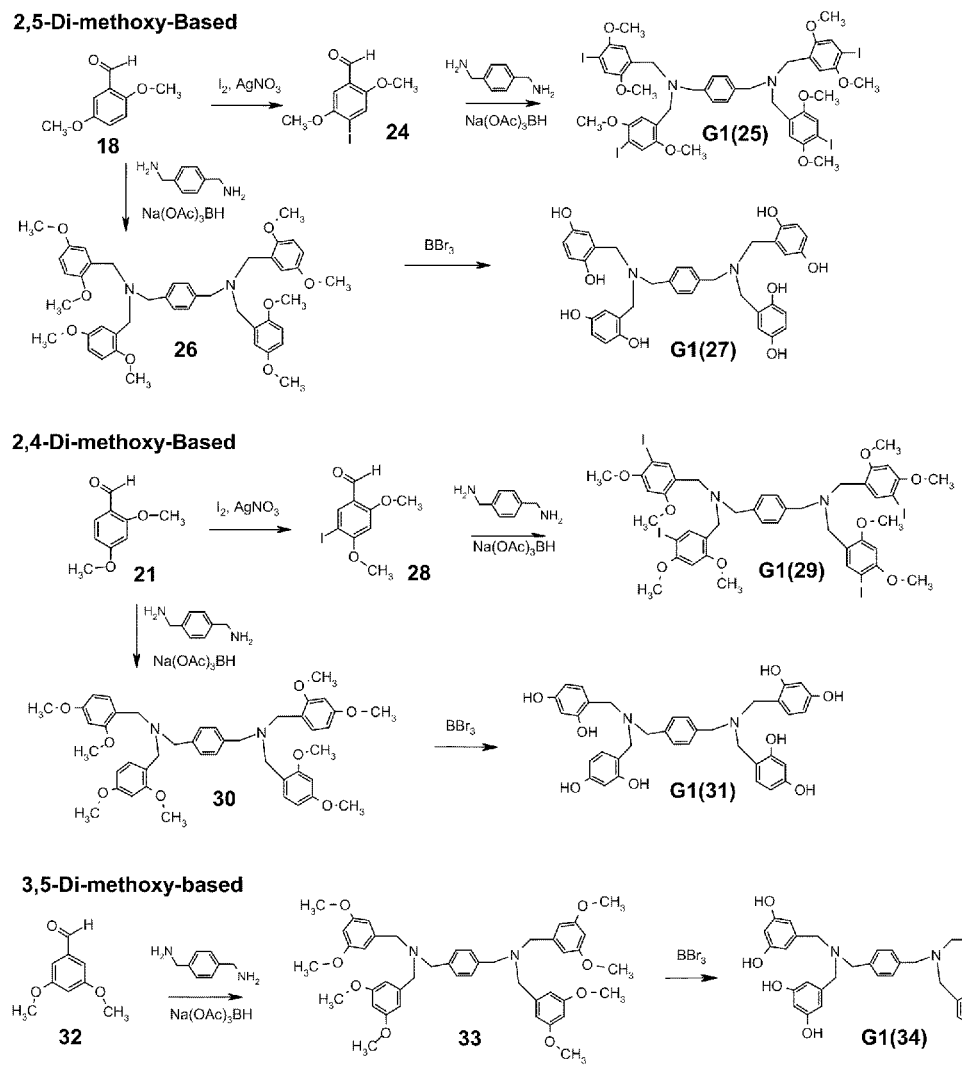
FIG. 7 is a scheme for the synthesis of G1 antioxidant dendrimers 25, 27, 29, 31, and 34.

We have also prepared G1 dendrimers using 2,5-dimethoxybenzaldehyde, 2,4 dimethoxy-benzaldehyde, and 3,5-dimethoxybenzaldehyde as a building block and 4-aminomethylbenzylamine as a core (FIG. 7). Compound 18 was iodinated using iodine and AgNO$_3$. The reaction introduced iodo group regiospecifically on the para (C-4) position to produce 24 and was highly efficient (~90% yield). The iodinated compound (24) was attached to the core unit (4-aminomethylbenzylamine) in the presence of Na(OAc)$_3$BH to form G1 (25). The starting material 18 was also directly attached to the same core unit to produce 26 which was subsequently demethylated using $BBr_3$ to produce G1 (27). The compound 29 is a congener of 25, differing in the location of the methoxy groups on its benzene rings whereas 31 is a congener of 27, differing in the location of the hydroxyl groups on its benzene rings. Compounds 29 and 31 were synthesized using exactly the same methods used for 25 and 27, respectively. Compound 32 was reacted with the same core unit in the presence of $Na(OAc)_3BH$ to produce 33 which in turn was demethylated to yield another type of G1 (34). G1 34 together with G1 27 and G1 31 are congeners, differing in the location of the hydroxyl groups on their benzene rings.

Example 5

The building blocks shown in FIG. 13 will be attached to the corresponding G1 dendrimers shown in FIG. 7, for example building block 19 to G1 25 and building block 22 to G1 29. The reaction we will use for the attachment is the Sonogashira reaction in which Pd catalyst (e.g. $Pd(dba)_2$, $PdCl_2(PPh_3)_2$, $Pd(PPh_3)_4$, or $Pd(OAc)_2$), CuI, and diethylamine (or N,N-diisopropylethylamine) are typically used reagents.

Example 6

Formation of a Syringaldehyde Tetramer Using 4-Aminomethylbenzylamine as a Core (Compound 1)

Figure 14:
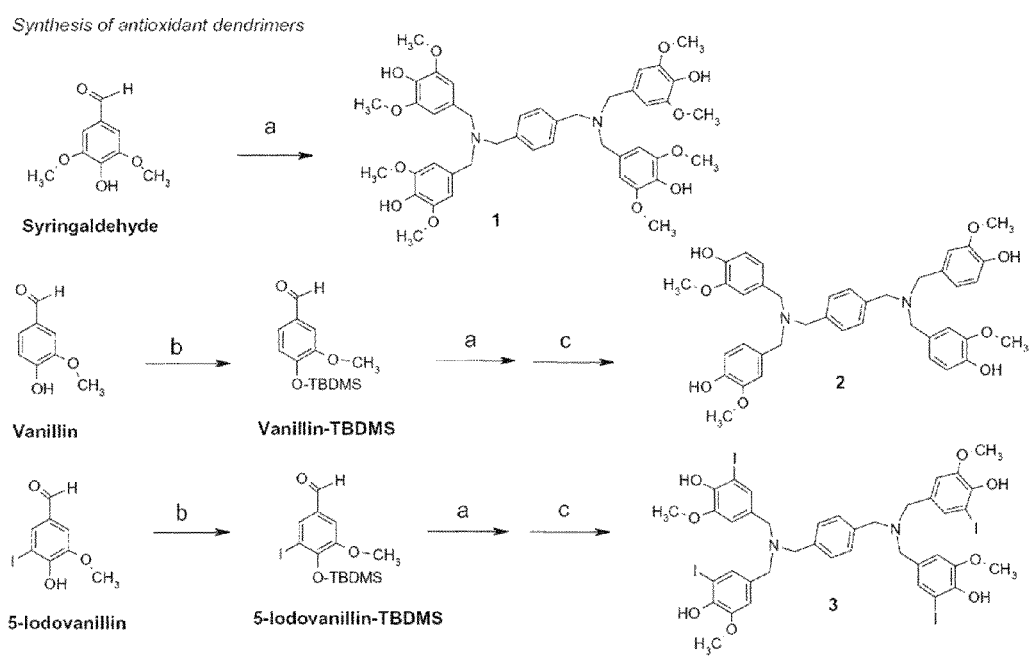
FIG. 14 is a scheme for the syntheses of antioxidant dendrimers, compounds 1, compound 2, and compound 3.

4-Aminomethylbenzylamine (1.63 g, 11.96 mmol) and 2.2 equivalents of syringaldehyde (4.81 g, 26.4 mmol) were dissolved in 1,2-dichloroethane in the presence of molecular sieves (50 g) and the reaction mixture was stirred for 5 hours under argon at room temperature to form imines (Lee, C. H., et al. *Bioorg. Med. Chem. Letts.* 2009, 19, 6326-6330, incorporated herein by reference in its entirety). Subsequently, sodium triacetoxyborohydride (5.60 g, 26.4 mmol) was added and the reaction was carried out for another 24 hours to reduce the imines. To the resulting secondary amines in the reaction mixture, 2 to 2.3 equivalents of syringaldehyde (5.0 g, 27.4 mmol) was added to form tertiary amines as shown in FIG. 14. In FIG. 14, (a) is 4-aminomethylbenzylamine, $Na(OAc)_3BH$, 1,2-dichloroethane; (b) is TBDMS-Cl, triethylamine, $CH_2Cl_2$, 0° C.; and (c) is n-$Bu_4NF$, THF. The reaction was stirred for 5 hours, followed by sodium triacetoxyborohydride (6.02 g, 28.4 mmol) addition.

$Na(OAc)_3BH$ was found to be an effective reducing agent for reductive amination as it worked well at neutral pH, affording an excellent yield (>80%). The high percent yield was achieved by adding the reagents in a sequential manner. Unlike previously reported (Abdel-Magid, et al. *J. Org. Chem.* 1996, 61, 3849-3862, incorporated herein by reference in its entirety), we found that the aldehyde of syringaldehyde (as well as other arylaldehydes) was reduced to an alcohol (syringic alcohol) by $Na(OAc)_3BH$ fairly rapidly. When the reducing agent was used in stoichiometric excess, syringic alcohol was observed within 0.5 hr. The exposure of aldehyde to the reducing agent was minimized by treating two equivalents of syringaldehyde with 4-aminomethylbenzylamine and allowing the reaction sufficient time before addition of $Na(OAc)_3BH$. This ensured that the aldehyde reacted with amino group first with limited exposure to the reducing agent. By adding the reagents sequentially to minimize aldehyde reduction by $Na(OAc)_3BH$, percent yield of the reaction was increased from 46% (one pot reaction) to 81% (stepwise reaction). $Na(OAc)_3BH$ was effective in the presence of free phenolic OH groups and did not require protection of the latter group.

Formation of the target compound (compound 1) was monitored with MALDI-TOF. The reaction was stopped 48 hours after the sodium triacetoxyborohydride addition. The 1,2-dichloroethane was removed by a rotary evaporator and the remaining oily residue was re-dissolved in chloroform and washed with water. The organic layer was dried using magnesium sulfate. After removal of magnesium sulfate by vacuum filtration, the filtrate was evaporated to dryness under reduced pressure with a rotary evaporator. The resulting oily substance was dissolved in acetone (5 mL) and mixed with silica gel. The mixture was dried, loaded on a silica gel column, and purified using a gradient hexane-ethyl acetate solvent system (8:1→1:1). The target compound (compound 1) eluted from the column was slightly off-white in color with a yellowish tint. The impure product was further purified via recrystallization using a mixture of hexane and ethylacetate (50:50) or triturated using acetone and hexane. Percent yield: 7.76 g (81%); mp: 89-92° C.; Rf value: 0.126 in hexane-acetone (1:1); $^1$H-NMR (300 MHz, $CDCl_3$) showed signals at δ 3.45 (s, 8H) 3.55 (s, 4H) 3.9 (s, 24H) 5.4 (s, 4H, hydroxyl-H) 6.6 (s, 8H) and 7.3 (s, 4H); $^{13}$C-NMR (75 MHz, $CDCl_3$) showed signals at δ 56.5, 57.9, 58.2, 105.6, 129, 131, 133.5, 138.2, 147; MS: m/z 801 [M+H$^+$]; FT-IR (KBr): 3422, 3001, 2936, 2837, 1615, 1516, 1463, 1429, 1375, 1326, 1212, 1109.

Example 7

DPPH Assay

The DPPH assay was one of three electron transfer (ET) assays used to determine the antioxidant potential of compound 1 (described in Example 6) in comparison to its monomeric counterpart (syringaldehyde) as well as popular antioxidants. In an ET assay, an antioxidant donates electron(s) to a molecular probe, thus reducing it. From the assay, thermodynamic conversion of antioxidant to antioxidant radical (oxidation) is measured during a fixed time period.

The antioxidants tested ranged from hydrophilic (ascorbic acid) and weakly hydrophobic (compound 1, Trolox, and syringaldehyde). The reduction of DPPH radical was determined for ascorbic acid, Trolox, syringaldehyde, and the compound 1 described in Example 6 as previously reported (Brand-Williams, et al. *Lebensm.-Wiss U.-Technol.* 1995, 28, 25-30, incorporated herein by reference in its entirety). In the DPPH assay, DPPH• radical was reduced by the antioxidant in methanol (Brand-Williams, et al. *Lebensm.-Wiss U.-Technol.* 1995, 28, 25-30, incorporated herein by reference in its entirety). DPPH radical (DPPH•) shows an absorbance 515 nm, which decreases upon reduction by the antioxidant. The DPPH reagent was made in methanol. Antioxidant sample (10 μL) was added to 1.0 mL of reagent and the absorbance was monitored at 515 nm until a plateau was reached. Antioxidant concentrations were 50 μM syringaldehyde, 12.5 μM Trolox and ascorbic acid, and 5 μM compound 1. All samples were made in methanol and run in triplicates at room temperature. The within-run coefficient of variation of the % inhibition values was less than 6%.

Figure 15:
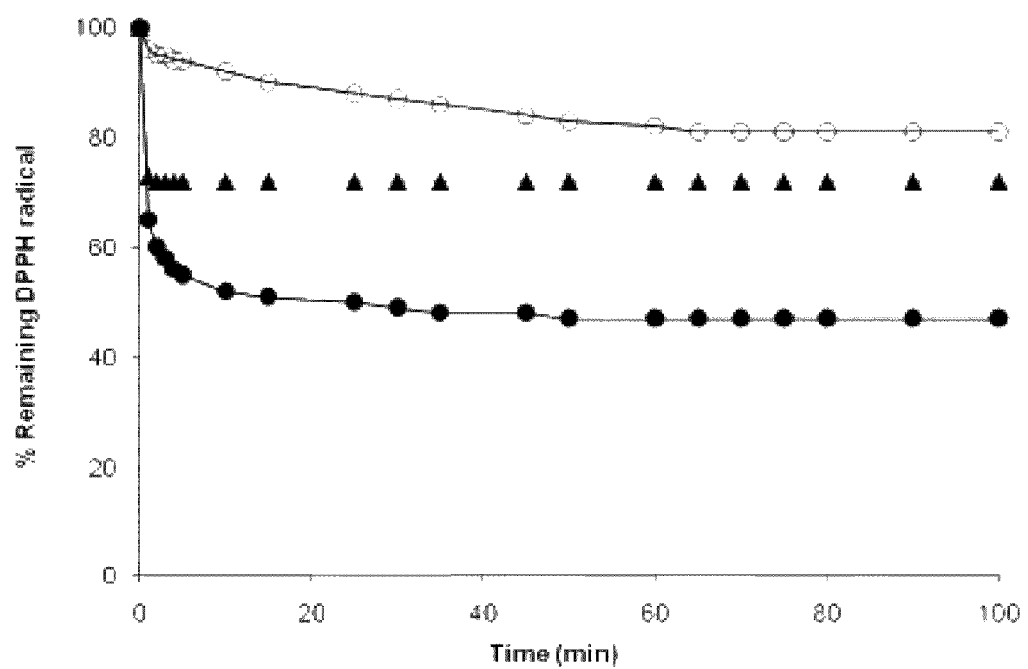
FIG. 15 is a graph of the remaining DPPH radical over time for syringaldehyde (open circles), Trolox and ascorbic acid (closed triangles), and compound 1 (closed circles) at room temperature as monitored at 515 nm.

FIG. 15 shows the reaction kinetics of compound 1 compared to other antioxidants. Trolox reacted rapidly with DPPH• reaching a plateau within 2 min. Ascorbic acid also showed similar kinetic behavior in agreement with previous work (Brand-Williams, et al. *Lebensm.-Wiss U.-Technol.* 1995, 28, 25-30, incorporated herein by reference in its entirety). Both syringaldehyde and its tetrameric form (compound 1, described in Example 6) displayed much slower kinetics compared to Trolox or ascorbic acid, and reached steady state in approximately 45 min. Syringaldehyde showed a slow and gradual decrease in radical scavenging with time. In one minute, there was 96% DPPH• remaining. After one minute, the DPPH• dropped gradually by 1-2%/min. The slow kinetics displayed by syringaldehyde may be due to its aldehyde group, which is weakly electron withdrawing. Presence of electron withdrawing group(s) on the benzene ring diminishes the H-donation ability of the phenolic —OH. The compound 1 exhibited a biphasic kinetic profile, indicative of the presence of two or more reactive centers. In two minutes, there was a rapid drop from 100% to 60% DPPH•. After that, the DPPH• dropped gradually by 1-2%/min, reaching a plateau at 46%. The initial burst of radical scavenging seen in the kinetic profile of compound 1 is likely due to its reactive phenolic hydroxyl groups (a, FIG. 8) while the slower second phase may be attributed to the benzylic hydrogens (b and c, FIG. 8). The higher reactivity of phenolic hydroxyl groups compared to benzylic hydrogen atoms in the compound 1 may be due to their increased H atom donating potential and less steric hindrance towards the DPPH free radicals. In syringaldehyde, the aldehyde group is electron withdrawing. However, in the compound 1 the aldehyde groups are transformed into electron donating benzylic hydrogens. The benzylic hydrogens para to the phenolic hydroxyl groups enhance the H atom (or electron) donating potential of the latter, resulting in enhanced free radical scavenging activity of the compound 1. Steric hindrance between the bulky DDPH• radicals and the interior benzylic hydrogens could also be partly responsible for the slower radical quenching phase exhibited by the compound 1 (FIG. 15).

Figure 16:
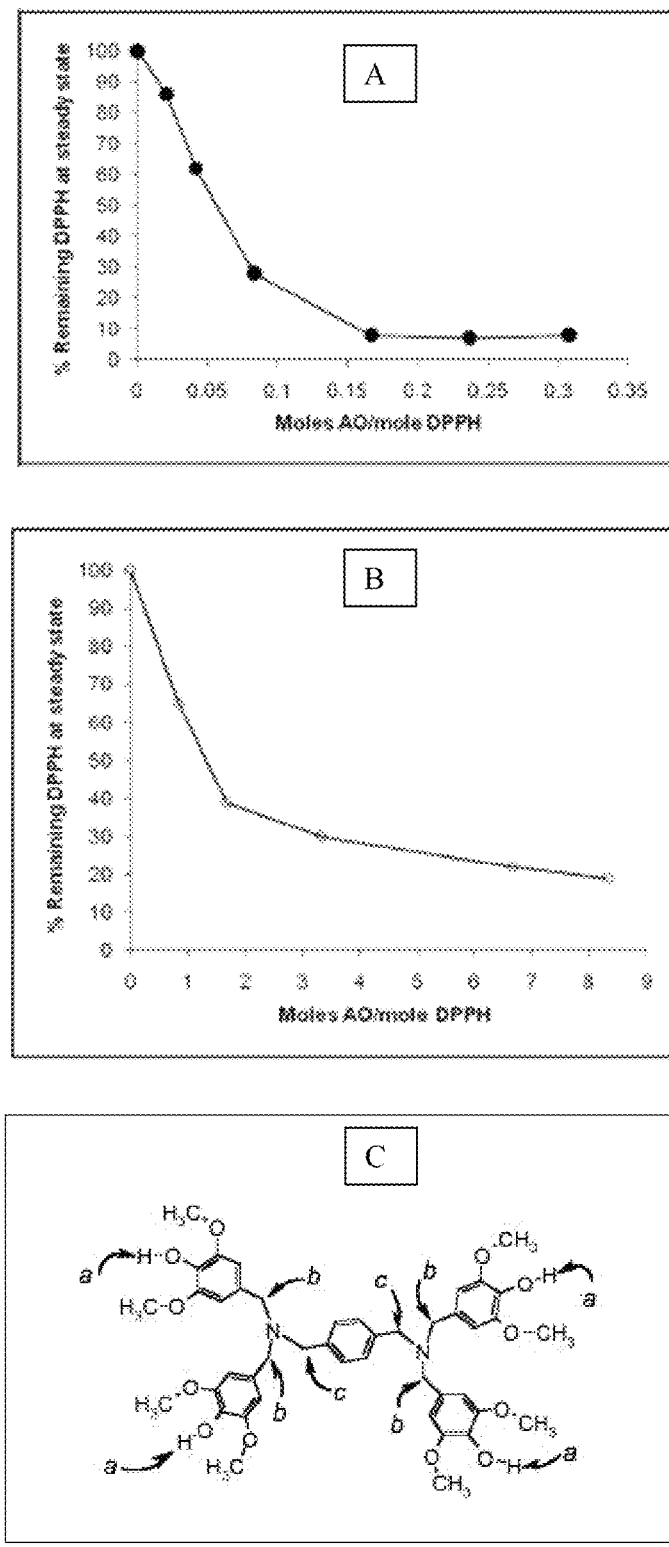
FIG. 16 is a graph of the remaining DPPH radical versus the number of moles of antioxidant per mole of DPPH• for compound 1 (A) and syringaldehyde (B). (C) The plausible sites of compound 1 for free radical scavenging.

The DPPH• scavenging capacity of each antioxidant was evaluated from the plot of the percentage DPPH• remaining when the kinetics reached a steady state as a function of the molar ratios of antioxidant to DPPH•. The curves for syringaldehyde and compound 1 are shown in FIG. 16. Similar curves were obtained for Trolox and ascorbic acid (data not shown). Using the curve, $EC_{50}$ (the amount of antioxidant necessary to decrease the initial DPPH• concentration by 50%), antiradical power ($1/EC_{50}$, ability to reduce the DPPH•), reaction stoichiometry ($EC_{50} \times 2$, the concentration of antioxidant required to reduce 100% of DPPH• radical), and the number of reduced DPPH• per antioxidant molecule (1/stoichiometry) for each antioxidant were calculated as previously described (Brand-Williams, et al. *Lebensm.-Wiss U.-Technol.* 1995, 28, 25-30, incorporated herein by reference in its entirety) and are depicted in Table 1. The antiradical power (ARP) of compound 1 (17.54) was about 27, 5, and 5 times stronger than syringaldehyde (0.66), Trolox (3.57), and ascorbic acid (3.57), respectively. The ARP value for ascorbic acid (3.57) was slightly lower than the previously reported value (3.70) (Brand-Williams, et al. *Lebensm.-Wiss U.-Technol.* 1995, 28, 25-30, incorporated herein by reference in its entirety).

TABLE 1

Antiradical efficiency, stoichiometry, and amount of DPPH reduced

| Antioxidant | $EC_{50}$ | ARP | Stoichiometry | # of DDPH• reduced |
| --- | --- | --- | --- | --- |
| Ascorbic acid | 0.28 | 3.57 | 0.56 | 1.8 |
| Trolox | 0.28 | 3.57 | 0.56 | 1.8 |
| Syringaldehyde | 1.51 | 0.66 | 3.02 | 0.33 |
| Compound 1 | 0.057 | 17.54 | 0.11 | 8.8 |

The DPPH data indicated that appropriate assembly of small and weak antioxidants may yield potent antioxidant macromolecules. In this case, we have converted a relatively weak antioxidant, syringaldehyde, into a potent tetrameric form by attaching four syringaldehyde moieties to one another via a 4-aminomethylbenzylamine core. The high antioxidant efficiency of compound 1 may be due to its unique structural arrangement with multiple built-in radical scavenging sites. The four syringaldehyde molecules were assembled through their aldehydes, which were converted into benzylic hydrogens in compound 1. Resonance stabilization enables the benzylic hydrogens to be readily donated to the free radicals. The conversion of aldehyde group to labile benzylic group resulted in doubling the number of radical scavenging sites in compound 1, contributing to an enhanced antioxidant capacity. In addition to four phenolic hydroxyl groups (a, FIG. 16C) and four benzylic hydrogens (b, FIG. 16C) on the four peripheral phenyl rings, the core molecule (4-aminomethylbenzylamine) contains two benzylic hydrogens (c, FIG. 16C) that can also serve as sites for scavenging free radicals, giving a total of ten possible radical scavenging sites.

The stoichiometry obtained for each antioxidant was 0.56 (ascorbic acid and Trolox), 3.02 (syringaldehyde), and 0.11 (compound 1). We also determined the number of reduced DPPH• radical per antioxidant molecule from the reciprocal of their stoichiometry values, as suggested by Brand Williams et al. (*Lebensm.-Wiss U.-Technol.* 1995, 28, 25-30, incorporated herein by reference in its entirety). Both ascorbic acid and Trolox reduced 1.8 radicals, while a syringaldehyde reduced 0.33 radical, and one tetramer molecule (compound 1) reduced 8.8 DPPH• radicals. According to these results, the antioxidants have stoichiometric values and the number of reduced DPPH• radical per antioxidant molecule that correspond to the number of hydrogens available for donation except syringladehyde. Our stoichiometry value (0.56) and the number of reduced DPPH• radical per antioxidant molecule (1.8) obtained for ascorbic acid were fairly consistent with the previously reported values, 0.54 and 1.85, respectively, indicating that it could reduce two DPPH• radicals. The two enolic hydroxyl groups in the 5-membered ring of ascorbic acid are involved in DPPH• radical quenching (Brand-Williams, et al. *Lebensm.-Wiss U.-Technol.* 1995, 28, 25-30, incorporated herein by reference in its entirety). Based on our results, each Trolox molecule reduces approximately two DPPH• molecules. In comparison, syringaldehyde could only reduce 0.33 DPPH• radical. In other words, one DPPH• was quenched by every three syringaldehyde molecules. The poor H-donating ability of the —OH group on syringaldehyde may be partly due to the presence of the aldehyde group that is weakly electron withdrawing. This was evident from the slow kinetics displayed by syringaldehyde (FIG. 15). On the contrary, the compound 1 formed by four syringaldehyde molecules and the core showed significantly higher DPPH• radical scavenging ability (approximately 8.8 DPPH•/per molecule) than its monomeric component, syringaldehyde. This data indicates that the compound 1 could reduce about nine DPPH• radicals by donating nine hydrogens (or electrons) from the ten possible sites. The nine hydrogens involved in radical quenching may originate from all four phenolic —OH groups (a, FIG. 16C), four benzylic hydrogens (b, FIG. 16C) on four peripheral phenyl rings, and one of the remaining two benzylic hydrogens (c, FIG. 16C) located in the core of compound 1. To test this, we measured the DPPH radical scavenging capacity of the 4-aminomethylbenzylamine core molecule. It was found that the core did exhibit a weak DDPH• quenching capacity. A 40 µM core (final concentration in cuvet) solution gave a 6% quenching of DDPH• while a 5 µM solution of compound 1 gave 60% decrease in DDPH• under similar conditions (data not shown). This suggested that the ninth hydrogen involved in DPPH• radical scavenging is one of the benzylic hydrogens in the core.

The DPPH• reduction to DPPH by a phenolic antioxidant was believed to involve hydrogen atom transfer (HAT) mechanism. However, Foti et al. (Foti et al., *J. Org. Chem.* 2004, 69, 2309-2314, incorporated herein by reference in its entirety) reported that phenolic antioxidants (cinnamic acid, their methyl esters and catechols) in alcoholic solution reduce the DPPH• by electron transfer mechanism based on kinetic analysis of the reaction between phenols and DPPH•. It was discovered here that the —OH of phenol strongly H-bonds with a polar solvent (ArOH—solvent). This prevents the phenols from donating hydrogen atom (H•) via the HAT mechanism. The reaction pathway suggested by the authors is described below:

ArOH⇌ArO⁻+H⁺

ArO⁻+DPPH•→ArO•+DPPH⁻

DPPH⁻+H⁺→H-DPPH

ArO•+DPPH•→ArO-DDPH

The phenoxide anion formed donates an electron to DPPH• radical, followed by protonation of the reduced DPPH (DPPH—). In case of compound 1, the reduction of DPPH radical may proceed by both ET and HAT mechanisms. The phenolic hydroxyl groups will reduce DPPH• radical via ET in methanol as shown above. On the other hand, the benzylic hydrogens may follow a HAT mechanism since benzylic hydrogens do not form H-bonds with the polar medium.

Example 8

ABTS Assay

ABTS radical cation decolorization assay was used as previously described (Ozgen, et al. *J. Agric. Food Chem.* 2006, 54, 1151-1157, incorporated herein by reference in its entirety). Like the DPPH assay, this was also a decolorization assay and measured absorbance decrease at 734 nm as the ABTS radical (ABTS•+) is quenched by the antioxidant. The solvent used for the assay was ethanol. ABTS reagent was added to 1.0 mL solvent in a cuvet to bring the absorbance to 0.7. A 10 µL sample of antioxidant was then added, mixed, and the absorbance monitored at 734 nm for 6 min. Antioxidant concentrations were 14.4 µM Trolox, 11.4 µM ascorbic acid, 15.4 µM syringaldehyde, and 3 µM compound 1. The % decrease in absorbance at 6 min was plotted against antioxidant concentrations. The gradient of the line obtained by linear regression for a given antioxidant was divided by that obtained for Trolox to yield Trolox equivalent antioxidant (TEAC) values. All samples were made in ethanol and run in triplicates and at room temperature. The within-run coefficient of variation of the % inhibition values (at 6 min) was less than 6%.

Figure 17:
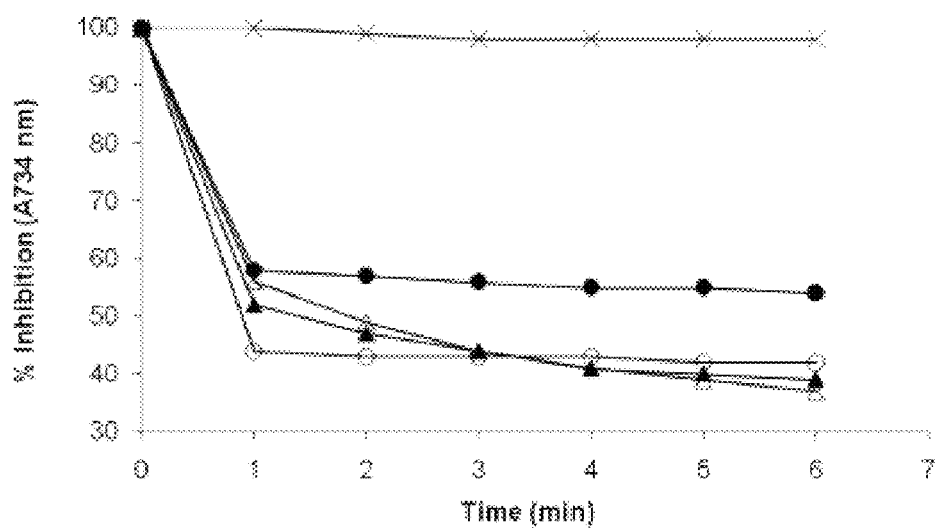
FIG. 17 is a graph of the percent reduction in absorbance at 734 nm versus time, showing the kinetics of ABTS radical scavenging by no antioxidant (X), Trolox (open circles), ascorbic acid (closed circles), syringaldehyde (open triangles), and compound 1, closed triangles).

The ABTS•+ absorbance suppression by compound 1 and other antioxidants over time is shown in FIG. 17. Both Trolox and ascorbic acid reached a plateau in one minute, in agreement with Re et al. (*Free Radic. Biol. Med.* 1999, 26, 1231-1237, incorporated herein by reference in its entirety). However, syringaldehyde and compound 1 showed a gradual decrease in absorbance even at 6 minutes. From the linear portions of the graphs in FIG. 17, regression equations were obtained and are depicted in Table 2. In the case of Trolox, 50% inhibition was observed at ~10 µM (final concentration in the cuvet), in agreement with Re et al. (*Free Radic. Biol. Med.* 1999, 26, 1231-1237, incorporated herein by reference in its entirety). For ascorbic acid, syringaldehyde and compound 1, the corresponding values were approximately 13 µM, 11 µM, and 1.5 µM, respectively.

TABLE 2

TEAC values of antioxidants

| Antioxidant | TEAC | Linearity tested (µM) | Slope | Intercept | R₂ |
|---|---|---|---|---|---|
| Compound 1 | 8.48 | 0-1.5 | 33.9 | −0.9 | 0.972 |
| Syringaldehyde | 0.98 | 0-15 | 3.9 | 5.6 | 0.965 |
| Ascorbic acid | 0.90 | 0-22 | 3.6 | 3.2 | 0.980 |
| Trolox | 1 | 0-14 | 4 | 7.6 | 0.920 |

TEAC values for ascorbic acid, syringaldehyde, and compound 1 were calculated by dividing their respective slopes with that of Trolox (Table 2). Ascorbic acid showed a TEAC of 0.9, which was slightly less than 1.05, reported by Re et al (*Free Radic. Biol. Med.* 1999, 26, 1231-1237, incorporated herein by reference in its entirety). Based on the TEAC values obtained with this assay, compound 1 was 8.5, 9.4, and 8.7 times better than Trolox, ascorbic acid, and syringaldehyde, respectively, yielding a rank order: compound 1>Trolox>syringaldehyde>ascorbic acid. We did not attempt to calculate the number of ABTS•+ quenched per antioxidant molecule since there was no correlation between TEAC values obtained by this method and the number of electrons donated by an antioxidant (Huang, et al. *J. Agric. Food Chem.* 2005, 53, 1841-1856, incorporated herein by reference in its entirety).

Example 9

FRAP Assay

Figure 18:
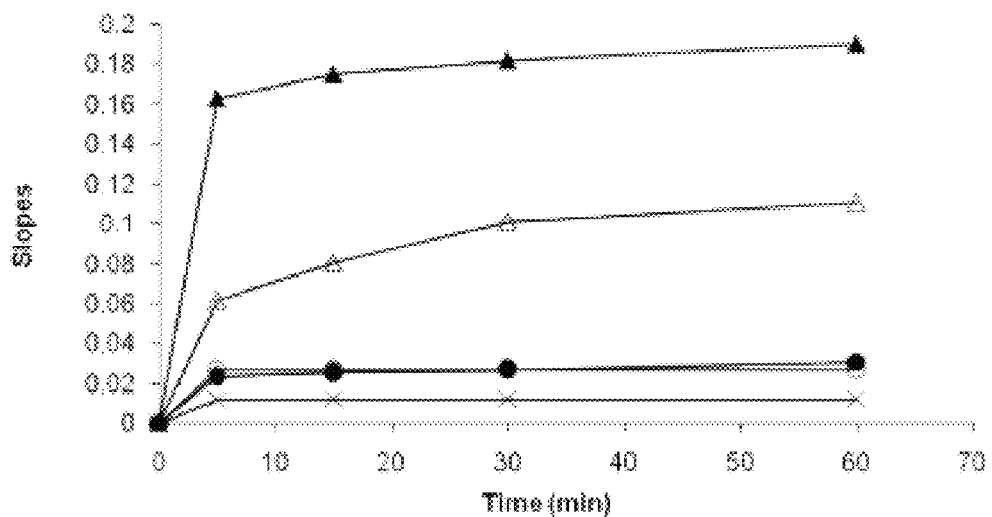
FIG. 18 is a graph of the slope of the change in absorbance at 593 nm versus time, showing the reaction kinetics of various antioxidants for the reduction of Fe(III) to Fe(II). Antioxidants include Trolox (open circles), ascorbic acid (closed circles), syringaldehyde (open triangles), and compound 1 (closed triangles). The Fe(II) standard is indicated by (X).

The FRAP assay was performed as previously described (Pulido, et al. *J. Agric. Food Chem.* 2000, 48, 3396-3402, incorporated herein by reference in its entirety). In the FRAP assay, ferric was reduced by the antioxidant to ferrous via electron transfer (Benzie et al., *Anal. Biochem.* 1996, 239, 70-76, incorporated herein by reference in its entirety). This assay measured the redox potential of an antioxidant which is used as an estimate of antioxidant efficiency and expressed as a FRAP value. One FRAP unit was defined as the reduction of 1 mol ferric to ferrous. The antioxidant sample (10 µL) was added to 200 µL FRAP reagent in a 96 well plate. All samples, including Fe(II) standards (using $FeSO_4 \cdot 7H_2O$) were made in methanol and run in triplicates at 37° C. The within-run coefficient of variation of the $A_{593\ nm}$ values was less than 6%. One FRAP unit was defined as the reduction of 1 mol ferric to ferrous. The oxidant was the ferric(III) ion complexed with TPTZ, $Fe(III)(TPTZ)_2Cl_3$. On reaction with an antioxidant, it reduced to $Fe(II)(TPTZ)_2Cl_2$, which absorbs strongly at 593 nm. The change of absorbance at a given time, t min ($\Delta A = A_{t\ min} - A_{0\ min}$), was determined for various concentrations of antioxidants as well as for Fe(II) standards at 5, 15, 30, and 60 min. The compound 1 as well as the other antioxidants was dissolved in methanol. Fe(II) calibrators were also made in methanol as suggested by Pulido et al. (*J. Agric. Food Chem.* 2000, 48, 3396-3402, incorporated herein by reference in its entirety). The slopes and intercepts obtained from the regression equations are shown in Table 3. Reaction kinetics of the compound 1 and other antioxidants were obtained by plotting the change in slopes at various times and are shown in FIG. 18. In case of Trolox, the maximum slope was obtained within 5 min and remained constant during the testing period (60 min). Ascorbic acid also showed a plateau within 5 min, but slowly increased with time (Table 3, FIG. 18). However, both syringaldehyde and compound 1 showed a prominent increase of their slopes with time even at 60 min. This time-dependent increase in absorbance was previously reported (Pulido, et al. *J. Agric. Food Chem.* 2000, 48, 3396-3402, incorporated herein by reference in its entirety) and was especially significant with polyphenolic compounds. The ferric ion reducing capacity of the various antioxidants at different times are shown in Table 4. The FRAP value for Trolox was 2.2 and did not change with time (Table 4). The FRAP value for ascorbic acid was ~2 at 5 min. However, the FRAP value increased with time, reaching 2.5 in 60 min. Both syringaldehyde and compound 1 showed increasing FRAP values with time (Table 4). Clearly, the FRAP values of these compounds cannot be interpreted as the number of mol Fe(III) reduced with this assay, so the equivalent concentration 1 ($EC_1$) was used for ranking antioxidant efficiencies (Pulido, et al. *J. Agric. Food Chem.* 2000, 48, 3396-3402, incorporated herein by reference in its entirety). The $EC_1$ is the concentration of the antioxidant having a ferric-TPTZ reducing ability equivalent to that of a 1 mM concentration of $FeSO_4.7H_2O$. Our calculated $EC_1$ values at 5 min were 450, 505, 194, and 74 μM for Trolox, ascorbic acid, syringaldehyde and compound 1, respectively. At 60 min, the corresponding values were 449, 395, 108, and 63 μM. $EC_1$ values, and therefore ferric reducing ability, were lower at longer reaction times as expected from the kinetic behavior of the antioxidants (Pulido, et al. *J. Agric. Food Chem.* 2000, 48, 3396-3402, incorporated herein by reference in its entirety). Using either the FRAP or $EC_1$ values, the order of antioxidant efficiency were the same: compound 1>syringaldehyde>Trolox>ascorbic acid.

TABLE 3

Regression equations with correlation coefficients (R2) of FeSO4 and different antioxidants at various times

| | Linearity tested (μM) | Reaction time (min) | Slope | Intercept | $R^2$ |
|---|---|---|---|---|---|
| Fe(II) | 0-82 | 5 | 0.012 | 0.0031 | 1.0 |
| | | 15 | 0.012 | 0.0176 | 0.996 |
| | | 30 | 0.012 | 0.0113 | 0.996 |
| | | 60 | 0.012 | 0.0102 | 0.997 |
| Compound 1 | 0-2.3 | 5 | 0.163 | −0.0013 | 0.993 |
| | | 15 | 0.175 | 0.0122 | 0.982 |
| | | 30 | 0.182 | 0.0082 | 0.982 |
| | | 60 | 0.190 | 0.0075 | 0.978 |
| Syringaldehyde | 0-1.7 | 5 | 0.062 | −0.0006 | 0.916 |
| | | 15 | 0.081 | 0.0075 | 0.922 |
| | | 30 | 0.101 | −0.0011 | 0.948 |
| | | 60 | 0.111 | −0.0012 | 0.919 |
| Ascorbic Acid | 0-60 | 5 | 0.0238 | −0.0251 | 0.998 |
| | | 15 | 0.0255 | −0.0239 | 0.998 |
| | | 30 | 0.0272 | −0.0362 | 0.998 |
| | | 60 | 0.0305 | −0.0378 | 0.999 |
| Trolox | 0-70 | 5 | 0.0268 | −0.0578 | 0.996 |
| | | 15 | 0.0269 | −0.0548 | 0.996 |
| | | 30 | 0.0269 | −0.0628 | 0.995 |
| | | 60 | 0.0269 | −0.0667 | 0.995 |

TABLE 4

FRAP values relative to Fe(II)

| | FRAP Values at various time (min) | | | |
|---|---|---|---|---|
| Antioxidant | 5 | 15 | 30 | 60 |
| Trolox | 2.2 | 2.2 | 2.2 | 2.2 |
| Ascorbic Acid | 2.0 | 2.1 | 2.3 | 2.5 |
| Syringaldehyde | 5.1 | 6.7 | 8.4 | 9.2 |
| Compound 1 | 13.5 | 14.6 | 15.1 | 15.8 |

According to data obtained from the FRAP assay, the compound 1 showed ~6 and 7 times higher FRAP value than Trolox at 5 and 60 min reaction time, respectively (Table 4). In the FRAP assay, syringaldehyde showed an unusually high FRAP activity. Due to the high FRAP reactivity of syringaldehyde, the relative FRAP ratio of compound 1 to syringaldehyde is small (~2.6 times at 5 min; 1.7 times at 60 min) compared to the DPPH (27 times) and ABTS (8.7 times) assays.

To compare antioxidant capacity with Trolox, the ABTS and DPPH radical scavenging capacity and ferric ion reducing capacity (FRAP) of compound 1, syringaldehyde, and ascorbic acid were compared relative to Trolox, and the values are presented in Table 5. The antioxidant capacity of ascorbic acid was similar to Trolox with all three assays. Syringaldehyde, on the other hand, showed a highly variable value. While the DPPH assay showed it was 5.6 times weaker than Trolox, the ABTS assay showed it was similar to Trolox. The FRAP method showed its antioxidant capacity to be twice as strong as Trolox at 5 min but 4 times better at 60 min. In comparison, more consistent results were obtained with compound 1. All three methods showed it to be a significantly stronger antioxidant than its monomer (syringaldehyde), Trolox, or ascorbic acid. The compound 1 showed 4.9 (DPPH), 8.5 (ABTS), 6.1 (FRAP 5 min), and 7.2 (FRAP 60 min) times higher antioxidant capacity than Trolox. It was also 4.9 (DPPH), 9.4 (ABTS), 6.7 (FRAP 5 min), and 6.5 (FRAP at 60 min) times better than ascorbic acid and 27 (DPPH), 8.7 (ABTS), 2.7 (FRAP 5 min), and 1.7 (FRAP at 60 min) times more potent than syringaldehyde.

TABLE 5

Antioxidant capacity of antioxidants relative to Trolox

| | Antioxidant Capacity Relative to Trolox | | | |
|---|---|---|---|---|
| | | | FRAP | |
| Antioxidant | DPPH | ABTS | 5 min | 60 min |
| Trolox | 1 | 1 | 1 | 1 |
| Ascorbic Acid | 1 | 0.90 | 0.91 | 1.1 |
| Syringaldehyde | 0.18 | 0.98 | 2.3 | 4.2 |
| Compound 1 | 4.9 | 8.5 | 6.1 | 7.2 |

In summary, the ranking of the antioxidants, as measured by various assays, was found to be as follows:
DPPH assay: compound 1>ascorbic acid and Trolox>syringaldehyde;
ABTS assay: compound 1>Trolox>syringaldehyde>ascorbic acid;
FRAP (5 min): compound 1>syringaldehyde>Trolox>ascorbic acid; and
FRAP (60 min): compound 1>syringaldehyde>ascorbic acid>Trolox.

Example 10

Enzyme Inactivation

Lysozyme and carbonic anhydrase (100 μg/mL) were incubated at 37° C. with 20 mM AAPH in phosphate buffered saline. The incubations were run with or without antioxidants (compound 1, syringaldehyde, Trolox, and ascorbic acid). Final concentrations of all antioxidants were 50 μM. Antioxidant solutions were made in 10% (v/v) methanol, except ascorbic acid was made in water. At various time intervals, 5 μL samples were removed to assay for lysozyme and 10 μL samples were taken to assay for carbonic anhydrase activities. Lysozyme assays were carried out at room temperature (25° C.) by monitoring the loss of apparent absorbance at 450 nm, which results from the addition of lysozyme to a suspension of lyophilized *M. lysodeikticus* in 67 mM phosphate buffer, pH 6.2. Carbonic anhydrase activity was measured by monitoring the hydrolysis of 1 mM para-nitrophenyl acetate in 50 mM Tris sulfate, pH 7.5 at 400 nm and 25° C. Coefficient of variation for within-run % recoveries was >20%.

Figure 19:
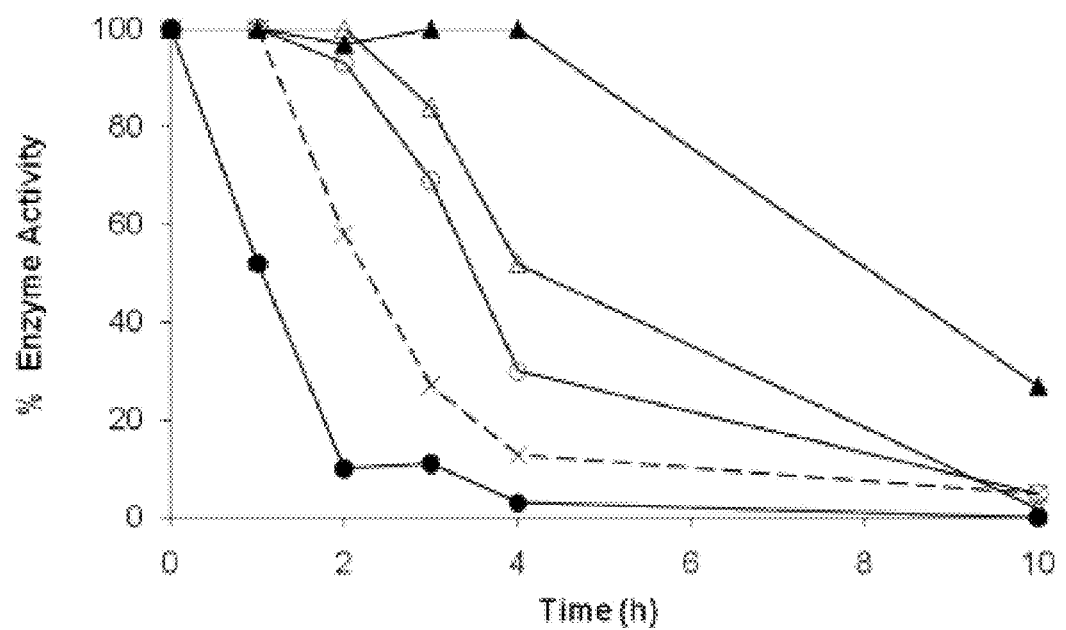
FIG. 19 is a graph of percent lysozyme enzyme activity versus time, showing the protective effect of various antioxidants against AAPH-induced inactivation of lysozyme. Samples include Trolox (open circles), ascorbic acid or control without methanol (closed circles), syringaldehyde (open triangles), compound 1 (closed triangles), and control with methanol (dashed line).
Figure 20:
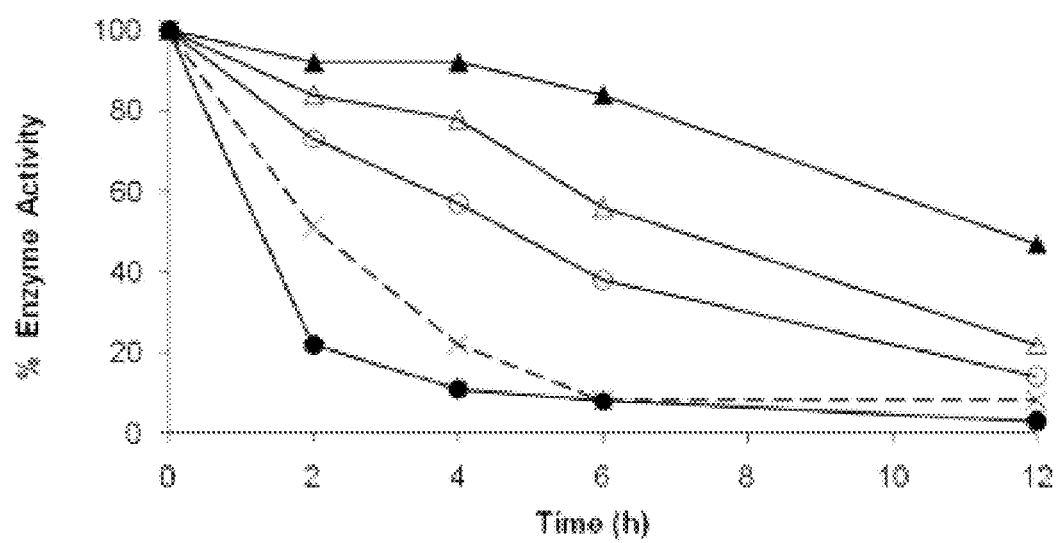
FIG. 20 is a graph of percent carbonic anhydrase II enzyme activity versus time, showing the protective effect of various antioxidants against AAPH-induced inactivation of lysozyme. Samples include Trolox (open circles), ascorbic acid or control without methanol (closed circles), syringaldehyde (open triangles), compound 1 (closed triangles), and control with methanol (dashed line).

In the presence of the antioxidants, boldine and Trolox, AAPH-induced inactivation of lysozyme was delayed. FIG. 19 shows a similar protective effect on lysozyme against AAPH inactivation by the compound 1. When the enzyme was incubated with AAPH only, there was a rapid loss in activity within 2 h. Ascorbic acid (made in water) at 50 μM was ineffective in protecting the enzyme under these conditions, showing a similar curve as the control (lysozyme with AAPH). Both Trolox and syringaldehyde showed a lag phase of about 2 h before the rapid loss of enzyme activity. On the other hand, the compound 1 showed a protective effect of approximately 4 h under similar conditions. It should also be noted that lysozyme maintained about 30% activity even after 10 h incubation with AAPH in the presence of compound 1. In comparison, the enzyme showed negligible activity in the presence of Trolox and syringaldehyde under the same conditions. The effectiveness of the antioxidants towards lysozyme protection was in the order: compound 1>syringaldehyde>Trolox>ascorbic acid (FIG. 19). The protective effect of compound 1 was also tested on another protein, carbonic anhydrase II. This protein is twice as large as lysozyme but has no disulfide bonds. A similar trend was observed for both lysozyme and carbonic anhydrase (FIG. 20). Appropriate blanks without enzyme and controls were also run for the two proteins. Except for the methanol used to reconstitute the compound 1, syringaldehyde, and Trolox, none of the other controls or blanks showed any effect on enzyme recovery. The control with methanol (final concentration 10%, v/v), showed some suppression of AAPH-induced lysozyme inactivation (FIGS. 19 and 20).

The results showed that appropriate assembly of small antioxidants with one another can yield large and more potent designer antioxidants. It was discovered that (1) assembling multiple phenol rings with electron donating groups ortho (methoxy) and para (benzylic group) to the hydroxyl group could enhance H atom donating potential (or electron) of hydroxyl groups and dramatically augment antioxidant capacity of its monomeric counterpart and (2) introduction of benzylic hydrogens para to the phenolic hydroxyl groups could result in enhanced antioxidant potential. The syringaldehyde tetramer (compound 1) was a far superior antioxidant than Trolox, ascorbate, and syringaldehyde.

Example 11

Synthesized G1 Dendrimers

The G1 dendrimers shown in Table 6 were synthesized as described above.

TABLE 6

Synthesized G1 dendritic antioxidants.

| G1 Dendrimer | Structure |
|---|---|
| Syringaldehyde Building Block-TREN Core (G1, MW = 1142) | 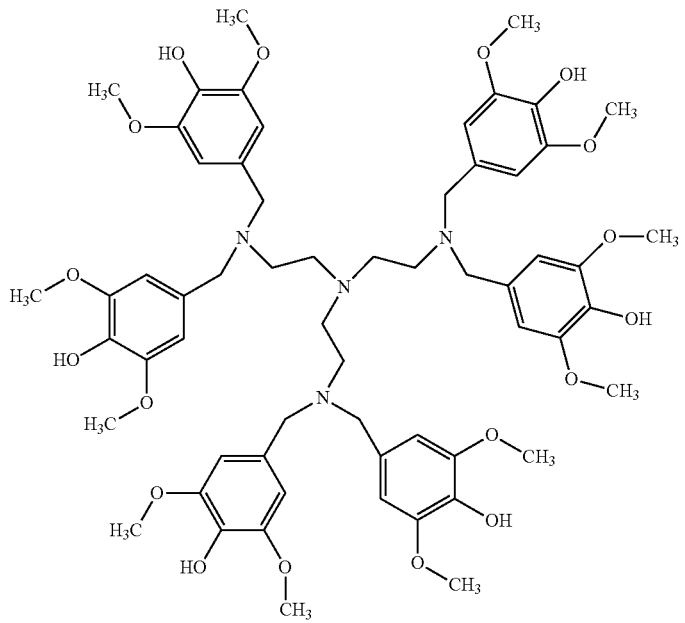 |

TABLE 6-continued
Synthesized G1 dendritic antioxidants.
| G1 Dendrimer | Structure |
| --- | --- |
| Vanillin Building Block-TREN core (G1) | 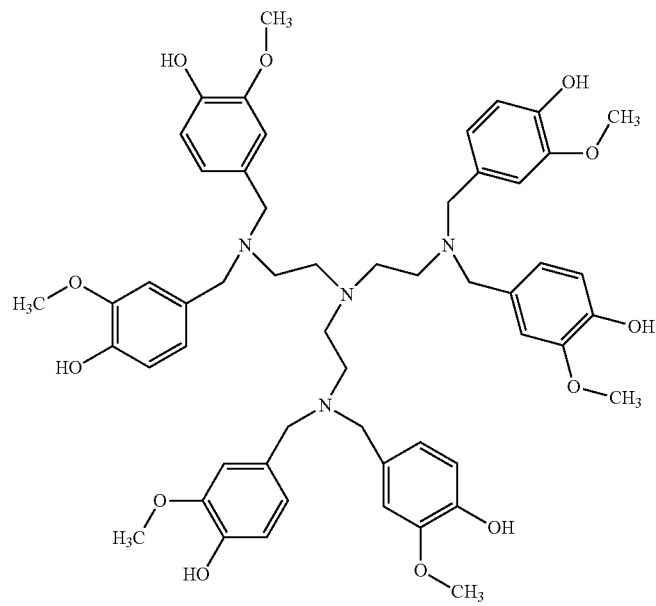 [SMILES: COc1cc(CN(CCN(CCN(Cc2ccc(O)c(OC)c2)Cc2ccc(O)c(OC)c2)CCN(Cc2ccc(O)c(OC)c2)Cc2ccc(O)c(OC)c2)Cc2ccc(O)c(OC)c2)ccc1O] |
| Syringaldehyde Building Block-4-Aminomethylbenzylamine Core (G1, MW = 800) | 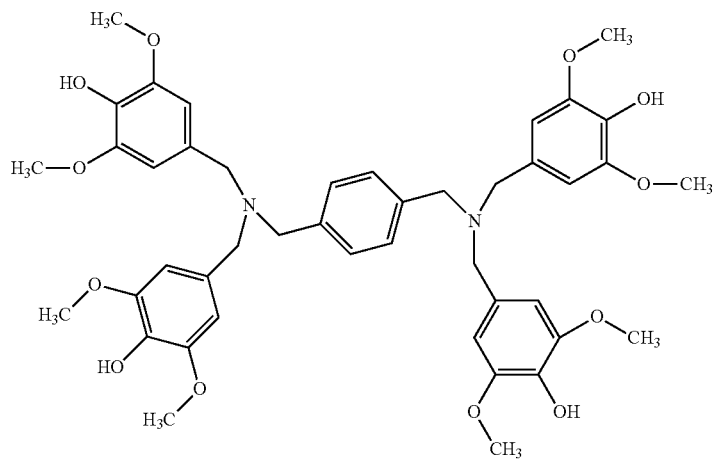 |
| Vanillin Building Block-4-Aminomethylbenzylamine Core Core (G1, MW = 680) | 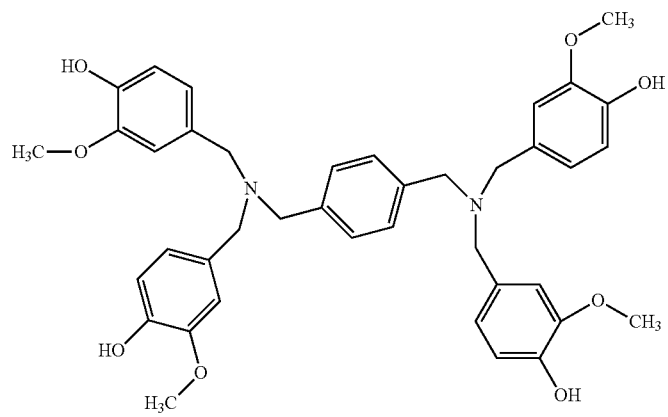 [SMILES: COc1cc(CN(Cc2ccc(CN(Cc3ccc(O)c(OC)c3)Cc3ccc(O)c(OC)c3)cc2)Cc2ccc(O)c(OC)c2)ccc1O] |

TABLE 6-continued

Synthesized G1 dendritic antioxidants.

| G1 Dendrimer | Structure |
| --- | --- |
| 5-Iodovanillin Building Block-4-Aminomethylbenzylamine Core (G1, MW = 1184) | 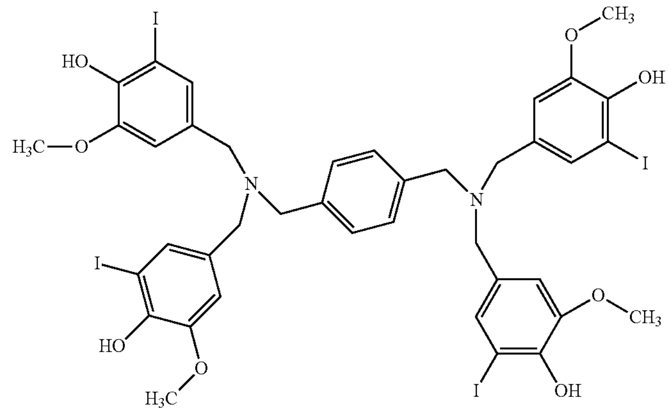 [SMILES: COc1cc(CN(Cc2ccc(CN(Cc3cc(I)c(O)c(OC)c3)Cc3cc(I)c(O)c(OC)c3)cc2)Cc2cc(I)c(O)c(OC)c2)cc(I)c1O] |
| Syringaldehyde Building Block-1,6-diaminoethyleneglycole core (G1, MW = 812) | 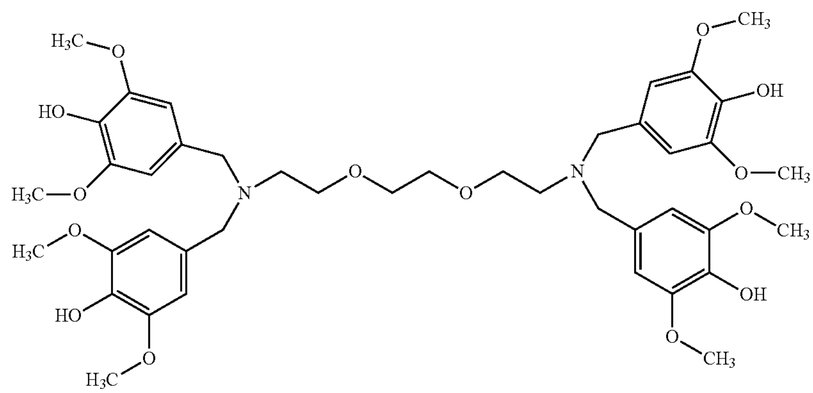 |
| Syringaldehyde Building Block-1,6-diaminohexane Core (G1, MW = 780) | 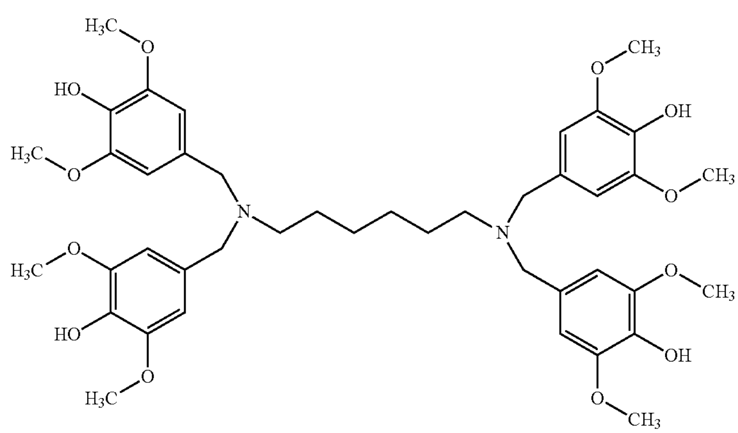 |
| 3,5-di-hydroxybenzaldehyde Building Block-4-Aminomethyl-benzylamine Core (G1, MW = 624) | 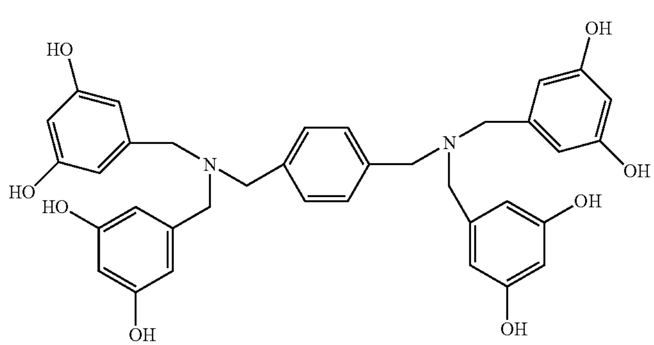 [SMILES: Oc1cc(O)cc(CN(Cc2ccc(CN(Cc3cc(O)cc(O)c3)Cc3cc(O)cc(O)c3)cc2)Cc2cc(O)cc(O)c2)c1] |

TABLE 6-continued

Synthesized G1 dendritic antioxidants.

| G1 Dendrimer | Structure |
|---|---|
| Cinnamicaldehyde Building Block-4-aminomethylbenzylamine Core (G1, MW = 952) | 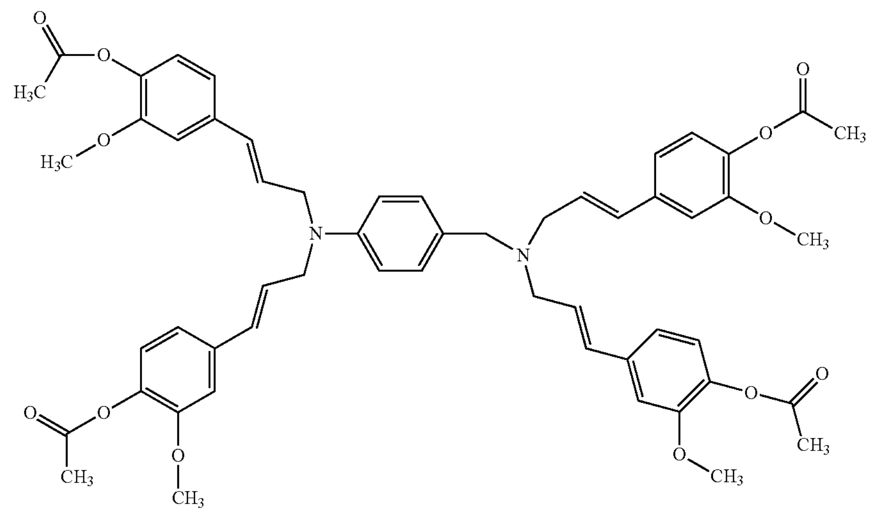 [SMILES: COc1cc(/C=C/CN(C/C=C/c2ccc(OC(C)=O)c(OC)c2)Cc2ccc(N(C/C=C/c3ccc(OC(C)=O)c(OC)c3)C/C=C/c3ccc(OC(C)=O)c(OC)c3)cc2)ccc1OC(C)=O] |

Example 12

Synthesis of G1 Dendrimers Compound 2 and Compound 3

Two G1 dendrimers, compound 2 and compound 3, were synthesized similar to the scheme for compound 1, as shown in FIG. 14, from vanillin and 5-iodovanillin building blocks, respectively. In FIG. 14, (a) is 4-aminomethylbenzylamine, Na(OAc)$_3$BH, 1,2-dichloroethane; (b) is TBDMS-Cl, triethylamine, CH$_2$Cl$_2$, 0° C.; and (c) is n-Bu$_4$NF, THF. The presence of aldehyde groups in the phenol building blocks allowed their ready conversion into dendritic forms via covalent attachment to a core molecule with two or more amino groups. 4-aminomethylbenzylamine was used as the core for all three compounds, thus having the same core and branching points but differing in their terminal phenol rings. Aldehyde groups of building blocks were reacted with the amino groups of the core, forming imines that were subsequently reduced to amines. Sodium triacetoxyborohydride (Na(OAc)$_3$BH) was found to be an appropriate reducing agent for amination. Although some aldehydes in the building block were reduced to an alcohol, it was far more efficient than other reducing agents like NaCNBH$_3$. In order to decrease aldehyde reduction, the building block and Na(OAc)$_3$BH were added in a stepwise manner so that aldehyde exposure to Na(OAc)$_3$BH was minimized. Na(OAc)$_3$BH gave good reaction yields in the solvent, 1,2-dichloroethane. In compound 1 synthesis, both syringaldehyde and 4-aminomethylbenzylamine dissolved slowly in 1,2-dichloroethane and afforded high reaction yield (over 80%). However, vanillin and 5-iodovanillin were not very soluble in the solvent. They were therefore protected with TBDMS-Cl to increase their solubility in 1,2-dichloroethane, contributing to improved yields for both compound 2 and compound 3 (FIG. 14).

Compound 1 has four peripheral phenols with two strong electron-donating methoxy groups per ring. Compound 2 is similar to, but has only one electron-donating substituent on each phenol. Compound 3 resembles 2 except for the presence of an iodo group on each ring.

Example 13

Antioxidant Activity of Compound 2 and Compound 3

Figure 21:
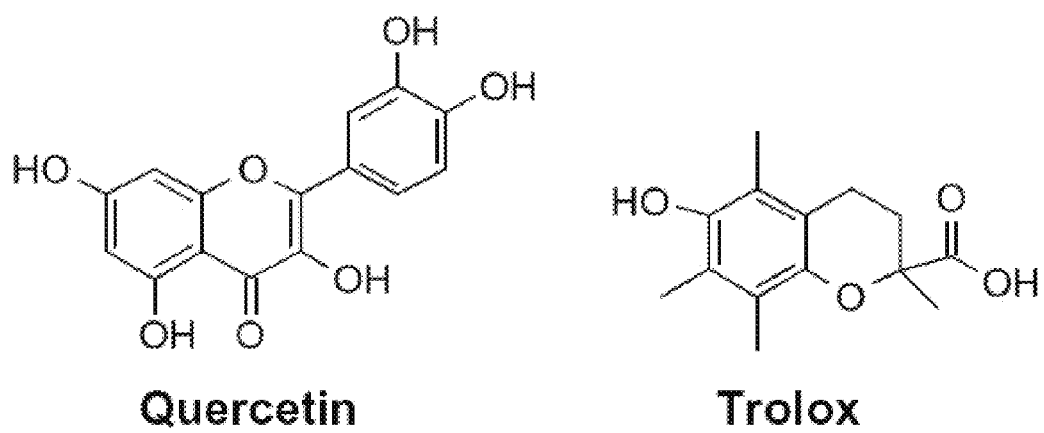
FIG. 21 are structures of quercetin and Trolox antioxidants used as controls.

The antioxidant activity of compound 2 and compound 3 was compared to the antioxidant activity of compound 1 as well as the antioxidants quercetin (a flavonoid) and Trolox (a water-soluble vitamin E analog), shown in FIG. 21.

Figure 22:
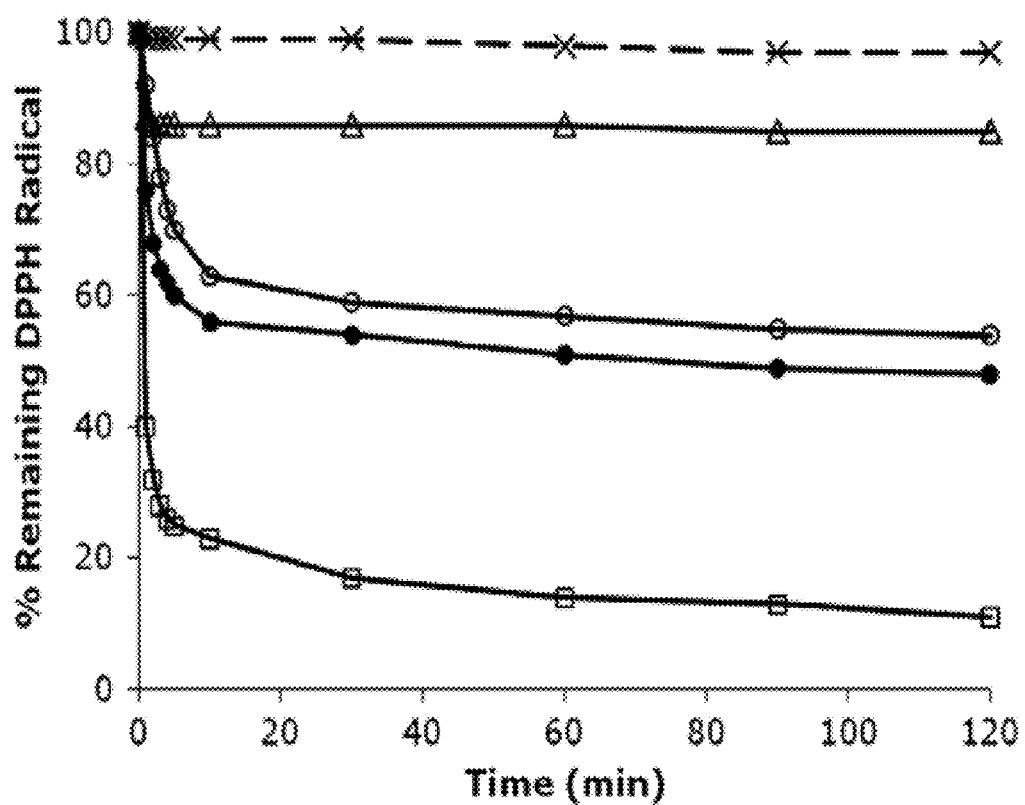
FIG. 22 is a graph of DPPH reaction kinetics of dendritic antioxidants: Control with methanol (X, dashed), compound 1 (□), compound 2 (•), compound 3 (○), Trolox (Δ). All antioxidant concentrations are 5 μM.

Antioxidant capacity of the compounds was assessed by the DPPH assay (Brand-Williams, et al. *Lebensm. Wiss. Technol.* 1995, 28, 25, incorporated herein by reference in its entirety). All three dendritic compounds 1, 2, and 3 showed hyperbolic kinetic curves with rapid radical scavenging within 10 min followed by a slower phase (FIG. 22). In FIG. 22, control with methanol is (X, dashed); compound 1 is (□), compound 2 is (•), compound 3 is (○), and Trolox (Δ). All antioxidant concentrations were 5 µM. Quercetin also displayed similar kinetics (data not shown). Trolox, on the other hand reached plateau values in less than a minute. The IC$_{50}$ values, determined at 120 min, were 3.7, 6.0, 6.0, 9.0, and 27.6 1 M for compounds 1, 2, 3, quercetin, and Trolox, respectively. All three dendritic antioxidants were stronger than quercetin and Trolox. Compound 1 was the most potent DPPH radical scavenger while compounds 2 and 3 showed identical antioxidant capacity. Compound 1 was stronger than 2 probably due to the presence of an additional electrondonating substituent (methoxy) ortho to the phenolic hydroxyl group. Based on IC$_{50}$ values of compounds 2 and 3, the presence of iodo groups did not diminish the radical scavenging capacity. The starting materials used for syntheses of compounds 1-3 showed negligible DPPH activity (IC$_{50}$ values of syringaldehyde, vanillin, 5-iodovanillin and 4-aminomethylbenzylamine>100 1 M).

The antioxidant activity of compounds 1, 2, and 3 towards biomolecules was examined by studying their ability to protect LDL, fatty acid, and DNA from free radicals. For LDL, AAPH was used to induce free radical damage. AAPH was used instead of copper ($Cu^2$) ion for LDL oxidation so that the free radical scavenging activity of the antioxidants could be measured without any pro-oxidant interference caused by metal ions (Salah, N. et al. *Arch. Biochem. Biophys.* 1995, 322, 339, incorporated herein by reference in its entirety). All solutions were made in ultra-pure water.

Figure 23:
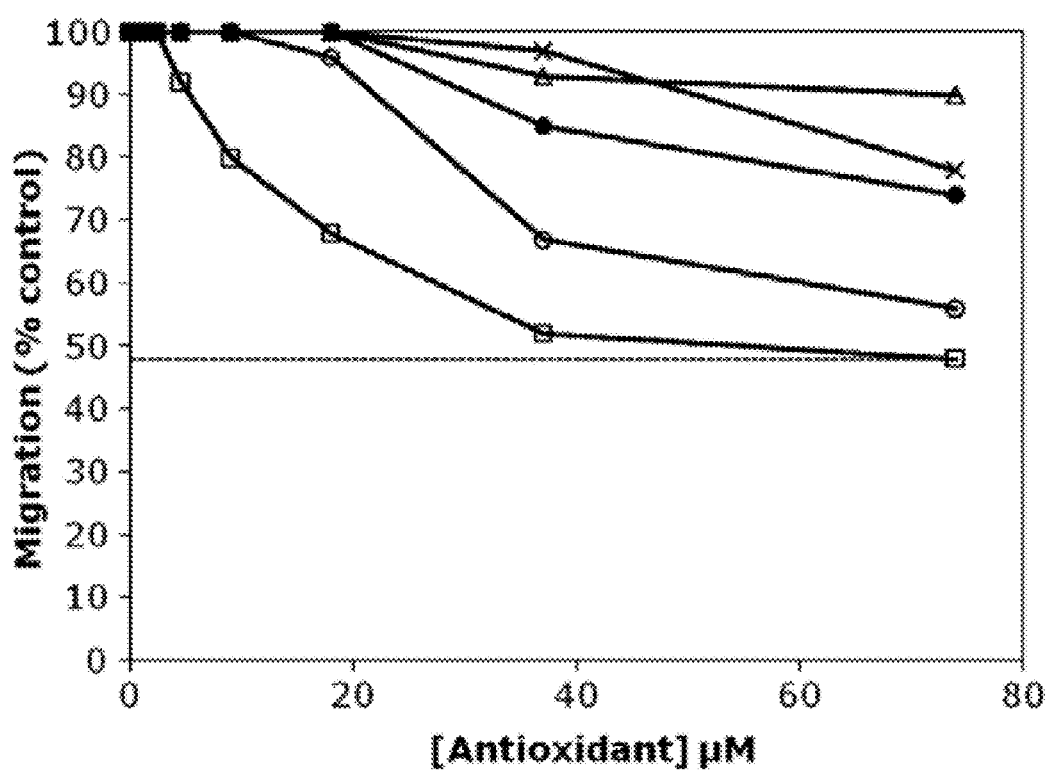
FIG. 23 is a graph of the migration of oxidized LDL in an electrophoresis gel. AAPH oxidized LDL without any added antioxidant is expressed as 100%. Native LDL showed a mobility of ~50% that of oxidized lipoprotein (dashed line). Migration of oxidized LDL in the presence of various antioxidants including compound 1 (□), compound 2 (•), compound 3 (○), Trolox (Δ), and quercetin (X) is shown.

LDL oxidized with 10 mM AAPH (18 h, 37° C.) showed increased anodic migration on agarose gels (expressed as 100% migration, FIG. 23) compared to un-oxidized native lipoprotein (dashed line, ~50% migration of oxidized LDL, FIG. 23). In FIG. 23, AAPH oxidized LDL without any added antioxidant was expressed as 100%, native LDL showed a mobility of ~50% that of oxidized lipoprotein (dashed line), and migration of oxidized LDL in the presence of various antioxidants including compound 1 (□), compound 2 (•), compound 3 (○), Trolox (Δ), and quercetin (x) is shown. Protection of LDL from AAPH free radicals by the antioxidant decreased the anodic shift in a dose-dependent manner (FIG. 23). Compound 1 was the most efficient in protecting LDL followed by 3, 2, quercetin, and Trolox. Although compound 2 and compound 3 showed identical DPPH values, the iodinated dendrimer (compound 3) displayed better LDL protection than compound 2. The increased hydrophobicity of compound 3 may be partly responsible for its improved LDL protection over compound 2. The starting materials for compounds 1, 2, and 3 showed no LDL protection under these conditions.

Figure 24:
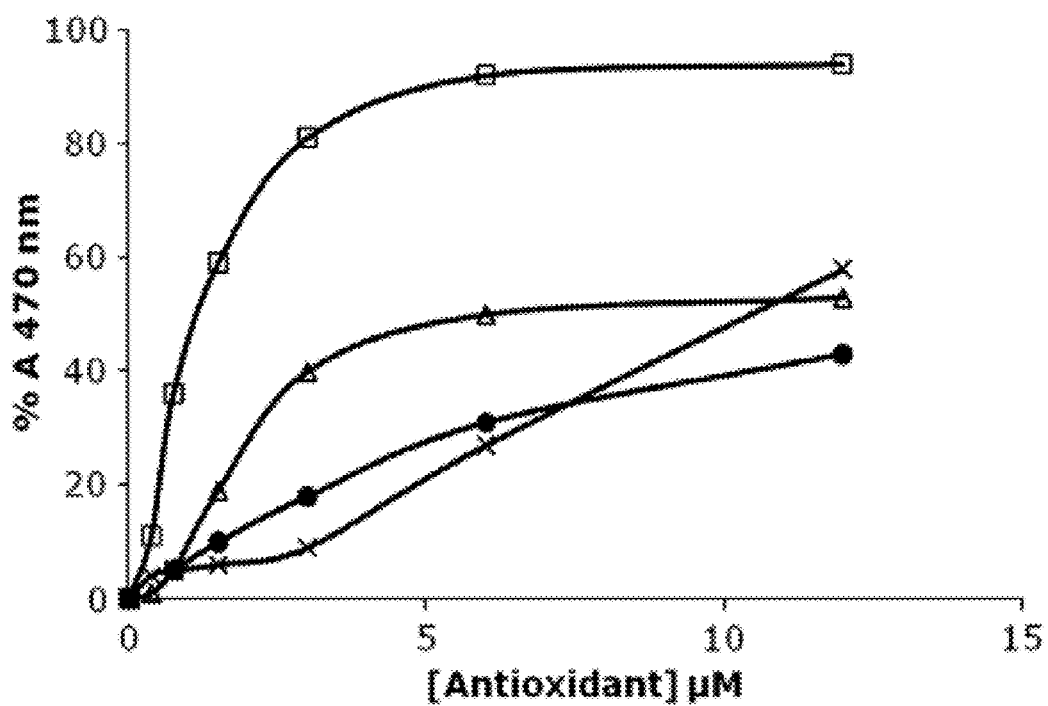
FIG. 24 is a graph of % $A_{470\,nm}$ versus antioxidant concentration for a beta-carotene-linoleate assay. Protection of linoleic acid from oxidation by various antioxidants is shown for compound 1 (□), compounds 2 and 3 (•), quercetin (x), and Trolox (Δ).

The ability of the dendritic antioxidants 1, 2, and 3 to protect linoleic acid against free radical damage was examined by the beta-carotene-linoleate model (Jayaprakasha, G. K., et al. *Food Chem.* 2001, 73, 285, incorporated herein by reference in its entirety). In the absence of an antioxidant, hydroperoxides formed from linoleic acid oxidation bleach the highly unsaturated beta-carotene by a free-radical-mediated phenomenon. The bleaching of the reddish-orange color of beta-carotene was monitored at 470 nm in the presence of various concentrations of antioxidant. The % absorbance (corrected for control without antioxidant) was determined at each antioxidant concentration after incubation at 50° C. for 180 min. The % $A_{470\,nm}$ values were determined as follows: % $A_{470\,nm} = [(A_{t(180\,min)}/A_{t(0\,min)}) \times 100] - [(A_{c(180\,min)}/A_{c(0\,min)}) \times 100]$, wherein $A_{t(180\,min)}$=absorbance at 470 nm of antioxidant sample incubated at 50° C. for 180 min, $A_{t(0\,min)}$=absorbance at 470 nm of antioxidant sample incubated at 50° C. for 0 min, $A_{c(180\,min)}$=absorbance at 470 nm of control sample (without antioxidant) incubated at 50° C. for 180 min, and $A_{c(0\,min)}$=absorbance at 470 nm of control sample (without antioxidant) incubated at 50° C. for 0 min. Results shown in FIG. 24 demonstrate that all three compounds 1, 2, and 3 were effective in protecting linoleic acid oxidation. In FIG. 24, protection of linoleic acid from oxidation by various antioxidants is shown for compound 1 (□), compounds 2 and 3 (•), quercetin (x), and Trolox (Δ). Compound 1 was the most effective. Compounds 2 and 3 were about twice weaker than compound 1. Under the concentrations used in the experiment, compound 2 and compound 3 showed identical activities with one another and were quite similar to quercetin. In comparison, Trolox was more effective than compounds 2 and 3 (and quercetin) at lower concentrations. Among the starting materials, 4-aminomethylbenzylamine and syringaldehyde showed 16% and 12% $A_{470\,nm}$ at 12 μM after 180 min incubation, respectively while vanillin and 5-iodovanillin exhibited <5%.

Figure 25:
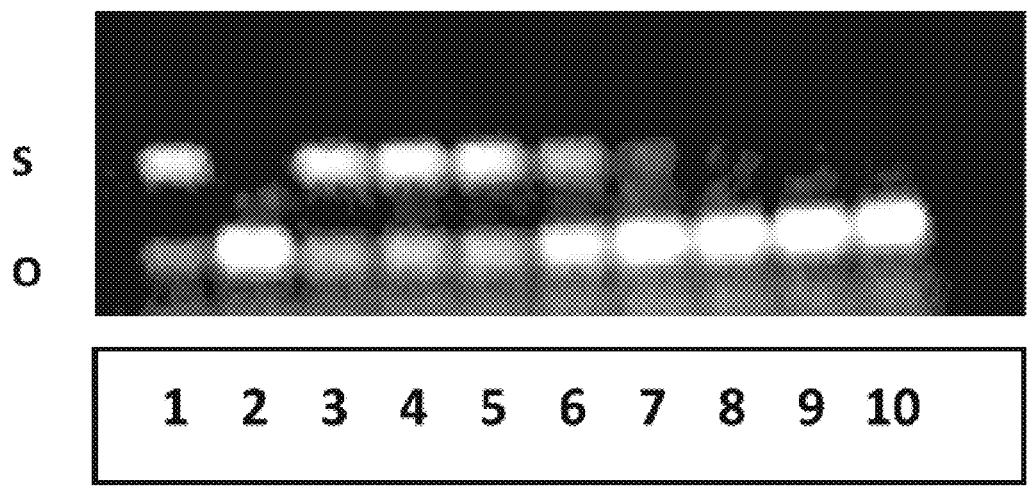
FIG. 25 is an image of a gel showing DNA migration indicating protection of DNA against AAPH-induced oxidation by compound 1.

The effectiveness of the three compounds to protect DNA from AAPH damage was also determined. The plasmid DNA pBR 322 was incubated with AAPH (final concentration 10 mM) at 37° C. for 4 h with or without antioxidants (final concentrations, 0.35-45 μM), after which the samples were subjected to agarose electrophoresis (Sakihama, Y., et al. *Toxicology* 2002, 177, 67, incorporated herein by reference in its entirety). An example of the gel obtained with compound 1 is shown in FIG. 25. In FIG. 25, lane 1 is native DNA, and lanes 2-10 are AAPH-oxidized DNA with 0, 45, 23, 11, 5, 3, 1.5, 0.7, and 0.35 μM antioxidant, respectively. In the absence of AAPH, pBR 322 was mostly in its supercoiled (S) form (small amount of open circular, O, form was also visible, lane 1 FIG. 25). After reaction with AAPH, the DNA was transformed almost entirely into its open circular form (lane 2, FIG. 25). Compound 1 showed the best protection. In the presence of 11-45 μM of 1, DNA was well protected (the S band intensity was similar to control without AAPH, lanes 3-5, FIG. 25). Quercetin showed similar protection (data not shown). Some protection was also obtained for compound 1 at 5 μM (lane 6, FIG. 25) but not with quercetin (data not shown). No protection was obtained for both compound 1 and quercetin below 5 μM (lanes 7-10, FIG. 25). In case of compound 2, some protection was only observed at ≥45 μM. Lower concentrations did not show any protection. Compound 3 as well as Trolox were ineffective at all concentrations used in the experiment (0.35-45 μM). The starting materials for dendrimer synthesis did not show any DNA protection under these conditions.

Figure 26:
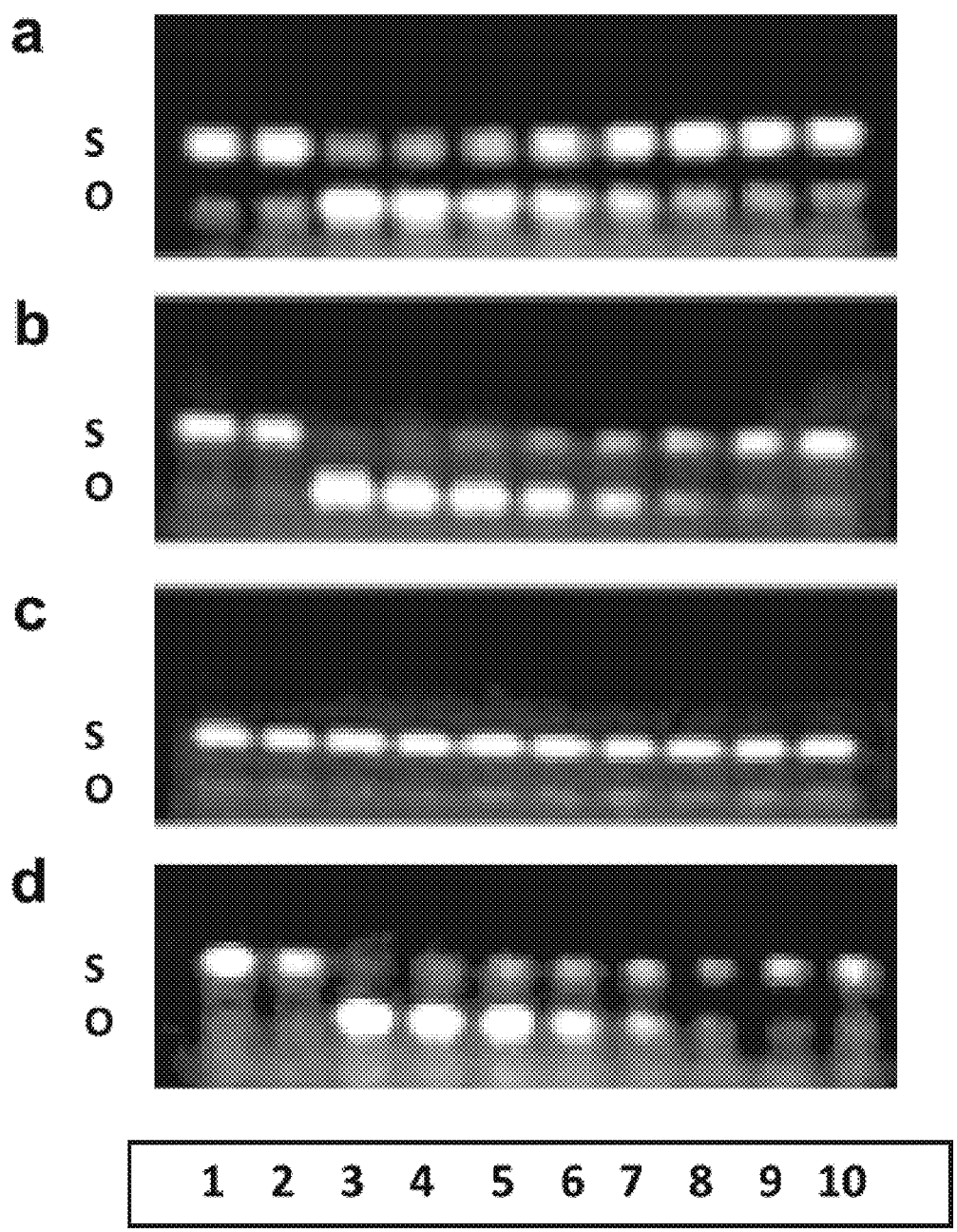
FIG. 26 is an image of a gel showing DNA migration indicating pro-oxidant activity of antioxidants. (a) compound 1; (b) quercetin; (c) compound 3; (d) Trolox.

Antioxidants may also exhibit pro-oxidant activity in the presence of metal ions, which can lead to damage of biomolecules. The pro-oxidant effect of compounds 1, 2, and 3 was examined by oxidation of DNA with copper (II) ion. pBR 322 was incubated with 10 μM $Cu^{2+}$ at 37° C. for 1 h in the presence of compound 1, 2, or 3 (final concentrations between 0.35 and 45 μM). Examples of gels obtained for compound 1, 3, quercetin, and Trolox are shown in FIG. 26. DNA damage was clearly observed with compound 1 and quercetin at concentrations between 11 and 45 μM (lanes 3-5, FIG. 26). In FIG. 26 shows pro-oxidant activity of (a) compound 1; (b) quercetin; (c) compound 3; (d) and Trolox. Lane 1 is native DNA, and lanes 2-10 are $Cu^{2+}$-oxidized DNA with 0, 45, 23, 11, 5, 3, 1.5, 0.7, and 0.35 μM antioxidant, respectively.

However, quercetin exhibited a more pronounced pro-oxidant effect than compound 1 between 3 and 5 μM (lanes 6 and 7, FIG. 26). For compound 2, a slight pro-oxidant effect was seen at 23 and 45 μM (data not shown). Compound 3, under similar conditions did not show any appreciable pro-oxidant effects at the concentrations tested. Trolox under these conditions also showed a strong pro-oxidant effect equivalent to quercetin. The starting materials did not show any pro-oxidant effect on DNA under these conditions.

Three dendritic polyphenols were synthesized (compounds, 1, 2, and 3), all of which showed strong antioxidant capacity. Among the three dendrimers, quercetin, and Trolox, the syringaldehyde-based dendrimer (compound 1) was the most potent and displayed the best protection for LDL, linoleate, and DNA against free radical attack. Its pro-oxidant activity was stronger than the other two dendrimers (compound 2 and compound 3) but weaker than quercetin and Trolox. All three dendrimers showed far superior DPPH radical scavenging activity compared to their individual as well as sum of their starting materials (core and building blocks), suggesting potential dendritic effect. In addition, they were also more effective in protecting LDL, linoleic acid, and DNA from free radical damage than their starting materials. It was discovered that dendritic polyphenols, even at the G1 level, may offer a novel and exciting class of molecules with beneficial antioxidant properties.

Example 14

Syntheses of G1 Dendrimers, Compound 4 and Compound 5

Figure 27:
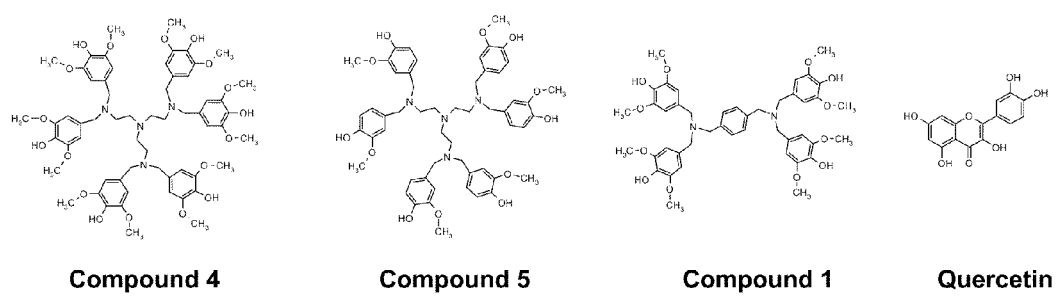
FIG. 27 are structures of compounds 4, 5 and 1.

G1 antioxidants, compound 4 and compound 5, were prepared with interior amines having potential metal chelation property surrounded by a peripheral layer of phenol rings that are efficient radical scavenging groups, with the idea that antioxidant dendrimers of this design may have beneficial antioxidant potential with reduced undesirable pro-oxidant activity towards DNA. Structures of the two newly synthesized syringaldehyde and vanillin-based dendrimers with a tris(2-aminoethyl)amine (TREN) core (compound 4 and compound 5) are shown in FIG. 27.

Figure 28:
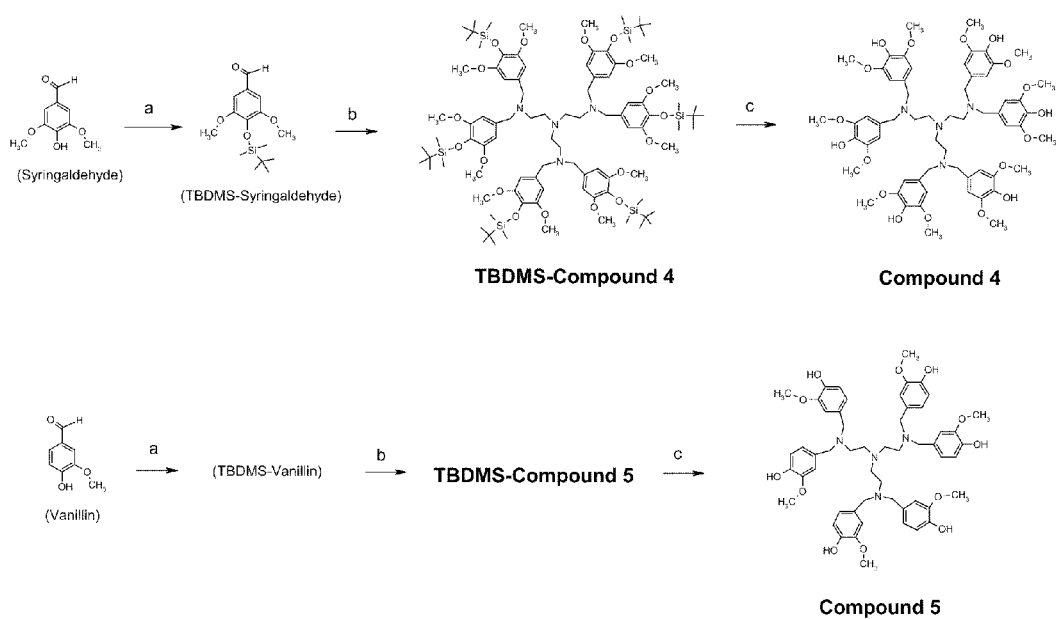
FIG. 28 is a scheme for the syntheses of compounds 4 and 5.

Syntheses of compounds 4 and 5 were initiated by protecting building blocks (syringaldehyde and vanillin) with tert-butoxydimethylsilyl chloride (TBDMS-Cl) (FIG. 28). Syringaldehyde (8.65 g, 47.52 mmol) and triethylamine (7.5 mL, 53.81 mmol) were dissolved in dichloromethane. TBDMS-Cl (20 mL, 57.72 mmol) was added dropwise, and the reaction was run at 0° C. Formation of the target compound was monitored with MALDI-TOF. After confirmation of the target product, the solvent was removed on a rotorvap. The resulting substance was dissolved in acetone (5 mL) and mixed with silica gel. The slurry was dried and the mixture was purified by silica gel column chromatography using a gradient hexane-ethyl acetate solvent system (50:1→25:1). Yield of the TBDMS-protected syringaldehyde was as follows: 13.89 g (98%); $R_f$ value: 0.75 (hexane-ethylacetate=1:1); $^1$H-NMR (300 MHz, CDCl$_3$, Me$_4$Si) δ 0.15 (s, 6H) 1.00 (s, 9H) 3.86 (s, 6H) 7.09 (s, 2H) 9.82 (s, 1H); $^{13}$C-NMR (75 MHz, CDCl$_3$, Me$_4$Si) δ 19.0, 25.9, 56.0, 106.9, 129.5, 140.8, 152.2, 191.3; MS: m/z 297 [M+H$^+$]. Yield of the TBDMS-protected vanillin was as follows: yield 96%; $R_f$=0.59 (hexane:ethyl acetate=5:1); $^1$H-NMR (300 MHz, CDCl$_3$, Me$_4$Si) δ 0.17 (s, 6H, 2×CH$_3$), 0.98 (s, 9H, C(CH$_3$)$_3$), 3.84 (s, 3H, OCH$_3$), 6.93 (d, J=8.1 Hz, 1H, C$_5$—H), 7.33 (dd, 1H, J=7.95 Hz and J=1.95 Hz, C$_2$—H), 7.37 (d, 1H, J=1.5 Hz, C$_6$—H), 9.82 (s, 1H, CHO); $^{13}$C-NMR (75 MHz, CDCl$_3$, Me$_4$Si) δ −4.3 (2×CH$_3$), 18.7 (C(CH$_3$)$_3$), 25.8 (C(CH$_3$)$_3$), 55.6 (OCH$_3$), 110.2 (C$_2$), 120.9 (C$_5$ and C$_6$), 126.4 (C$_1$), 131.1 (C$_4$), 151.5 (C$_3$), 191.2 (CHO).

The protected building blocks were then attached to the amino groups of TREN via their aldehyde groups. The three resulting unstable imine bonds were subsequently reduced with sodium triacetoxyborohydride (Na(OAc)$_3$BH) to form secondary amines which further react with additional aldehyde groups, eventually forming tertiary amines after reduction by Na(OAc)$_3$BH. Unlike other amine alkylation using alkyl halide (which usually produce mixtures containing species ranging from primary amine to quaternary ammonium), the reaction between amine and aldehyde can only form a tertiary amine as an end product. Hence, it was an attractive method to form branches in a controlled manner, producing a well-defined dendritic structure. Although Na(OAc)$_3$BH has been reported to be an efficient reductant for imine and iminium bonds, we found that its selective reduction of these groups over aldehyde was poor. The arylaldehydes became reduced to their corresponding alcohols fairly rapidly when all reagents were mixed together in one pot. To avoid this problem, three equivalents of TBDMS-protected building block was first reacted with one equivalent of TREN core and the reaction was allowed sufficient time (>5 h) before addition of Na(OAc)$_3$BH. This was to ensure that the aldehyde reacted with three amino groups first with limited exposure to the reducing agent. After Na(OAc)$_3$BH addition, the reaction was run for at least 24 h before another three equivalents of building block was added. Based on our experience, Na(OAc)$_3$BH worked more efficiently in 1,2-dichloroethane than other solvents like THF and CH$_2$Cl$_2$. Protection of syringaldehyde and vanillin with TBDMS-Cl enhanced percent yield by increasing solubility of the dendrimers 4 and 5 in 1,2-dichloroethane. Both TBDMS-compound 4 and 5 have much better solubility than the corresponding dendrimers in the solvent. Although the water by-product cleaved some of the TBDMS protecting groups, the target compounds with varying number of TBDMS groups remained soluble during the reaction. Prior to column purification, the protecting groups were cleaved with n-tetrabutyl ammonium fluoride in ethanol, affording the antioxidant dendrimers 4 and 5.

More specifically for the synthesis of compound 4 and compound 5 from the protected syringaldehyde and protected vanillin, to a flask were added TREN (0.5 mL, 0.47 g, 3.24 mmol), three equivalents of TBDMS-protected syringaldehyde (2.98 g, 10.07 mmol), and 1,2-dichloroethane (300 mL). The reaction was run for 6 h at room temperature. Na(OAc)$_3$BH (2.07 g, 9.77 mmol) was added and the reaction was run for another 24 h. To the reaction was added another 3 equivalents of TBDMS-protected syringaldehyde (3.01 g, 10.17 mmol). The reaction was stirred for 15 h, followed by Na(OAc)$_3$BH (2.06 g, 9.72 mmol) addition. The reaction was monitored with MALDI-TOF and stopped after 72 h. The reaction solvent (1,2-dichloroethane) was removed under reduced pressure. The resulting residue was dissolved in ethanol and treated with n-Bu$_4$NF (8 mL, 21.87 mmol) to deprotect TBDMS groups. The reaction was stirred overnight and condensed under reduced pressure. After removal of the ethanol under reduced pressure, the resulting residue was partitioned between CHCl$_3$ and water. The CHCl$_3$ layer was dried with MgSO$_4$. Following the removal of MgSO$_4$, the solvent was removed on the rotorvap. The resulting oily substance was purified via silica gel column chromatography using a gradient hexane-ethyl acetate solvent system (8:1→1:4), followed by 100% ethyl acetate and in turn 100% acetone. The product was eluted in acetone.

Yield of compound 4 was as follows: 2.34 g (63%); $R_f$: 0.33 (acetone); $^1$H-NMR (300 MHz, CD$_3$COCD$_3$, Me$_4$Si) δ 2.49 (s, 6H, 3×core N—CH$_2$—CH$_2$—N—), 2.63 (s, 6H, 3×core N—CH$_2$—CH$_2$—N—), 3.41 (s, 12H, 6×Ph-CH$_2$—N—), 3.77 (s, 36H, 12×OCH$_3$), 5.4 (s, 6H, 6×OH), 6.65 (s, 12H, 6×Ph C$_2$—H and C$_6$—H); $^{13}$C-NMR (75 MHz, CD$_3$COCD$_3$, Me$_4$Si) 50.9 (3×core N—CH$_2$—CH$_2$—N—), 52.7 (3×core N—CH$_2$—CH$_2$—N—), 56.4 (12×OCH$_3$), 59.0 (6×Ph-CH$_2$—N—), 106.5 (12×Ph C—H), 130.5 (6×Ph C—CH$_2$—), 135.4 (6×Ph C—OH), 148.4 (12×Ph C—OCH$_3$); MS: m/z 1143.5 [M+H$^+$]. Yield of compound 5 was as follows: 51%; $R_f$=0.21 (acetone); $^1$H-NMR (300 MHz, CD$_3$COCD$_3$, Me$_4$Si) δ 2.45 (t, J=5.7 Hz, 6H, 3×core N—CH$_2$—CH$_2$—N—), 2.57 (t, J=5.4 Hz, core N—CH$_2$—CH$_2$—N—), 3.42 (s, 12H, 6×Ph-CH$_2$—N—), 3.79 (s, 18H, 6×OCH$_3$), 6.75 (s, 12H, 6×Ph C$_2$—H and C$_6$—H), 6.94 (s, 6H, 6×Ph C$_5$—H); $^{13}$C-NMR (75 MHz, CD$_3$COCD$_3$, Me$_4$Si) δ 51.3 (3×core N—CH$_2$—CH$_2$—N—), 53.1 (3×core N—CH$_2$—CH$_2$—N—), 56.1 (6×OCH$_3$), 58.8 (6×Ph-CH$_2$—N—), 112.9 (6×Ph C$_2$—H), 115.3 (6×Ph C$_5$—H), 122.1 (6×Ph C$_6$—H), 131.6 (6×Ph C$_1$—CH$_2$), 146.3 (6×Ph C$_4$—OH), 148.1 (6×Ph C$_3$—OCH$_3$); MS: m/z 963.2 [M+H]$^+$.

Figure 29:
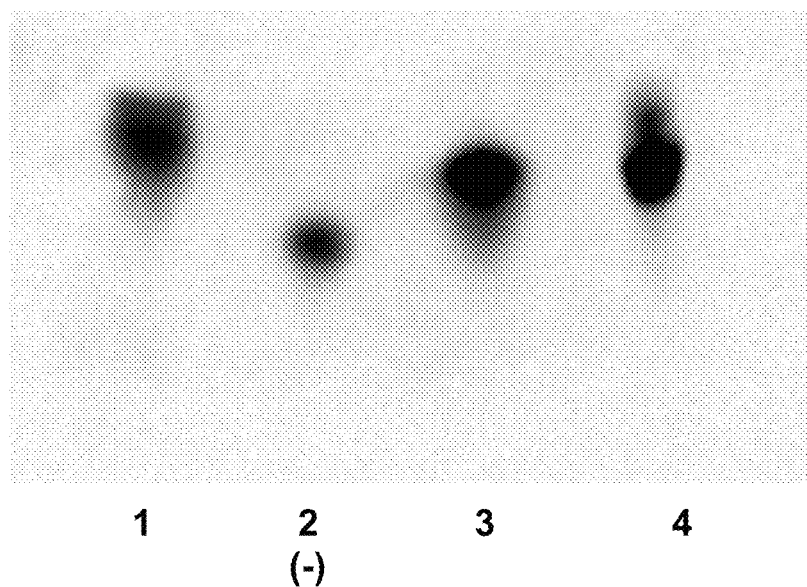
FIG. 29 is an image of a gel showing migration of compound 5, compound 1, and compound 4.

The antioxidant dendrimer compounds 1, 4, and 5 were run under acidic conditions on a 15% PAGE gel and stained with Coomassie Blue (FIG. 29). Each lane contained 10 nmol of antioxidant. All antioxidants produced well-stained bands. For comparison, a generation 4 PAMAM dendrimer with amine surface is shown in lane 1. Compound 5 (lane 2) showed the highest mobility towards the cathode followed by compound 1 (lane 3) and compound 4 (lane 4). In addition to the major band, dendrimer 4 also showed a broad minor band with lower mobility while compound 1 displayed a less intense band with higher mobility. These minor bands probably represented defective target compounds (e.g., species with missing arms).

Example 15

Antioxidant Activity of Compound 4 and Compound 5

DPPH Assay

The free-radical scavenging ability of the antioxidants was evaluated by the DPPH assay, as described above in Example 7. The two TREN-based dendrimers, 4 and 5, showed similar potency ($IC_{50}$ of 2 µM at 120 min) that was slightly better than the previously reported syringaldehyde-based 4-aminomethylbenzylamine core dendrimer compound 1 ($IC_{50}$ of 4 µM at 120 min). Under similar experimental conditions, $IC_{50}$ value for quercetin was 10 µM, Trolox was 30 µM while the starting materials used for syntheses of the antioxidants displayed negligible DPPH activity ($IC_{50}$ values of syringaldehyde and vanillin were >100 µM).

LDL Oxidation

Figure 30:
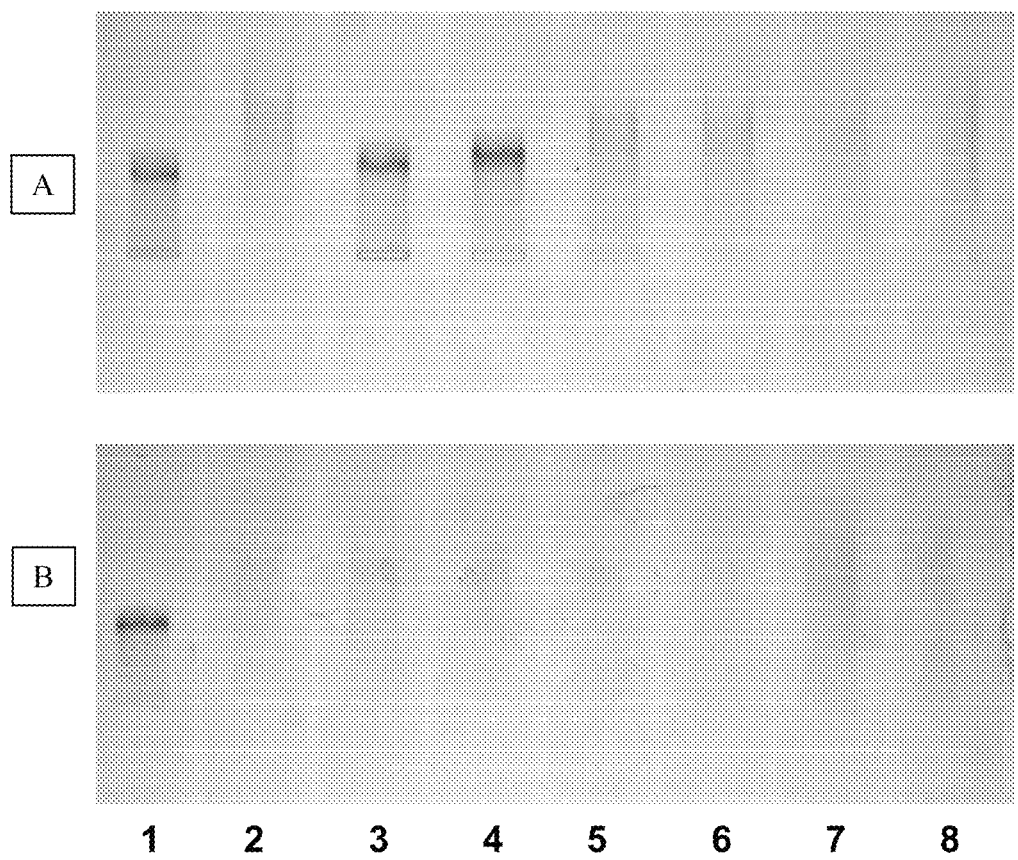
FIG. 30 is an image of agarose gel of LDL treated with AAPH and compound 4 (A), quercetin, or Trolox (B).

The antioxidant activity of the antioxidants towards biomolecules was examined by studying their ability to protect LDL, lysozyme, and DNA from free radicals. For LDL, AAPH was used to induce free radical damage. AAPH was used instead of $Cu^{2+}$ for LDL oxidation so that the free radical scavenging activity of the antioxidants could be measured without any pro-oxidant interference caused by metal ions. The oxidation of human low-density lipoprotein was used as a model for evaluating the ability of the G1 dendrimers as chain-breaking antioxidants for lipid. Oxidation of LDL leads to changes in both the lipid and the protein moieties of the lipoprotein particle. Lipid peroxidation in LDL has been evaluated by a variety of methods. Due to the complexity of events that occur in lipoprotein oxidation, the electrophoretic migration pattern of oxidized LDL is one of the best methods to evaluate the extent of lipoprotein oxidation. LDL was incubated with 20 mM AAPH and increasing concentrations of the G1 dendrimers (0-37 µM in PBS) for 21 h at 37° C. The mixture was then subjected to agarose gel electrophoresis using the Ciba Corning Clinical Electrophoresis System. The agarose gel was stained with Fat Red 7B. The agarose gel obtained with compound 4 is shown in FIG. 30. In FIG. 30A (top), lane 1 is native LDL, and lanes 2-8 are AAPH-oxidized LDL with 0, 37, 18.5, 9, 4.5, 2 and 1 µM compound 4, respectively. In FIG. 30B (bottom), lane 1 is native LDL, and lanes 2-8 are AAPH-oxidized LDL with 0, 37, 18.5, 9, 4.5, 2 and 1 µM quercetin or Trolox, respectively.

Under these conditions, oxidized LDL (lane 2, FIG. 30A), unlike native lipoprotein (lane 1), showed a smear, characteristic of heterogenous species formed as a result of lipoprotein oxidation. The lipoprotein was fully protected against free radical damage at 15 µM and 30 µM of compound 4 (lanes 3 and 4, FIG. 30A). Lower concentrations of compound 4 (lanes 5-8, FIG. 30A) were ineffective. When the LDL was oxidized by AAPH under similar conditions, dendrimer compounds 5 and 1 were effective only at 30 µM (data not shown), while quercetin, Trolox or the starting materials were ineffective at all antioxidant concentrations (1-30 µM) (lanes 3-8, FIG. 30B).

Enzyme Inactivation

Protective effect of the dendritic antioxidants (compounds 4, 5, and 1) on protein was determined using hen egg white lysozyme as a model protein and compared with that of quercetin and Trolox. The lysozyme enzyme (1.8 mg/mL) was incubated with 20 mM AAPH in PBS and 80 µM antioxidant at 37° C. for 24 h. A sample with solvent (methanol) instead of antioxidant was used as a control. After incubation, the sample was diluted with PBS and assayed for lysozyme activity. Lysozyme assays were carried out at room temperature (25° C.) by monitoring the loss of apparent absorbance at 450 nm, which results from the addition of lysozyme to a suspension of lyophilized *M. lysodeikticus* in 67 mM phosphate buffer (pH 6.2). Coefficient of variation for within-run % enzyme activity was <8%. Both compound 4 and compound 5 completely protected the enzyme (100% recovery), while compound 1, quercetin and Trolox gave 54%, 34% and 12% recovery, respectively. All starting materials gave <15% recovery.

Antioxidant Effects on DNA

Figure 31:
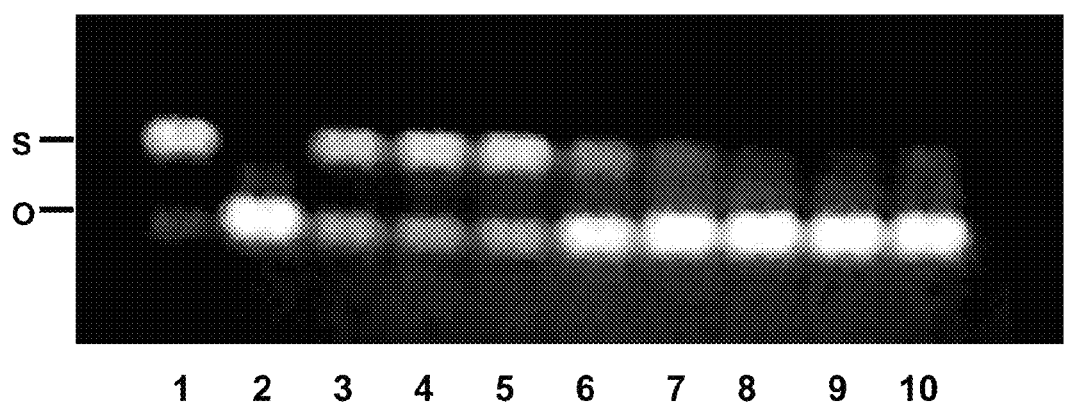
FIG. 31 is an image of an agarose gel of DNA treated with AAPH and compound 4.

Protection of DNA from free radical damage by the antioxidant dendrimers (compounds 4, 5, and 1) was also evaluated. Plasmid DNA (pBR 322) samples, were incubated with AAPH (final concentration 10 mM) at 37° C. for 4 h with antioxidants (final concentrations, 0.35-45 µM) and subjected to agarose electrophoresis. A gel obtained with compound 4 is shown in FIG. 31. In FIG. 31, lane 1 is native DNA, and lanes 2-10 are AAPH-oxidized DNA with 0, 45, 23, 11, 5, 3, 1.5, 0.7, and 0.35 µM antioxidant, respectively. The native DNA was mostly in its supercoiled (S) form (small amount of open circular, O, form was also visible, lane 1, FIG. 31). In the presence of AAPH, the DNA was transformed almost entirely into its O form (lane 2, FIG. 31). In the presence of 11-45 µM of compound 4, DNA was well protected (the S band intensity was similar to control (without AAPH), lanes 3-5, FIG. 31). Quercetin as well as compound 5 and compound 1 also displayed similar results (data not shown). Some protection was also obtained for the three dendrimers (compounds 4, 5, and 1) at 5 µM (lane 6, FIG. 31) but not with quercetin (data not shown). Negligible DNA protection was afforded by all three dendrimers at ≤2.5 µM (lanes 7-10, FIG. 31). Under similar conditions, Trolox as well as the starting materials for dendrimer synthesis were ineffective at all concentrations.

All of the above antioxidant activity tests clearly indicated that the antioxidant dendrimers were effective radical scavenging agents. This may be attributed to the presence of multiple phenolic hydroxyl groups, benzylic hydrogens, and electron donating substituents in these compounds.

Example 16

Pro-Oxidant Activities of Compound 4 and Compound 5

Figure 32:
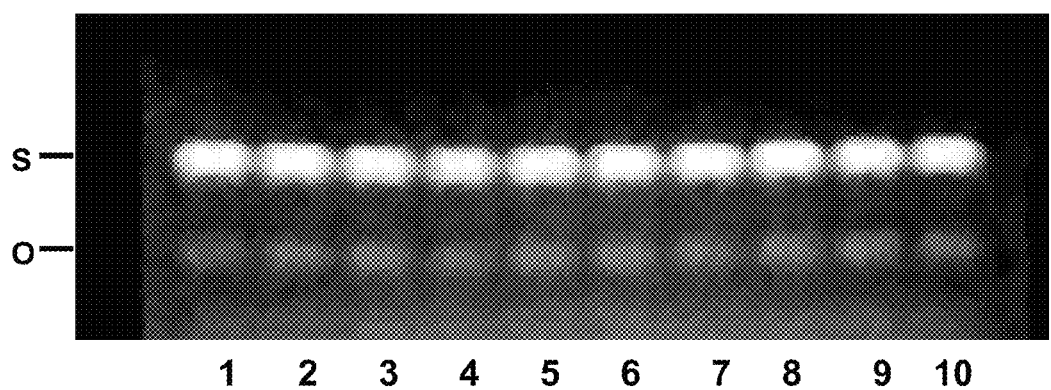
FIG. 32 is an image of an agarose gel of DNA incubated with compound 4 and Cu(II) ion.

The pro-oxidant property of antioxidants (in the presence of transition metals ions, such as $Cu^{2+}$ and $Fe^{3+}$) such as quercetin has been associated with their mutagenic and carcinogenic health hazard (Yamashita, N., et al. *Mutation Res.* 1999, 425, 107-115; Lebeau, J., et al. *Free Radic. Biol. Med.* 2000, 29, 900-912, incorporated herein by reference in their entireties), which is a drawback for potential clinical applications. Since potent antioxidants often possess strong pro-oxidant activity, the pro-oxidant behaviors of various dendritic antioxidants were examined. This was performed by co-incubation of DNA (pBR 322), copper (II) ion and antioxidant. It is believed that an antioxidant such as quercetin which displays strong pro-oxidant activity binds to Cu(II)-DNA complex through its catechol and forms a DNA-Cu(II)-quercetin complex. This ultimately forms DNA-Cu(I)OOH, initiating a free radical cascade by which DNA damage occurs. pBR 322 was incubated with 10 µM $Cu^{2+}$ in the presence of antioxidants (0-45 µM) at 37° C. for 1 h and subjected to agarose electrophoresis. FIG. 32 shows an agarose gel obtained with compound 4, to examine any pro-oxidant effect of compound 4 on DNA. In FIG. 32, lane 1 is native DNA, and lanes 2-10 are $Cu^{2+}$ oxidized DNA with 0, 45, 23, 11, 5, 3, 1.5, 0.7, and 0.35 µM antioxidant, respectively. No DNA damage was obtained at all concentrations between 0.35-45 µM. Compound 5 also showed similar results (data not shown). As shown above, DNA damage was clearly observed with compound 1, quercetin and Trolox at concentrations between 11-45 µM. The starting materials did not show any pro-oxidant effect on DNA under these conditions. These results suggested that the lack of pro-oxidant effects displayed by the two TREN-based dendrimers may be due to chelation of copper ions by the tertiary amines in the core. The metal chelating property of the dendrimers was likely overwhelmed at higher copper concentrations (e.g. 60 µM) resulting in pro-oxidative effects and DNA damage (data not shown). However, it should be noted that physiological concentrations of copper are less than 10-20 µM in plasma and approximately 10-18 M for the cation in cells. Therefore, chelation of even low amounts of cation can markedly affect free radical formation, especially in the chromatin region where one copper ion is present per kilobase.

Example 17

Cell Toxicity of Compound 4 and Compound 5

Data on cell toxicity of compound 4 and compound 5 were obtained with Chinese hamster ovary (CHO) cells using 3-(4, 5-di-methylthizol-2-yl)-2,5 diphenyltetrazolium bromide (MTT). Chinese Hamster Ovary (CHO-K1) cells were cultured in F-12K medium supplemented with 10% fetal bovine serum. The cells ($3 \times 10^5$/ml) were seeded in 100 µL volumes in 96 well culture plates and incubated with the solvent control (DMSO, 0.3%), compound 4 or compound 5 at 3.1, 6.2, 12.5, 25, or 50 µM for 1, 3, or 5 days. Two hours prior to experimental termination, 20 µL of a 5 mg/mL MTT solution in 0.01 M PBS was added to each well. Plates were centrifuged at 450×g for 10 min and supernatant was removed. The resultant formazan crystals were dissolved in 100 µL DMSO and mixed. Absorbance was measured using a Biolog microplate reader (Biotek Instruments) at dual wavelengths, 590 and 650 nm. Percent control response was calculated as follows: (absorbance of treatment/absorbance of control)×100. All experiments were performed in triplicate and repeated. The data were analyzed using Systat 12 for windows. Multiple groups were compared using a one-way analysis of variance (ANOVA) and a Tukey test for mean separation. A p value<0.05 was considered statistically significant.

Figure 33:
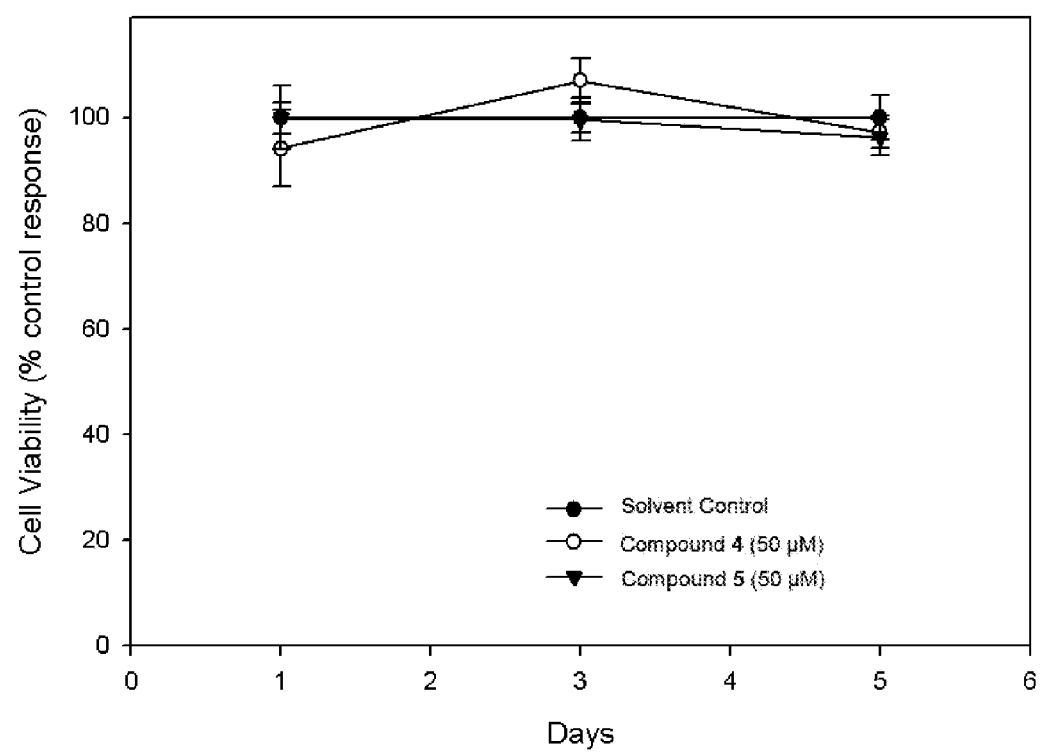
FIG. 33 is a graph of cell viability versus time for compound 4 and compound 5.

Incubation of the CHO cells ($3 \times 10^5$/mL) in the presence of 3.1-50 µM of antioxidants did not show any reduction in cell viability over 5 days (FIG. 33). For the data presented in FIG. 33, CHO cells were incubated with DMSO control, compound 4 (○), or compound 5 (▼) at 50 µM for 1, 3, and 5 days.

In summary, novel dendrimers with free radical scavenging as well as metal chelating properties have been discovered. The antioxidant dendrimers showed high radical scavenging activity and strong protective effects on biomolecules (LDL, lysozyme and DNA). Unlike other potent antioxidants, the TREN-based dendritic antioxidants devoid of pro-oxidant activity provided a significant biological benefit. With their strong radical scavenging potential and of pro-oxidant activity as well as cell toxicity, the compounds may be used as therapeutic agents for treating pathological conditions associated with oxidative stress including, for example, asthma, atherosclerosis, and neurodegenerative diseases.

What is claimed is:
1. A compound of General Formula I:

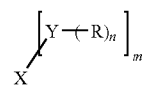

wherein X is a multi-valent center selected from the group consisting of

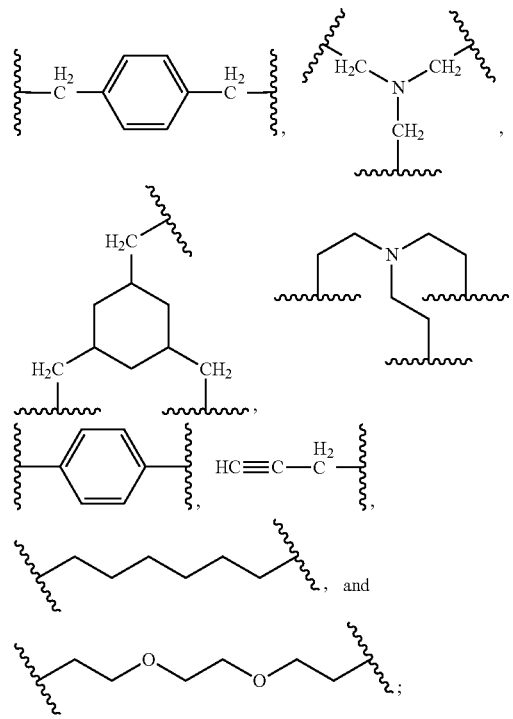

Y is selected from the group consisting of N and C;
n is 2, if Y is N; and n is 3, if Y is C;
m is 1 to 4;
R is:

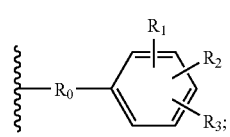

wherein $R_0$ is selected from the group consisting of a direct bond, alkylene, alkenylene, alkynylene, heteroalkylene, heteroalkenylene, heteroalkynylene, azidylene, —$NR_{32}$— and heterogenous groups; and $R_{32}$ is independently selected from the group consisting of hydrogen, alkyl, alkenyl, alkynyl, heteroalkyl, heteroalkenyl, heteroalkynyl, aryl, heteroaryl, cycloalkyl and heterocycloalkyl;

$R_1$, $R_2$, and $R_3$ are independently selected from the group consisting of hydrogen, halo, —$R_4$, and —O—$R_4$, wherein $R_4$ is selected from the group consisting of hydrogen, alkylamino, heteroalkyl, hydroxyalkyl, alkylazide, and —$R_6$—N($R_7$)($R_8$);

at least one of $R_1$, $R_2$, and $R_3$ is —OH;

$R_6$ is selected from the group consisting of alkylene, alkenylene, alkynylene, heteroalkylene, heteroalkenylene, heteroalkynylene, azidylene, and heterogenous groups; and $R_7$ and $R_8$ are independently selected from the group consisting of hydrogen and —A, wherein A is

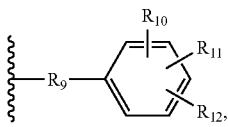

wherein $R_9$ is selected from the group consisting of a direct bond, alkylene, alkenylene, alkynylene, heteroalkylene, heteroalkenylene, heteroalkynylene, azidylene, —$NR_{32}$— and heterogenous groups;

$R_{32}$ is independently selected from the group consisting of hydrogen, alkyl, alkenyl, alkynyl, heteroalkyl, heteroalkenyl, heteroalkynyl, aryl, heteroaryl, cycloalkyl and heterocycloalkyl; and $R_{10}$, $R_{11}$, and $R_{12}$ are independently selected from the group consisting of hydrogen, halo, —$R_{13}$, and —O—$R_{13}$, wherein $R_{13}$ is selected from the group consisting of hydrogen, alkyl, alkylamino, heteroalkyl, hydroxyalkyl, alkylazide, alkenyl, and —$R_{14}$—N($R_{15}$)($R_{16}$); and at least one of $R_{10}$, $R_{11}$, and $R_{12}$ is —OH;

$R_{14}$ is selected from the group consisting of alkylene, alkenylene, alkynylene, heteroalkylene, heteroalkenylene, heteroalkynylene, azidylene and heterogenous groups; and $R_{15}$ and $R_{16}$ are independently selected from the group consisting of hydrogen and —B, wherein B is

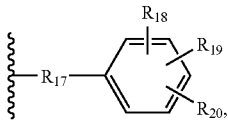

wherein $R_{17}$ is selected from the group consisting of a direct bond, alkylene, alkenylene, alkynylene, heteroalkylene, heteroalkenylene, heteroalkynylene, azidylene, —$NR_{32}$—, and heterogenous groups;

$R_{32}$ is independently selected from the group consisting of hydrogen, alkyl, alkenyl, alkynyl, heteroalkyl, heteroalkenyl, heteroalkynyl, aryl, heteroaryl, cycloalkyl, and heterocycloalkyl; and $R_{18}$, $R_{19}$, and $R_{20}$ are independently selected from the group consisting of hydrogen, halo, —$R_{21}$, and —O—$R_{21}$, wherein $R_{21}$ is selected from the group consisting of hydrogen, alkyl, alkylamino, heteroalkyl, hydroxyalkyl, alkylazide, and alkenyl; and at least one of $R_{18}$, $R_{19}$, and $R_{20}$ is —OH.

2. The compound of claim 1, wherein at least one of $R_1$, $R_2$, and $R_3$ is —$R_6$—N($R_7$)($R_8$) or —O—$R_6$—N($R_7$)($R_8$).

3. The compound of claim 1, wherein at least one of $R_{10}$, $R_{11}$, and $R_{12}$ is —$R_{14}$—N($R_{15}$)($R_{16}$) or —O—$R_{14}$—N($R_{15}$)($R_{16}$).

4. The compound of claim 1, wherein at least one of $R_1$, $R_2$, or $R_3$ is —O—$R_4$ wherein $R_4$ is alkylamino, alkyl, or hydrogen.

5. The compound of claim 1, wherein at least one of $R_{10}$, $R_{11}$, or $R_{12}$ is —O—$R_{13}$ wherein $R_{13}$ is alkylamino.

6. The compound of claim 1, wherein at least one of $R_{18}$, $R_{19}$, and $R_{20}$ is —O—$R_{21}$ wherein $R_{21}$ is alkylamino.

7. The compound of claim 1, wherein X is

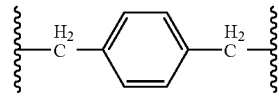

and $R_0$ is methylene.

8. The compound of claim 1, wherein X is

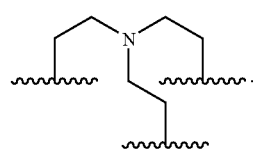 [SMILES: *CCN(CC*)CC*]

9. The compound of claim 1, wherein Y is N.

10. The compound of claim 1, wherein R is

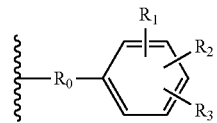

and $R_0$ is alkylene.

11. The compound of claim 1, wherein R is

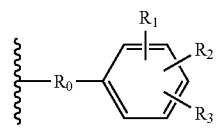

and at least one of $R_1$, $R_2$, and $R_3$ is —O—$R_4$ wherein $R_4$ is hydrogen or alkyl.

12. The compound of claim 1, wherein X is

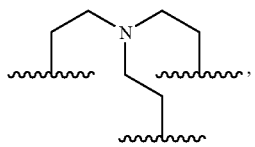

Y is N, $R_0$ is alkylene, and at least one of $R_1$, $R_2$, and $R_3$ is —O—$R_4$ wherein $R_4$ is hydrogen or alkyl.

13. The compound of claim 1, wherein the compound is selected from the group consisting of:

Compound 1

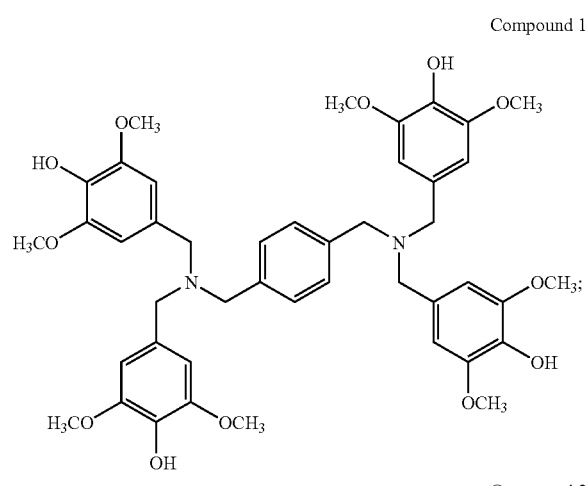

Compound 2

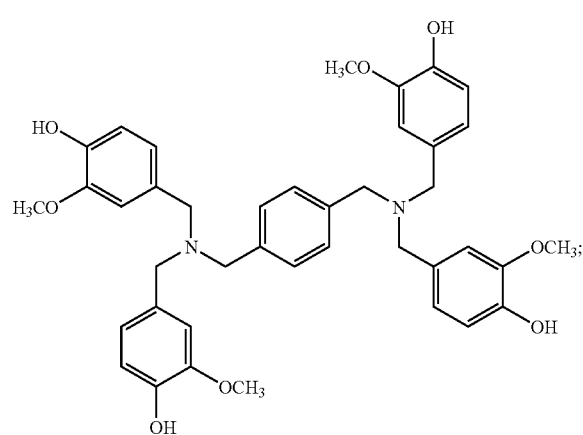

Compound 3

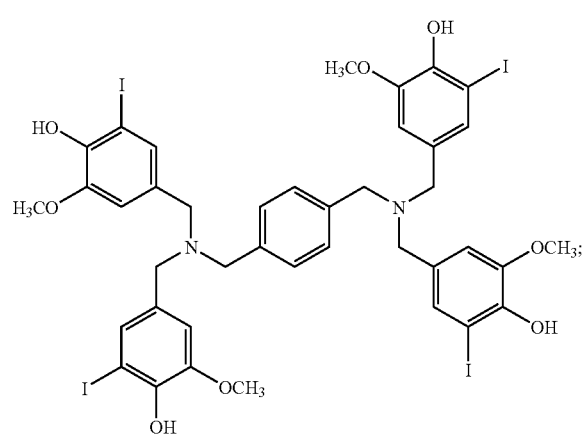

-continued

Compound 4

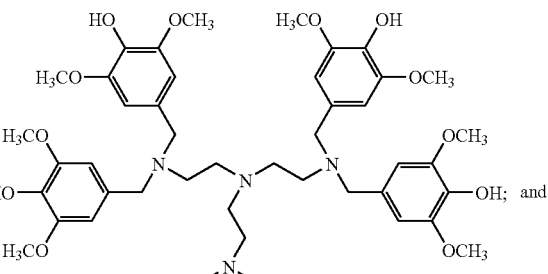
and

Compound 5

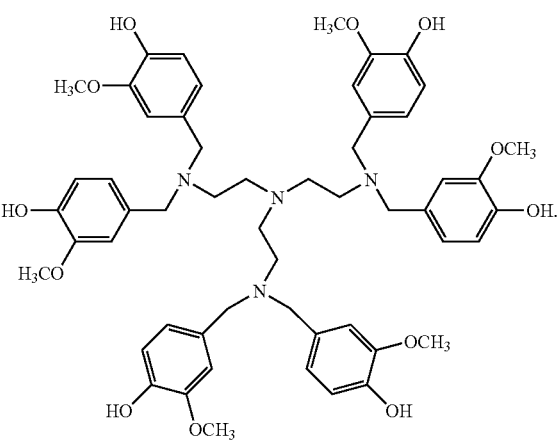

14. A composition comprising at least one active agent covalently attached to the compound according to claim 1.

15. The composition of claim 14, wherein the active agent is attached through a linker.

16. The composition of claim 15, wherein the linker is selected from the group consisting of alkylene, heteroalkylene, alkenylene, heteroalkenylene, alkynylene, heteroalkynylene, arylene, heteroarylene, —$NR_{32}$—, —C(O)$NR_{32}$—, —C(O)O—, azidylene, and —C(O)— groups; wherein $R_{32}$ is independently selected from hydrogen, alkyl, alkenyl, alkenyl, alkynyl, heteroalkyl, heteroalkenyl, heteroalkynyl, aryl, heteroaryl, cycloalkyl and heterocycloalkyl.

17. The composition of claim 14, wherein the active agent is covalently attached to $R_4$, $R_{13}$, or $R_{21}$.

18. The composition of claim 14, wherein the active agent is selected from the group consisting of antibiotics, analgesics, anti-inflammatory agents, chemotherapeutic agents, asthma therapeutics, hormones, or cardiovascular drugs.

19. The composition of claim 18, wherein the active agent is a chemotherapeutic selected from the group consisting of docetaxel or bicalutamide.

20. The composition of claim 14, wherein the active agent is a steroid selected from the group consisting of prednisolone.

21. The composition of claim 18, wherein the active agent is a cardiovascular drug selected from the group consisting of statins and niacin.

22. The composition of claim 14, wherein the active agent is a cell-targeting agent or an imaging agent.

23. A cosmetic composition comprising the compound of claim 1 and a cosmetically acceptable excipient.

24. A method of reducing free radicals or oxidative stress in a cell comprising contacting the cell with an effective amount of the compound of claim 1.

25. A method of treatment comprising administering to a subject in need thereof an effective amount of the compound of claim 1 or the composition of claim 14.

26. A method of evaluating a subject comprising administering to the subject the composition of claim 14, wherein the active agent is an imaging agent, and detecting the imaging agent in the subject.

27. A method of delivering an active agent comprising administering the composition of claim 14.

28. A method of treating a condition in a subject comprising administering to the subject an effective amount of the compound claim 1 or the composition of claim 14.

29. The method of claim 28, wherein the condition is inflammation, cancer, asthma, a neurological disorder, a cardiovascular disease, or diabetes.

30. A dietary supplement comprising the compound of claim 1.

* * * * *